(12) United States Patent
Adams et al.

(10) Patent No.: US 12,065,500 B2
(45) Date of Patent: Aug. 20, 2024

(54) METHODS OF TREATING CANCERS AND ENHANCING EFFICACY OF T CELL REDIRECTING THERAPEUTICS

(71) Applicants: Janssen Biotech, Inc., Horsham, PA (US); Stichting VUmc, Amsterdam (NL)

(72) Inventors: Homer Adams, Quakertown, PA (US); Francois Gaudet, Princeton, NJ (US); Niels Van de Donk, De Boelalaan (NL); Kris Frerichs, De Boelelaan (NL); Christie Verkleij, De Boelelaan (NL)

(73) Assignees: Janssen Biotech, Inc., Horsham, PA (US); Stichting VUmc, Amsterdam (NL)

( * ) Notice: Subject to any disclaimer, the term of this patent is extended or adjusted under 35 U.S.C. 154(b) by 671 days.

(21) Appl. No.: 16/412,701

(22) Filed: May 15, 2019

(65) Prior Publication Data
US 2019/0352421 A1 Nov. 21, 2019

Related U.S. Application Data

(60) Provisional application No. 62/842,080, filed on May 2, 2019, provisional application No. 62/736,804, filed on Sep. 26, 2018, provisional application No. 62/672,222, filed on May 16, 2018.

(51) Int. Cl.
| | |
|---|---|
| C07K 16/28 | (2006.01) |
| A61K 45/06 | (2006.01) |
| A61P 35/00 | (2006.01) |
| A61P 35/02 | (2006.01) |
| C07K 16/30 | (2006.01) |
| C07K 16/46 | (2006.01) |
| A61K 39/00 | (2006.01) |

(52) U.S. Cl.
CPC .......... *C07K 16/2896* (2013.01); *A61K 45/06* (2013.01); *A61P 35/00* (2018.01); *A61P 35/02* (2018.01); *C07K 16/2809* (2013.01); *C07K 16/2878* (2013.01); *C07K 16/30* (2013.01); *C07K 16/468* (2013.01); *A61K 2039/505* (2013.01); *C07K 2317/21* (2013.01); *C07K 2317/24* (2013.01); *C07K 2317/31* (2013.01); *C07K 2317/565* (2013.01); *C07K 2317/71* (2013.01)

(58) Field of Classification Search
CPC ............ C07K 16/2896; C07K 16/2809; C07K 16/2878; C07K 16/30; C07K 16/468; C07K 2317/21; C07K 2317/24; C07K 2317/31; C07K 2317/565; C07K 2317/71; A61K 45/06; A61K 2039/505; A61K 31/454; A61P 35/00; A61P 35/02
See application file for complete search history.

(56) References Cited

U.S. PATENT DOCUMENTS

| | | |
|---|---|---|
| 5,223,409 A | 6/1993 | Ladner et al. |
| 5,403,484 A | 4/1995 | Ladner et al. |
| 5,427,908 A | 6/1995 | Dower et al. |
| 5,571,698 A | 11/1996 | Ladner et al. |
| 5,580,717 A | 12/1996 | Dower et al. |
| 5,885,793 A | 3/1999 | Griffiths et al. |
| 5,932,448 A | 8/1999 | Tso et al. |
| 5,969,108 A | 10/1999 | McCafferty et al. |
| 6,172,197 B1 | 1/2001 | McCafferty et al. |
| 6,521,404 B1 | 2/2003 | Griffiths et al. |
| 6,521,427 B1 | 2/2003 | Evans |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,670,127 B2 | 12/2003 | Evans |
| 6,737,056 B1 | 5/2004 | Presta |
| 6,833,441 B2 | 12/2004 | Wang et al. |
| 7,829,673 B2 | 11/2010 | De Weers et al. |
| 8,088,896 B2 | 1/2012 | Tesar et al. |
| 8,153,765 B2 | 4/2012 | Park et al. |
| 8,236,308 B2 | 8/2012 | Kischel et al. |
| 9,150,663 B2 | 10/2015 | Labrijn et al. |
| 2007/0287170 A1 | 12/2007 | Davis et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2010/0092489 A1 | 4/2010 | Van De Winkel et al. |
| 2011/0123532 A1 | 5/2011 | Gurney et al. |
| 2012/0149876 A1 | 6/2012 | Von Kreudenstein et al. |
| 2013/0195849 A1 | 8/2013 | Spreter Von Kreudenstein et al. |
| 2014/0051662 A1* | 2/2014 | Moussy .................. A61K 31/10 514/64 |

(Continued)

FOREIGN PATENT DOCUMENTS

| | | |
|---|---|---|
| CL | 2020/002945 A1 | 3/2021 |
| CN | 106 163547 A | 11/2016 |

(Continued)

OTHER PUBLICATIONS

Krejcik et al. (Clin Cancer Res, 23(24): 7498-7511, 2017).*
Abhinandan, K. and Martin, A., Analysis and improvements to Kabat and structurally correct numbering of antibody variable domains, Mol Immunol., 45(14):3832-9 (2008).
Adams, P. et al., Recent developments in the PHENIX software for automated crystallographic structure determination, J Synchrotron Radiat., 11(Pt 1):53-5 (2004).
Adriouch, S. et al., Extracellular NAD+: a danger signal hindering regulatory T cells, Microbes and Infection, 14(14):1284-1292, (2012).
Anasetti, C. et al., Treatment of acute graft-versus-host disease with a nonmitogenic anti-CD3 monoclonal antibody, Transplantation, 54(5):844-51 (1992).

(Continued)

*Primary Examiner* — Nelson B Moseley, II
(74) *Attorney, Agent, or Firm* — Choate, Hall & Stewart LLP; Rolando Medina; Meaghan E. Bychowski

(57) ABSTRACT

Disclosed are methods of treating cancers and enhancing efficacy of T cell redirecting therapeutics.

28 Claims, 44 Drawing Sheets
Specification includes a Sequence Listing.

(56) References Cited

U.S. PATENT DOCUMENTS

| | | | |
|---|---|---|---|
| 2014/0112962 A1* | 4/2014 | Kim | A61K 9/2013 424/400 |
| 2014/0303356 A1 | 10/2014 | Gramer et al. | |
| 2014/0323315 A1* | 10/2014 | Bobrowicz | G01N 33/68 506/1 |
| 2015/0246975 A1 | 9/2015 | Doshi | |
| 2016/0166689 A1 | 6/2016 | Adler et al. | |
| 2016/0347849 A1* | 12/2016 | Cai | A61P 35/00 |
| 2017/0051068 A1* | 2/2017 | Pillarisetti | C07K 16/2878 |
| 2017/0121414 A1* | 5/2017 | Jansson | A61K 47/22 |
| 2017/0152315 A1 | 6/2017 | Hansen et al. | |
| 2017/0174780 A1 | 6/2017 | Doshi | |
| 2017/0209571 A1 | 7/2017 | Kanapuram et al. | |
| 2018/0037651 A1 | 2/2018 | Attar et al. | |
| 2018/0118849 A1 | 5/2018 | Klein et al. | |
| 2019/0284294 A1 | 9/2019 | Deslandes et al. | |
| 2019/0352421 A1 | 11/2019 | Adams et al. | |

FOREIGN PATENT DOCUMENTS

| | | | |
|---|---|---|---|
| TW | 2016/23333 A | 7/2016 | |
| TW | 2017/26168 A | 8/2017 | |
| TW | 2017/34053 A | 10/2017 | |
| TW | 2018/09005 A | 3/2018 | |
| WO | WO-1988/01649 A1 | 3/1988 | |
| WO | WO-1992/01047 A1 | 1/1992 | |
| WO | WO-1994/13804 A1 | 6/1994 | |
| WO | WO-1996/027011 A1 | 9/1996 | |
| WO | WO-1998/44001 A1 | 10/1998 | |
| WO | WO-00/41474 A2 | 7/2000 | |
| WO | WO-01/24811 A1 | 4/2001 | |
| WO | WO-01/24812 A1 | 4/2001 | |
| WO | WO-02/066516 A2 | 8/2002 | |
| WO | WO-2004/078140 A2 | 9/2004 | |
| WO | WO-2006/028936 A2 | 3/2006 | |
| WO | WO-2007/042261 A2 | 4/2007 | |
| WO | WO-2007/059782 A1 | 5/2007 | |
| WO | WO-2007/117600 A2 | 10/2007 | |
| WO | WO-2007/147901 A1 | 12/2007 | |
| WO | WO-2008/119565 A2 | 10/2008 | |
| WO | WO-2008/119566 A2 | 10/2008 | |
| WO | WO-2008/119567 A2 | 10/2008 | |
| WO | WO-2009/085462 A1 | 7/2009 | |
| WO | WO-2009/132058 A2 | 10/2009 | |
| WO | WO-2009/134776 A2 | 11/2009 | |
| WO | WO-2010/037836 A2 | 4/2010 | |
| WO | WO-2010/037837 A2 | 4/2010 | |
| WO | WO-2010/037838 A2 | 4/2010 | |
| WO | WO-2010/051274 A2 | 5/2010 | |
| WO | WO-2010/093627 A2 | 8/2010 | |
| WO | WO-2010/104949 A2 | 9/2010 | |
| WO | WO 2011/131746 * | 10/2011 | C07K 16/28 |
| WO | WO-2011/131746 A2 | 10/2011 | |
| WO | WO-2011/143545 A1 | 11/2011 | |
| WO | WO-2012/022811 A1 | 2/2012 | |
| WO | WO-2012/066058 A1 | 5/2012 | |
| WO | WO-2012/143498 A1 | 10/2012 | |
| WO | WO-2013/072406 A1 | 5/2013 | |
| WO | WO-2013/072415 A1 | 5/2013 | |
| WO | WO-2013/096291 A2 | 6/2013 | |
| WO | WO-2013/157954 A1 | 10/2013 | |
| WO | WO-2014/089416 A1 | 6/2014 | |
| WO | WO-2014/093908 A2 | 6/2014 | |
| WO | WO-2014/122144 A1 | 8/2014 | |
| WO | WO-2016/036937 A1 | 3/2016 | |
| WO | WO-2016/090312 A1 | 6/2016 | |
| WO | WO-2017/025038 A1 | 2/2017 | |
| WO | WO-2017/031104 A1 | 2/2017 | |
| WO | WO-2018/037651 A1 | 3/2018 | |
| WO | WO-2018/083204 A1 | 5/2018 | |
| WO | WO-2018/147245 A1 | 8/2018 | |
| WO | WO-2018/187215 A1 | 10/2018 | |
| WO | WO-2019/057124 A1 | 3/2019 | |

OTHER PUBLICATIONS

Baert, F. et al., Influence of immunogenicity on the long-term efficacy of infliximab in Crohn's disease, N Engl J Med, 348(7):601-608, (2003).

Beiboer, S. et al., Guided selection of a pan carcinoma specific antibody reveals similar binding characteristics yet structural divergence between the original murine antibody and its human equivalent, J Mol Biol, 296(3):833-49 (2000).

Casset, F. et al., A peptide mimetic of an anti-CD4 monoclonal antibody by rational design, Biochem. Biophys. Res. Commun., 307(1):198-205 (2003).

Chames, P. and Baty, D., Bispecific antibodies for cancer therapy, Curr Opin Drug Disc Dev, 12(2):276-283 (2009).

Chiarugi, A. et al., The NAD metabolome—a key determinant of cancer cell biology, Nat Rev Cancer, 12(11):741-752 (2012).

Chothia, C. and Lesk, A. M., Canonical structures for the hypervariable regions of immunoglobulins, J. Mol. Biol., 196(4):901-917 (1987).

Cline, M.J., Perspectives for gene therapy: inserting new genetic information into mammalian cells by physical techniques and viral vectors, Pharmacol Ther., 29(1):69-92 (1985).

De Pascalis, R. et al., Grafting of "abbreviated" complementarity-determining regions containing specificity-determining residues essential for ligand contact to engineer a less immunogenic humanized monoclonal antibody, J Immunol., 169(6):3076-84 (2002).

Dose Escalation Study of Talquetamab in Participants With Relapsed or Refractory Multiple Myelonoma, 10 pages, https://clinicaltrials.gov/ct2/show/NCT03399799, last update posted: Jul. 15, 2022.

Drach, J. et al., Presence of a p53 gene deletion in patients with multiple myeloma predicts for short survival after conventional-dose chemotherapy, Blood, 92(3):802-9 (1998).

Emsley, P. and Cowtan, K., Coot: model-building tools for molecular graphics, Acta Crystallogr D Biol Crystallogr., 60(Pt 12 Pt 1):2126-32 (2004).

Facon, T. et al., Chromosome 13 abnormalities identified by FISH analysis and serum beta2-microglobulin produce a powerful myeloma staging system for patients receiving high-dose therapy, Blood, 97(6):1566-71 (2001).

Ferrara, C. et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol Bioeng., 93(5):851-61 (2006).

Ferrara, C. et al., The carbohydrate at FcgammaRIIIa Asn-162. An element required for high affinity binding to non-fucosylated IgG glycoforms, J Biol Chem., 281(8):5032-6 (2006).

Frankel, S. R. and Baeuerle, A. B., Targeting T cells to tumor cells using bispecific antibodies, Curr Opin Chem Biol, 17(3):385-392 (2013).

Funaro, A. et al., Involvement of the multilineage CD38 molecule in a unique pathway of cell activation and proliferation, J Immunol, 145(8), 2390-2396, (1990).

Gadi, V. et al., In vivo sensitization of ovarian tumors to chemotherapy by expression of E. coli purine nucleoside phosphorylase in a small fraction of cells, Gene Ther., 7(20):1738-43 (2000).

Gertz, M. et al., Clinical implications of t(11;14)(q13;q32), t(4;14)(p16.3;q32), and -17p13 in myeloma patients treated with high-dose therapy, Blood, 106(8):2837-40 (2005).

Gras, M. et al., BCMAp: an integral membrane protein in the Golgi apparatus of human mature B lymphocytes, Int Immunol., 7(7):1093-106 (1995).

Guse, A. H. et al., Regulation of calcium signalling in T lymphocytes by the second messenger cyclic ADP-ribose, Nature, 398(6722):70-73 (1999).

Holliger, P. et al., "Diabodies": small bivalent and bispecific antibody fragments, Proc Natl Acad Sci USA, 90(14):6444-8 (1993).

Holt, L. et al., Domain antibodies: proteins for therapy, Trends Biotechnol., 21(11):484-90 (2003).

Honegger, A. and Pluckthun, A., Yet another numbering scheme for immunoglobulin variable domains: an automatic modeling and analysis tool, J Mol Biol., 309(3):657-670 (2001).

(56) References Cited

OTHER PUBLICATIONS

Hoogenboom, H. R., and Winter, G., By-passing immunisation. Human antibodies from synthetic repertoires of germline VH gene segments rearranged in vitro, J Mol Biol, 227(2):381-388 (1992).

Hu, H. et al., Small Molecule Inhibitors of Protein Arginine Methyltransferases, Expert Opin Investig Drugs, 25(3):335-358 (2016).

Hymowitz, S. et al., Structures of APRIL-receptor complexes: like BCMA, TACI employs only a single cysteine-rich domain for high affinity ligand binding, J Biol Chem., 280(8):7218-27 (2005).

Kabat, E. et al., Sequences of Proteins of Immunological Interest, 5th Ed. Public Health Service, National Institutes of Health, Bethesda, Md., 25 pages (1991).

Knappik, A. et al., Fully synthetic human combinatorial antibody libraries (HuCAL) based on modular consensus frameworks and CDRs randomized with trinucleotides, J. Mol. Biol., 296(1):57-86 (2000).

Konno, Y. et al., Fucose content of monoclonal antibodies can be controlled by culture medium osmolality for high antibody-dependent cellular cytotoxicity, Cytotechnology, 64(3):249-65 (2012).

Krebs, B. et al., High-throughput generation and engineering of recombinant human antibodies, J Immunol Methods, 254(1-2):67-84 (2001).

Krejcik, J. et al., Monocytes and Granulocytes Reduce CD38 Expression Levels on Myeloma Cells in Patients Treated with Daratumumab, Clin Cancer Res., 23(24):7498-7511 (2017).

Laâbi, Y. et al., A new gene, BCM, on chromosome 16 is fused to the interleukin 2 gene by a t(4;16)(q26;p13) translocation in a malignant T cell lymphoma, EBMO J., 11(11):3897-904 (1992).

Lefranc, M. et al., IMGT unique numbering for immunoglobulin and T cell receptor variable domains and Ig superfamily V-like domains, Dev Comp Immunol., 27(1):55-77 (2003).

Madry, C. et al., The characterization of murine BCMA gene defines it as a new member of the tumor necrosis factor receptor superfamily, Int Immunol., 10(11):1693-702 (1998).

Mariuzza, R. et al., The structural basis of antigen-antibody recognition, Annu Rev Biophys Biophys Chem., 16:139-59 (1987).

Marks, J. et al., By-passing immunization. Human antibodies from V-gene libraries displayed on phage, J Mol Biol., 222(3):581-97 (1991).

Martin, A. and Thornton, A., Structural families in loops of homologous proteins: automatic classification, modelling and application to antibodies, J Mol Biol., 263(5):800-15 (1996).

May, C. et al., Advances in bispecific biotherapeutics for the treatment of cancer, Biochem Pharmacol., 84(9):1105-12 (2012).

Mori, K. et al., Engineering Chinese hamster ovary cells to maximize effector function of produced antibodies using FUT8 siRNA, Biotechnol Bioeng., 88(7):901-8 (2004).

Myers, E. and Miller, W., Optimal alignments in linear space, Comput Appl Biosci., 4(1):11-7 (1988).

Needleman, S. and Wunsch, C., A general method applicable to the search for similarities in the amino acid sequence oftwo proteins, J Mol Biol., 48(3):443-53 (1970).

Nijhof, I. et al., CD38 expression and complement inhibitors affect response and resistance to daratumumab therapy in myeloma, Blood, 128(7):959-70 (2016).

Nijhof, I. et al., Upregulation of CD38 expression on multiple myeloma cells by all-trans retinoic acid improves the efficacy of daratumumab, Leukemia, 29(10):2039-49 (2015).

No Author Listed, Dose Escalation Study of Talquetamab in Participants With Relapsed or Refractory Multiple Myeloma, ClinicalTrials.gov Identifier: NCT03399799, 10 pages, last update posted Jul. 15, 2022.

Novak, A. et al., Expression of BCMA, TACI, and BAFF-R in multiple myeloma: a mechanism for growth and survival, Blood, 103(2):689-94 (2004).

Nunez-Prado, N. et al., The coming of age of engineered multivalent antibodies, Drug Discov Today, 20(5):588-94 (2015).

Okayama, H. and Berg, P., A cDNA cloning vector that permits expression of cDNA inserts in mammalian cells, Mol Cell Biol., 3(2):280-9 (1983).

Olivier, S. et al., EB66 cell line, a duck embryonic stem cell-derived substrate for the industrial production of therapeutic monoclonal antibodies with enhanced ADCC activity, Mabs, 2(4):405-15 (2010).

Osborn, M. et al., High-affinity IgG antibodies develop naturally in Ig-knockout rats carrying germline human IgH/Ig?/Ig? loci bearing the rat CH region, J Immunol., 190(4):1481-90 (2013).

Otwinowski, Z. and Minor, W., Processing of X-Ray Diffraction Data Collected in Oscillation Mode, Methods in Enzymology, 276:307-326 (1997).

Padlan, E. et al., Structure of an antibody-antigen complex: crystal structure of the HyHEL-10 Fab-lysozyme complex, Proc Natl Acad Sci USA, 86(15):5938-42 (1989).

Read, R.J., Pushing the boundaries of molecular replacement with maximum likelihood, Acta Crystallogr D Biol Crystallogr., 57(Pt 10):1373-82 (2001).

Revets, H. et al., Nanobodies as novel agents for cancer therapy, Expert Opin Biol Ther., 5(1):111-24 (2005).

Rickert, R. et al., Signaling by the tumor necrosis factor receptor superfamily in B-cell biology and disease, Immunol Rev., 244(1):115-33 (2011).

Salmerón, A. et al., A conformational epitope expressed upon association of CD3-epsilon with either CD3-delta or CD3-gamma is the main target for recognition by anti-CD3 monoclonal antibodies, J Immunol., 147(9):3047-52 (1991).

Sheets, M. et al., Efficient construction of a large nonimmune phage antibody library: the production of high-affinity human single-chain antibodies to protein antigens, Proc Natl Acad Sci USA, 95(11):6157-62 (1998).

Shi, L. et al., De novo selection of high-affinity antibodies from synthetic fab libraries displayed on phage as pIX fusion proteins, J Mol Biol., 397(2):385-96 (2010).

Shields, R. et al., Lack of fucose on human IgG1 N-linked oligosaccharide improves binding to human Fcgamma RIII and antibody-dependent cellular toxicity, J Biol Chem., 277(30):26733-40 (2002).

Shinkawa, T. et al., The absence of fucose but not the presence of galactose or bisecting N-acetylglucosamine of human IgG1 complex-type oligosaccharides shows the critical role of enhancing antibody-dependent cellular cytotoxicity, J Biol Chem., 278(5):3466-73 (2003).

Stickler, M. et al., The human G1m1 allotype associates with CD4+ T-cell responsiveness to a highly conserved IgG1 constant region peptide and confers an asparaginyl endopeptidase cleavage site, Genes Immun., 12(3):213-21 (2011).

Tai, Y. and Anderson, K., Targeting B-cell maturation antigen in multiple myeloma, Immunotherapy, 7(11):1187-99 (2015).

Terhorst, C. et al., Biochemical studies of the human thymocyte cell-surface antigens T6, T9 and T10, Cell, 23(3):771-80 (1981).

Van Der Veer, M. et al., The therapeutic human CD38 antibody daratumumab improves the anti-myeloma effect of newly emerging multi-drug therapies, Blood Cancer J., 1(10):e41 (2011).

Van Der Veer, M. et al., Towards effective immunotherapy of myeloma: enhanced elimination of myeloma cells by combination of lenalidomide with the human CD38 monoclonal antibody daratumumab, Haematologica, 96(2):284-90 (2011).

Vaughan, T. et al., Human antibodies with sub-nanomolar affinities isolated from a large non-immunized phage display library, Nat Biotechnol, 14(3):309-14 (1996).

Ward, E. et al., Binding activities of a repertoire of single immunoglobulin variable domains secreted from *Escherichia coli*, Nature, 341(6242):544-6 (1989).

Wu, T. and Kabat, E., An analysis of the sequences of the variable regions of Bence Jones proteins and myeloma light chains and their implications for antibody complementarity, J Exp Med., 132(2):211-50 (1970).

Yang, S. et al., A common pathway for T lymphocyte activation involving both the CD3-Ti complex and CD2 sheep erythrocyte receptor determinants, J Immunol., 137(4):1097-100 (1986).

Zhou, Q. et al., Development of a simple and rapid method for producing non-fucosylated oligomannose containing antibodies with increased effector function, Biotechnol Bioeng., 99(3):652-65 (2008).

(56) References Cited

OTHER PUBLICATIONS

Goebeler, M. et al.. Bispecific T-Cell Engager (BiTE) Antibody Construct Blinatumomab for the Treatment of Patients With Relapsed/Refractory Non-Hodgkin Lymphoma: Final Results From a Phase 1 Study, J Clin Oncol., 34(10):1104-11 (2016).

Grzasko, N. et al., Chromosome 1 amplification has similar prognostic value to del(17p13) and t(4;14)(p16;q32) in multiple myeloma patients: analysis of real-life data from the Polish Myeloma Study Group, Leuk Lymphoma, 58(9):1-15 (2017).

Hipp, S. et al., A novel BCMA/CD3 bispecific T-cell engager for the treatment of multiple myeloma induces selective lysis in vitro and in vivo, Leukemia, 31(8):1743-1751 (2017).

Sanchez, E., et al., The Role of B-Cell Maturation Antigen in the Biology and Management of, and as a Potential Therapeutic Target in, Multiple Myeloma, Target Oncol., 13(1):39-47 (2018).

Seckinger, A. et al., Target Expression, Generation, Preclinical Activity, and Pharmacokinetics of the BCMA-T Cell Bispecific Antibody EM801 for Multiple Myeloma Treatment, Cancer Cell, 31(3):396-410 (2017).

Study of bb2121 in Multiple Myeloma, 8 pages, https://https://clinicaltrials.gov/ct2/show/NCT02658929, last update posted: Dec. 4, 2020.

Topp, M. et al., Treatment with AMG 420, an Anti-B-Cell Maturation Antigen (BCMA) Bispecific T-Cell Engager (BiTE) Antibody Construct, Induces Minimal Residual Disease (MRD) Negative Complete Responses in Relapsed and/or Refractory (R/R) Multiple Myeloma (MM) Patients: Results of a First-in-Human (FIH) Phase I Dose Escalation Study, Blood,132, 5 pages (2018).

Practical Guidelines for Hematological Malignancies, 2013, III. Myeloma, The Japanese Society of Hematology, http://www.jshem.or.jp/gui-hemali2013/3_1.html#soron.

Atanackovic, D. et al., Chimeric Antigen Receptor (CAR) therapy for multiple myeloma, Br J Haematol., 172(5):685-698 (2016).

Frerichs, K. et al., Preclinical Evaluation of the New BCMA x CD3 Bispecific Antibody JNJ-957 for the Treatment of Multiple Myeloma, HemaSphere, 2(S1):729, Abs. S1579 (2018).

Girgis, S. et al., Exploratory Pharmacokinetic/Pharmacodynamic and Tolerability Study of BCMAxCD3 in Cynomolgus Monkeys, Blood, 128(22): 5668 (2016).

No Author Listed, Dose Escalation Study of Teclistamab, a Humanized BCMA*CD3 Bispecific Antibody, in Participants With Relapsed or Refractory Multiple Myeloma (MajesTEC-1), ClinicalTrials.gov Identifier: NCT03145181, 8 pages, last update posted Jan. 3, 2024. https://www.clinicaltrials.gov/study/NCT03145181?term=teclistamab&firstPost=_2019-05-14&rank=1&a=1&tab=history.

Sanchez, L. et al., Daratumumab: a first-in-class CD38 monoclonal antibody for the treatment of multiple myeloma, Journal of Hematology & Oncology, 9(51): 8 pages (2016).

Yichen, L. et al., Research progress of chimeric antigen receptor T cell immunotherapy in the treatment of multiple myeloma, Anhui Medical and Pharmaceutical Journal, 6:978-982 (2017).

\* cited by examiner

METHODS OF TREATING CANCERS AND ENHANCING EFFICACY OF T CELL REDIRECTING THERAPEUTICS

CROSS-REFERENCE TO RELATED APPLICATIONS

This application claims the benefit of U.S. Provisional Application Ser. No. 62/672,222, filed 16 May 2018, U.S. Provisional Application Ser. No. 62/736,804, filed 26 Sep. 2018, and U.S. Provisional Application Ser. No. 62/842,080, filed 2 May 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 18, 2024, is named 2013956-0003_SL.txt and is 133,755 bytes in size.

FIELD OF THE INVENTION

Disclosed are methods of treating cancers and enhancing efficacy of T cell redirecting therapeutics.

BACKGROUND OF THE INVENTION

T cell redirected killing is a desirable mode of action in many therapeutic areas. In general T cell redirecting molecules are engineered to have at least two antigen binding sites wherein one site binds a surface antigen on a target cell and the other site binds a T cell surface antigen. Amongst T cell surface antigens, the human CD3 epsilon subunit from the TCR protein complex has been the most targeted to redirect T cell killing Various bispecific antibody formats have been shown to mediate T cell redirection in both in pre-clinical and clinical investigations (May C et al., *Biochem Pharmacol*, 84: 1105-12, 2012; Frankel S R & Baeuerle P A, *Curr Opin Chem Biol*, 17(3): 385-92, 2013).

Tumors evade immune recognition through creating an immunosuppressive tumor microenvironment (TME). In the TME, under conditions of persistent antigen and inflammation, T cells become exhausted, or dysfunctional, and progressively lose their effector function and proliferative capacity. Impaired function and number of available T cells to engage therapeutics mediating T cell redirected killing may impair anti-tumor efficacy of the therapeutic. Therefore, there is a need to enhance T cell functionality for optimal efficacy of the therapeutics mediating T cell redirected killing.

SUMMARY OF THE INVENTION

The disclosure provides a method of treating a cancer in a subject, comprising administering a therapeutically effective amount of an anti-CD38 antibody and a T cell redirecting therapeutic to the subject to treat the cancer.

The disclosure also provides a method of killing a tumor cell in a subject, comprising administering to the subject an anti-CD38 antibody and a T cell redirecting therapeutic that binds an antigen on the tumor cell for a time sufficient to kill the tumor cell.

The disclosure provides a method of enhancing efficacy of a T cell redirecting therapeutic in a subject having a cancer, comprising administering to the subject an anti-CD38 antibody.

The disclosure also provides a method of treating a cancer in a subject, comprising administering a therapeutically effective amount of a BCMAxCD3 bispecific antibody and an anti-CD38 antibody to the subject to treat the cancer.

The disclosure also provides method of treating a cancer in a subject, comprising administering a therapeutically effective amount of a BCMAxCD3 bispecific antibody to the subject to treat the cancer, wherein the subject has been treated with an anti-CD38 antibody prior to administering the BCMAxCD3 bispecific antibody.

The disclosure also provides a method of treating a cancer in a subject, comprising administering a therapeutically effective amount of a BCMAxCD3 bispecific antibody to the subject to treat the cancer, wherein the subject is relapsed or refractory to treatment with a prior anti-cancer therapeutic.

The disclosure also provides a method of treating a multiple myeloma in a subject, comprising administering a therapeutically effective amount of a BCMAxCD3 bispecific antibody and an anti-CD38 antibody to the subject to treat the multiple myeloma.

The disclosure also provides a method of treating a multiple myeloma in a subject, comprising administering a therapeutically effective amount of a BCMAxCD3 bispecific antibody to the subject to treat the multiple myeloma, wherein the subject has been treated with an anti-CD38 antibody prior to administering the BCMAxCD3 bispecific antibody.

The disclosure also provides a method of treating a multiple myeloma in a subject, comprising administering a therapeutically effective amount of a BCMAxCD3 bispecific antibody to the subject to treat the multiple myeloma, wherein the subject is relapsed or refractory to treatment with a prior multiple myeloma therapeutic.

The disclosure also provides a pharmaceutical composition comprising a BCMAxCD3 bispecific antibody comprising a BCMA binding domain comprising a VH of SEQ ID NO: 29 and a VL of SEQ ID NO: 30 and a CD3 binding domain comprising the VH of SEQ ID NO: 39 and the VL of SEQ ID NO: 40, and an anti-CD38 antibody comprising a VH of SEQ ID NO: 4 and the VL of SEQ ID NO: 5.

The disclosure also provides a method of treating a cancer in a subject, comprising administering a therapeutically effective amount of a T-cell redirecting therapeutic that binds GPRC5D and an anti-CD38 antibody to the subject to treat the cancer.

The disclosure also provides a method of treating a cancer in a subject, comprising administering a therapeutically effective amount of a GPRC5DxCD3 bispecific antibody to the subject to treat the cancer, wherein the subject is relapsed or refractory to treatment with a prior anti-cancer therapeutic.

The disclosure also provides a pharmaceutical combination comprising a GPRC5DxCD3 bispecific antibody comprising a GPRC5D binding domain comprising the HCDR1 of SEQ ID NO: 43, the HCDR2 of SEQ ID NO: 44, the HCDR3 of SEQ ID NO: 45, the LCDR1 of SEQ ID NO: 46, the LCDR2 of SEQ ID NO: 47 and the LCDR3 of SEQ ID NO: 48, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38 and an anti-CD38 antibody comprising the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

The disclosure also provides a method of treating a cancer in a subject, comprising administering a therapeutically effective amount of a T-cell redirecting therapeutic that binds CD19 and an anti-CD38 antibody to the subject to treat the cancer.

The disclosure also provides a method of enhancing efficacy of a T cell redirecting therapeutic that binds CD19 in a subject having a cancer, comprising administering to the subject an anti-CD38 antibody prior to administering the T cell redirecting therapeutic that binds CD19.

The disclosure also provides a pharmaceutical combination comprising a CD19xCD3 bispecific antibody comprising blinatumomab of SEQ ID NO: 53 an anti-CD38 antibody comprising the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

The disclosure also provides a kit comprising the pharmaceutical composition of the disclosure.

DETAILED DESCRIPTION OF THE INVENTION

Figure 1:
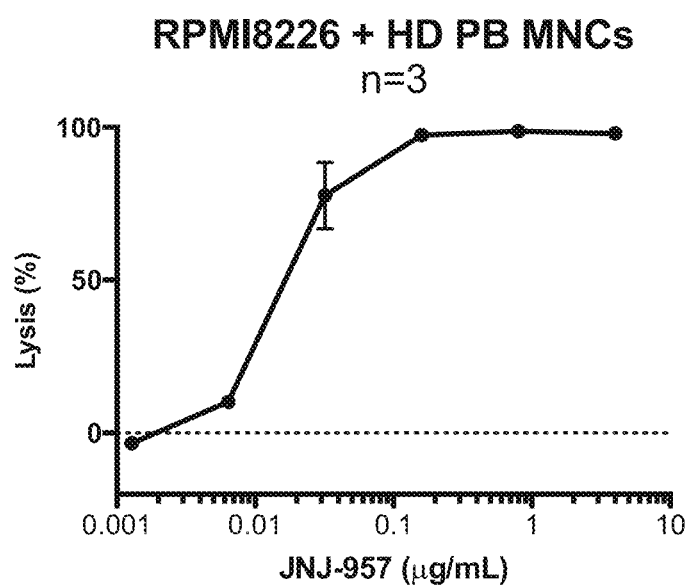
FIG. 1 shows JNJ-957-mediated lysis of multiple myeloma (MM) cell line RPMI8226. Healthy donor peripheral blood mononuclear cells (PB MNCs) were used as effector cells.
Figure 2:
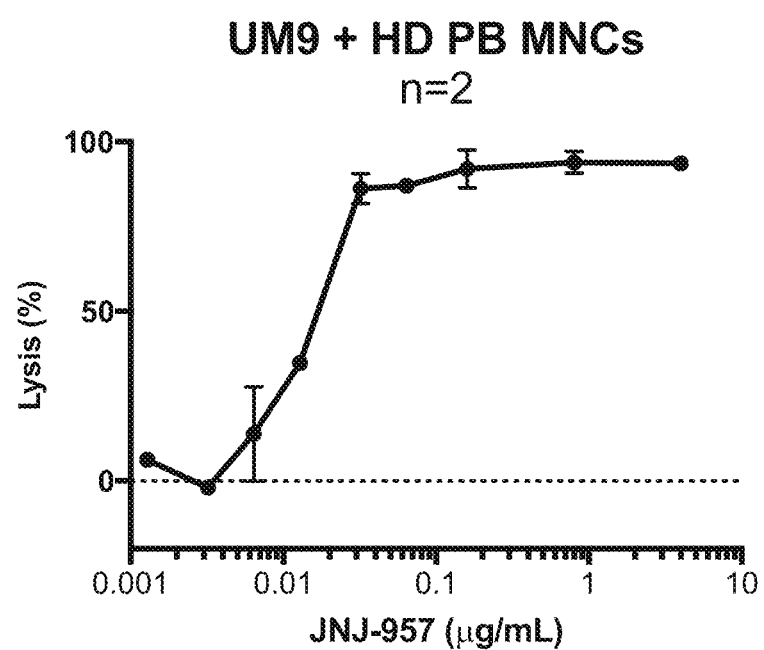
FIG. 2 shows JNJ-957-mediated lysis of multiple myeloma (MM) cell line UM9. Healthy donor peripheral blood mononuclear cells (PB MNCs) were used as effector cells.
Figure 3:
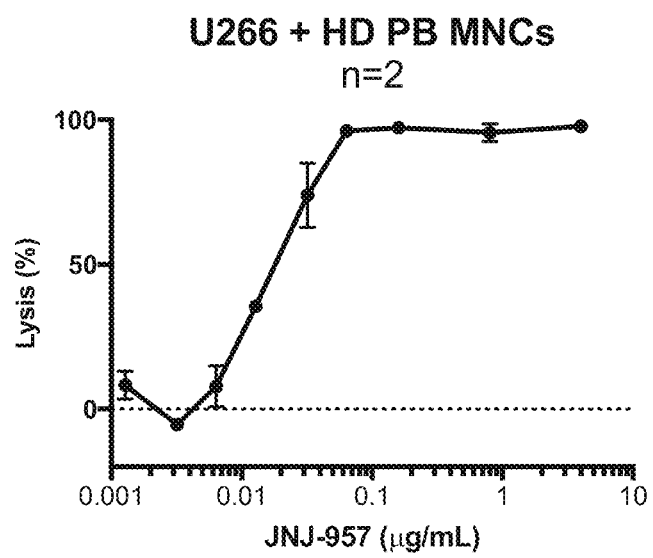
FIG. 3 shows JNJ-957-mediated lysis of multiple myeloma (MM) cell line U226. Healthy donor peripheral blood mononuclear cells (PB MNCs) were used as effector cells.
Figure 4:
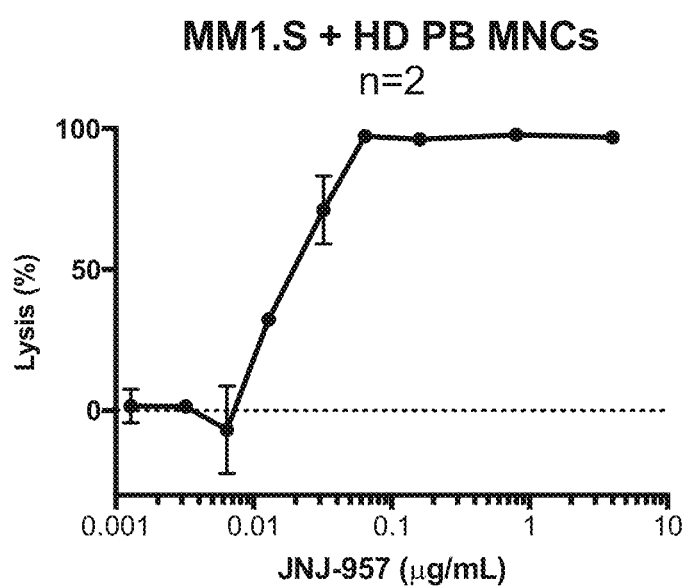
FIG. 4 shows JNJ-957-mediated lysis of multiple myeloma (MM) cell line MM1. Healthy donor peripheral blood mononuclear cells (PB MNCs) were used as effector cells.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods. All patents, published patent applications and publications cited herein are incorporated by reference as if set forth fully herein.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

"About" when used in reference to numerical ranges, cutoffs, or specific values means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of an assay, result or embodiment, "about" means within one standard deviation per the practice in the art, or a range of up to 5%, whichever is larger.

"Antibodies" is meant in a broad sense and includes immunoglobulin molecules including monoclonal antibodies including murine, human, humanized and chimeric monoclonal antibodies, antigen binding fragments, multi-specific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4 Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" or "antigen binding domain" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"BCMA" refers to human B-cell maturation antigen, also known as CD269 or TNFRSF17 (UniProt Q02223). The extracellular domain of BCMA encompasses residues 1-54 of Q02223. Human BCMA comprises the amino acid sequence of SEQ ID NO: 2.

SEQ ID NO: 2
MLQMAGQCSQNEYFDSLLHACIPCQLRCSSNTPPLTCQRYCNASVTNSVK

GTNAILWTCLGLSLIISLAVFVLMFLLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKS

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or Pan troglodytes, or may bind an epitope that is shared between two or more distinct antigens.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"CD123" refers to human Interleukin-3 receptor subunit alpha (IR3RA) having the amino acid sequence shown in SEQ ID NO: 57. The extracellular domain or CD123 spans residues 19-305 of SEQ ID NO: 57.

CD123
(SEQ ID NO: 57)
MVLLWLTLLLIALPCLLQTKEDPNPPITNLRMKAKAQQLTWDLNRNVTDI

ECVKDADYSMPAVNNSYCQFGAISLCEVTNYTVRVANPPFSTWILFPENS

GKPWAGAENLTCWIHDVDFLSCSWAVGPGAPADVQYDLYLNVANRRQQYE

CLHYKTDAQGTRIGCRFDDISRLSSGSQSSHILVRGRSAAFGIPCTDKFV

VFSQIEILTPPNMTAKCNKTHSFMHWKMRSHFNRKFRYELQIQKRMQPVI

TEQVRDRTSFQLLNPGTYTVQIRARERVYEFLSAWSTPQRFECDQEEGAN

TRAWRTSLLIALGTLLALVCVFVICRRYLVMQRLFPRIPHMKDPIGDSFQ

NDKLVVWEAGKAGLEECLVTEVQVVQKT

"CD19" refers to human B-lymphocyte antigen CD19 having the amino acid sequence of SEQ ID NO: 58. The extracellular domain of CD19 spans residues 20-291 of SEQ ID NO: 58.

CD19
(SEQ ID NO: 58)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR

"CD3" refers to a human antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 3. SEQ ID NO: 22 shows the extracellular domain of CD3 epsilon.

SEQ ID NO: 3
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI

SEQ ID NO: 22
DGNEEMGGITQTPYKVSISGTTVILTCPQYPGSEILWQHNDKNIGGDEDD

KNIGSDEDHLSLKEFSELEQSGYYVCYPRGSKPEDANFYLYLRARVCENC

MEMD

"CD33" refers to myeloid cell surface antigen CD33 having the amino acid sequence of SEQ ID NO: 97. The extracellular domain of CD33 spans residues 18-259 of SEQ ID NO: 97.

CD33
(SEQ ID NO: 97)
MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDGSGK

QETRAGVVHGAIGGAGVTALLALCLCLIFFIVKTHRRKAARTAVGRNDTH

PTTGSASPKHQKKSKLHGPTETSSCSGAAPTVEMDEELHYASLNFHGMNP

SKDTSTEYSEVRTQ

"CD38" refers to the human CD38 protein (UniProt accession no. P28907) (synonyms: ADP-ribosyl cyclase 1, cADPr hydrolase 1, cyclic ADP-ribose hydrolase 1). Human CD38 has an amino acid sequence as shown in SEQ ID NO: 1. CD38 is a single pass type II transmembrane protein with amino acid residues 1-21 representing the cytosolic domain, amino acid residues 22-42 representing the transmembrane domain, and residues 43-300 representing the extracellular domain.

SEQ ID NO: 1
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTSEI

"CH3 region" or "CH3 domain" refers to the CH3 region of an immunoglobulin. The CH3 region of human IgG1 antibody corresponds to amino acid residues 341-446. However, the CH3 region may also be any of the other antibody isotypes as described herein.

"Chimeric antigen receptor" or "CAR" refers to engineered T cell receptors which graft a ligand or antigen specificity onto T cells (for example naïve T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"Combination" means that two or more therapeutics are administered to a subject together in a mixture, concurrently as single agents or sequentially as single agents in any order.

"Complementarity determining regions" (CDR) are antibody regions that bind an antigen. CDRs may be defined using various delineations such as Kabat (Wu et al. *J Exp Med* 132: 211-50, 1970) (Kabat et al., Sequences of Proteins of Immunological Interest, 5th Ed. Public Health Service, National Institutes of Health, Bethesda, Md., 1991), Chothia (Chothia et al. J Mol Biol 196: 901-17, 1987), IMGT (Lefranc et al. *Dev Comp Immunol* 27: 55-77, 2003) and AbM (Martin and Thornton *J. Bmol Biol* 263: 800-15, 1996). The correspondence between the various delineations and variable region numbering are described (see e.g. Lefranc et al. *Dev Comp Immunol* 27: 55-77, 2003; Honegger and Pluckthun, *J Mol Biol* 309:657-70, 2001; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification "Comprising" is intended to include examples encompassed by the terms "consisting essentially of" and "consisting of"; similarly, the term "consisting essentially of" is intended to include examples encompassed by the term "consisting of." Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Enhance" or "enhanced" refers to enhancement in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g. ADCC, CDC and/or ADCP) or binding to an Fcγ receptor (FcγR) or FcRn. "Enhanced" may be an enhancement of about 10%, 20%, 30%, 40%, 50%, 60%, 70%, 80%, 90%, 100% or more, or a statistically significant enhancement.

"Fc gamma receptor" (FcγR) refers to well-known FcγRI, FcγRIIa, FcγRIIb or FcγRIII. Activating FcγR includes FcγRI, FcγRIIa and FcγRIII.

"GPRC5D" refers to human G-protein coupled receptor family C group 5 member D having the amino acid sequence shown in SEQ ID NO: 98.

GPRC5D
(SEQ ID NO: 98)
MYKDCIESTGDYFLLCDAEGPWGIILESLAILGIVVTILLLLAFLFLMRK

IQDCSQWNVLPTQLLFLLSVLGLFGLAFAFIIELNQQTAPVRYFLFGVLF

ALCFSCLLAHASNLVKLVRGCVSFSWTTILCIAIGCSLLQIIIATEYVTL

IMTRGMMFVNMTPCQLNVDFVVLLVYVLFLMALTFFVSKATFCGPCENWK

QHGRLIFITVLFSIIIWVVWISMLLRGNPQFQRQPQWDDPVVCIALVTNA

WVFLLLYIVPELCILYRSCRQECPLQGNACPVTAYQHSFQVENQELSRAR

DSDGAEEDVALTSYGTPIQPQTVDPTQECFIPQAKLSPQQDAGGV

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462.

Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Mutation" refers to an engineered or naturally occurring alteration in a polypeptide or polynucleotide sequence when compared to a reference sequence. The alteration may be a substitution, insertion or deletion of one or more amino acids or polynucleotides.

"Non-fixed combination" refers to separate pharmaceutical compositions of the T cell redirecting therapeutic and the anti-CD38 antibody administered as separate entities either simultaneously, concurrently or sequentially with no specific intervening time limits, wherein such administration provides effective levels of the two compounds in the body of the subject.

"Multispecific" refers to an antibody that specifically binds at least two distinct antigens or at least two distinct epitopes within the same antigen. Multispecific antibody may bind for example two, three, four or five distinct antigens or distinct epitopes within the same antigen.

"Pharmaceutical composition" refers to composition that comprises an active ingredient and a pharmaceutically acceptable carrier.

"Pharmaceutically acceptable carrier" or "excipient" refers to an ingredient in a pharmaceutical composition, other than the active ingredient, which is nontoxic to a subject.

"Philadelphia chromosome" or "Ph" refers to a well-known chromosomal translocation between chromosomes 9 and 22, resulting in the oncogenic BCR-ABL gene fusion with constitutively active tyrosine kinase activity. The translocation results in a portion of the BCR gene from chromosome 22q11 becoming fused with a portion of the ABL gene from chromosome 9q34, and is designated as t(9;22)(q34;q11) under the International System for Human Cytogenetic Nomenclature (ISCN). Depending on the precise location of the fusion, the molecular weight of the resulting fusion protein can range from 185 to 210 kDa. "Philadelphia chromosome" refers to all BCR-ABL fusion proteins formed due the (9;22)(q34;q11) translocation.

"PSMA" refers to human prostate specific membrane antigen having the amino acid sequence of SEQ ID NO: 99. The extracellular domain spans residues 44-750 of SEQ ID NO: 99.

PSMA
(SEQ ID NO: 99)
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLVYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVR

SFGTLKKEGWRPRRTILFASWDAEEFGLLGSTEWAEENSRLLQERGVAYI

NADSSIEGNYTLRVDCTPLMYSLVHNLTKELKSPDEGFEGKSLYESWTKK

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMKHPQEMKTYSVSFDSLFSAVKNFTEIASKFSERL

QDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA

"Recombinant" refers to DNA, antibodies and other proteins that are prepared, expressed, created or isolated by recombinant means when segments from different sources are joined to produce recombinant DNA, antibodies or proteins.

"Reduce" or "reduced" refers to a reduction in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g. ADCC, CDC and/or ADCP) or binding to an Fcγ receptor (FcγR) or FcRn. "Reduced" may be a reduction of about 10%, 20%, 30%, 40%, 50%, 60%, 70%, 80%, 90%, 100% or more, or a statistically significant enhancement.

"rHuPh20" refers to recombinant human hyalurodinase having the amino acid sequence of SEQ ID NO: 105, which is a recombinant hyaluronidase (HYLENEX® recombinant) described in Int'l Pat. Pub. No. WO2004/078140.

rHuPH20
(SEQ ID NO: 105)
MGVLKFKHIFFRSFVKSSGVSQIVFTFLLIPCCLTLNFRAPPVIPNVPFL

WAWNAPSEFCLGKFDEPLDMSLFSFIGSPRINATGQGVTIFYVDRLGYYP

YIDSITGVTVNGGIPQKISLQDHLDKAKKDITFYMPVDNLGMAVIDWEEW

```
-continued
RPTWARNWKPKDVYKNRSIELVQQQNVQLSLTEATEKAKQEFEKAGKDFL

VETIKLGKLLRPNHLWGYYLFPDCYNHHYKKPGYNGSCFNVEIKRNDDLS

WLWNESTALYPSIYLNTQQSPVAATLYVRNRVREAIRVSKIPDAKSPLPV

FAYTRIVFTDQVLKFLSQDELVYTFGETVALGASGIVIWGTLSIMRSMKS

CLLLDNYMETILNPYIINVTLAAKMCSQVLCQEQGVCIRKNWNSSDYLHL

NPDNFAIQLEKGGKFTVRGKPTLEDLEQFSEKFYCSCYSTLSCKEKADVK

DTDAVDVCIADGVCIDAFLKPPMETEEPQIFYNASPSTLSATMFIVSILF

LIISSVASL
```

"Refractory" refers to a cancer that is not amendable to surgical intervention and is initially unresponsive to therapy.

"Relapsed" refers to a cancer that responded to treatment but then returns.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"T cell redirecting therapeutic" refers to a molecule containing two or more binding regions, wherein one of the binding regions specifically binds a cell surface antigen (such as a tumor associated antigen) on a target cell or tissue and wherein a second binding region of the molecule specifically binds a T cell antigen (such as, CD3). This dual/multi-target binding ability recruit T cells to the target cell or tissue leading to the eradication of the target cell or tissue.

"TMEFF2" refers to human transmembrane protein with EGF like and two follistatin like domains 2, also called tomoregulin 2. The amino acid sequence of the full length human TMEFF2 is shown in SEQ ID NO: 101. The extracellular domain of TMEFF2 spans residues 40-374 of SEQ ID NO: 101

```
TMEFF2
                                      (SEQ ID NO: 101)
MVLWESPRQCSSWTLCEGFCWLLLLPVMLLIVARPVKLAAFPTSLSDCQT

PTGWNCSGYDDRENDLFLCDTNTCKFDGECLRIGDTVTCVCQFKCNNDYV

PVCGSNGESYQNECYLRQAACKQQSEILVVSEGSCATDAGSGSGDGVHEG

SGETSQKETSTCDICQFGAECDEDAEDVWCVCNIDCSQTNFNPLCASDGK

SYDNACQIKEASCQKQEKIEVMSLGRCQDNTTTTTKSEDGHYARTDYAEN

ANKLEESAREHHIPCPEHYNGFCMHGKCEHSINMQEPSCRCDAGYTGQHC

EKKDYSVLYVVPGPVRFQYVLIAAVIGTIQIAVICVVVLCITRKCPRSNR

IHRQKQNTGHYSSDNTTRASTRLI
```

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene.

Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated. Antibody constant chain numbering can be found for example at ImMunoGeneTics website, at IMGT Web resources at IMGT Scientific charts.

The substitutions in the CH3 region are expressed as modified position(s) in the first CH3 domain of the first heavy chain/modified position(s) in the second CH3 domain of the second heavy chain. For example, F405L/K409R refers to a F405L mutation in the first CH3 region and K09R mutation in the second CH3 region. L351Y_ F405A_ Y407V/T394W refers to L351Y, F40FA and Y407V mutations in the first CH3 region and T394W mutation in the second CH3 region. D399FHKRQ/K409AGRH refers to mutation in which D399 may be replaced by F, H, K R or Q, and K409 may be replaced by A, G, R or H.

Conventional one and three-letter amino acid codes are used herein as shown in Table 1.

TABLE 1

| Amino acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

TABLE 1-continued

| Amino acid | Three-letter code | One-letter code |
|---|---|---|
| Proline | Pro | P |
| Serine | Ser | S |
| Threonine | Thr | T |
| Tryptophan | Trp | W |
| Tyrosine | Tyr | Y |
| Valine | Val | V |

Combinations of Anti-CD38 Antibodies and T Cell Redirecting Therapeutics and their Uses The invention is based, at least in part, on the finding that therapeutic agents JNJ-957 or a GPRC5DxCD3 antibody and the anti-CD38 antibody DARZALEX® (daratumumab), each of which mediate killing of multiple myeloma cells upon target engagement on the same cell did not antagonize each other in terms of competing to bind to or mechanism of action on MM cells or reciprocal downregulation of targets, and therefore are suitable to be used as a combination therapy. The invention is also based, at least in part, on the finding that prior treatment with DARZALEX® (daratumumab) augmented JNJ-957-mediated killing of multiple myeloma cells obtained from heavily treated relapsed/refractory multiple myeloma subjects. The invention is also based, at least in part, on the finding that DARZALEX® (daratumumab) augmented killing of tumor cells other than multiple myeloma cells by T cell redirecting therapeutics targeting non-multiple myeloma tumor cells. Hence combination of anti-CD38 antibodies with T cell redirecting therapeutics and/or pretreatment of subjects with anti-CD38 antibodies prior to administering T cell redirecting therapeutics can enhance anti-tumor efficacy of the monotherapies. Also given that cancers are typically heterogeneous diseases, portions of the cancer may exclusively have sufficient expression of one target vs. the other where combination therapy will aid deeper eradication of the disease.

CD38 is a multifunctional protein having function in receptor-mediated adhesion and signaling as well as mediating calcium mobilization via its ecto-enzymatic activity, catalyzing formation of cyclic ADP-ribose (cADPR) and ADPR. CD38 mediates cytokine secretion and activation and proliferation of lymphocytes (Funaro et al., J Immunol 145:2390-6, 1990; Terhorst et al., Cell 771-80, 1981; Guse et al., Nature 398:70-3, 1999). CD38, via its NAD glycohydrolase activity, also regulates extracellular NAD$^+$ levels, which have been implicated in modulating the regulatory T-cell compartment (Adriouch et al., Microbes infect 14:1284-92, 2012; Chiarugi et al., Nature Reviews 12:741-52, 2012). In addition to signaling via Ca$^{2+}$, CD38 signaling occurs via cross-talk with antigen-receptor complexes on T- and B-cells or other types of receptor complexes, e.g., MHC molecules, involving CD38 in several cellular responses, but also in switching and secretion of IgG1. It has been identified herein that an anti-CD38 antibody DARZALEX® (daratumumab) enhances the anti-tumor effect of T cell redirection therapeutics. While not wishing to be bound by any particular theory, it can be hypothesized that DARZALEX® (daratumumab) via its immunomodulatory activity in human subjects (i.e. reducing the number of immune suppressive Tregs, MDSCs and Bregs, increasing the number of CD8$^+$ T cells and the ratio of CD8$^+$ to Tregs, promoting CD8$^+$ central memory cell formation and increasing T cell clonality) may result in enhanced immune responses even in a subjects and therefore may facilitate T cell engagement of T cell redirecting therapeutics.

The disclosure provides a method of treating a cancer in a subject, comprising administering a therapeutically effective amount of an anti-CD38 antibody and a T cell redirecting therapeutic to the subject to treat the cancer.

The disclosure also provides a method of killing a tumor cell in a subject, comprising administering to the subject an anti-CD38 antibody and a T cell redirecting therapeutic that binds an antigen on the tumor cell for a time sufficient to kill the tumor cell.

The disclosure also provides a method of enhancing efficacy of a T cell redirecting therapeutic in a subject having a cancer, comprising administering to the subject an anti-CD38 antibody.

In some embodiments, the anti-CD38 antibody is administered prior to administering the T cell redirecting therapeutic.

The T cell redirecting therapeutic may be administered one day, two days, three days, four days, five days, six days, one week, two weeks, three weeks, one month, five weeks, six weeks, seven weeks, two months, three months, four months, five months, six months or longer prior to administering the anti-CD38 antibody.

In some embodiments, the T cell redirecting therapeutic binds an antigen on a tumor cell.

In some embodiments, the antigen on the tumor cell is BCMA, GPRC5D, CD33, CD123, CD19, PSMA, TMEFF2, CD20, CD10, CD21, CD22, CD25, CD30, CD34, CD37, CD44v6, CD45, CD52, CD133, ROR1, B7-H6, B7-H3, HM1.24, SLAMF7, Fms-like tyrosine kinase 3 (FLT-3, CD135), chondroitin sulfate proteoglycan 4 (CSPG4, melanoma-associated chondroitin sulfate proteoglycan), epidermal growth factor receptor (EGFR), Her2, Her3, IGFR, IL3R, fibroblast activating protein (FAP), CDCP1, Derlin1, Tenascin, frizzled 1-10, VEGFR2 (KDR/FLK1), VEGFR3 (FLT4, CD309), PDGFR-alpha (CD140a), PDGFR-beta (CD140b), endoglin, CLEC14, Tem1-8, or Tie2. Further exemplary antigens on the tumor cell include A33, CAMPATH-1 (CDw52), Carcinoembryonic antigen (CEA), Carboanhydrase IX (MN/CA IX), de2-7, EGFRvIII, EpCAM, Ep-CAM, folate-binding protein, G250, c-Kit (CD117), CSF1R (CD115), HLA-DR, IGFR, IL-2 receptor, IL3R, MCSP (melanoma-associated cell surface chondroitin sulphate proteoglycane), Muc-1, prostate stem cell antigen (PSCA), prostate specific antigen (PSA), hK2, TAG-72 or a tumor cell neoantigen.

In some embodiments, the T cell redirecting therapeutic binds BCMA, GPRC5D, CD33, CD123, CD19, PSMA, TMEFF2, CD20, CD22, CD25, CD52, ROR1, HM1.24, CD38 or SLAMF7.

In some embodiments, the T cell redirecting therapeutic binds CD3 epsilon (CD3ε).

In some embodiments, T cell redirecting therapeutic binds CD3.

In some embodiments, the T cell redirecting therapeutic binds CD8, KI2L4, NKG2E, NKG2D, NKG2F, BTNL3, CD186, BTNL8, PD-1, CD195, or NKG2C. These antigens are more specific to CD8$^+$ T cells when compared to CD3 (see e.g. Int. Pat. Publ. No. WO2018/187215).

In some embodiments, the T cell redirecting therapeutic comprises a CD3 binding domain comprising
a heavy chain complementarity determining region 1 (HCDR1) of SEQ ID NO: 33, a HCDR2 of SEQ ID NO: 34, a HCDR3 of SEQ ID NO: 35, a light chain complementarity determining region 1 (LCDR1) of SEQ ID NO: 36, a LCDR2 of SEQ ID NO: 37 and a LCDR3 of SEQ ID NO: 38;

a heavy chain variable region (VH) of SEQ ID NO: 39 and a light chain variable region (VL) of SEQ ID NO: 40;
the HCDR1 of SEQ ID NO: 74, the HCDR2 of SEQ ID NO: 75, the HCDR3 of SEQ ID NO: 76, the LCDR1 of SEQ ID NO: 77, the LCDR2 of SEQ ID NO: 78 and the LCDR3 of SEQ ID NO: 79;
the VH of SEQ ID NO: 80 and the VL of SEQ ID NO: 81;
the HCDR1, the HCDR2, the HCDR3, the LCDR1, the LCDR2 and the LCDR3 of a CD3 binding domain of SEQ ID NO: 53; or
the VH and the VL of the CD3 biding domain of SEQ ID NO: 53.

In some embodiments, the T cell redirecting therapeutic binds BCMA.

In some embodiments, the T cell redirecting therapeutic comprises a BCMA binding domain comprising the HCDR1 of SEQ ID NO: 23, the HCDR2 of SEQ ID NO: 24, the HCDR3 of SEQ ID NO: 25, the LCDR1 of SEQ ID NO: 26, the LCDR2 of SEQ ID NO: 27 and the LCDR3 of SEQ ID NO: 28, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38; and/or the BCMA binding domain comprising the VH of SEQ ID NO: 29 and the VL of SEQ ID NO: 30, and the CD3 biding domain comprising the VH of SEQ ID NO: 39 and the VL of SEQ ID NO: 40.

In some embodiments, the T cell redirecting therapeutic that binds BCMA comprises a first heavy chain (HC1) of SEQ ID NO: 31, a first light chain (LC1) of SEQ ID NO: 32, a second heavy chain (HC2) of SEQ ID NO: 41, and a second light chain (LC2) of SEQ ID NO: 42.

In some embodiments, the T cell redirecting therapeutic that binds BCMA comprises ACTR cancer therapy by Seattle Genetics, AFM-26, ALLO-715, anti-BCMA allogenic CAR-T cell therapy by CRISPR Therapeutics, anti-BCMA CAR-T therapy by Sorrento Therapeutics, anti-CD19/BCMA CAR-T cell therapy by Hrain Biotechnology, BCMA CAR-T therapy by Chineo Med (Beijing), BCMA TAC-T cell therapy by Triumvira Immunologics, BCMA-CAR T cell therapy by Shanghai Unicar-Therapy Biomed, BCMA/CD3 antibody by Regeneron, CAR-NK cell therapies by NantKwest, CC-93629, CMD-505, CTX-4419, CYAD-211, HDP-101, HPN-217, P-BCMA-ALLO1, TNB-383B, bb-2121, AUTO-2, BCMA chimaeric antigen receptor therapy by Pregene, BCMA-CAR T cells by Shanghai Bioray Laboratory, BCMA-CAR-T cells by CARsgen Therapeutics, CAR-T/TCR-T cell immunotherapy by Shenzhen BinDeBio, ET-140, P-BCMA-101, REGN-5458, AMG-701, anti BCMA CAR-T cell therapy by Cellular Biomedicine Group, bb-21217, BI-836909, CC-93269, Descartes-08, IM-21, JNJ-64007957, MEDI-2228 or PF-06863135.

In some embodiments, the T cell redirecting therapeutic comprises any one of BCMA binding domains described in Int. Pat. Publ. No. WO2017/031104.

In some embodiments, the T cell redirecting therapeutic binds GPRC5D.

In some embodiments, the T cell redirecting therapeutic comprises a GPRC5D binding domain comprising the HCDR1 of SEQ ID NO: 43, the HCDR2 of SEQ ID NO: 44, the HCDR3 of SEQ ID NO: 45, the LCDR1 of SEQ ID NO: 46, the LCDR2 of SEQ ID NO: 47 and the LCDR3 of SEQ ID NO: 48, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38; and/or the GPRC5D binding domain comprising the VH of SEQ ID NO: 49 and the VL of SEQ ID NO: 50, and the CD3 biding domain comprising the VH of SEQ ID NO: 39 and the VL of SEQ ID NO 40.

In some embodiments, the T cell redirecting therapeutic that binds GPRC5D comprises the HC1 of SEQ ID NO: 51, the LC1 of SEQ ID NO: 52, the HC2 of SEQ ID NO: 41, and the LC2 of SEQ ID NO: 42.

In some embodiments, the T cell redirecting therapeutic comprises GPRC5D antibodies by Eureka Therapeutics.

In some embodiments, the T cell redirecting therapeutic comprises any one of GPRC5D binding domains described in Int. Pat. Publ. No. WO2018/0037651.

In some embodiments, the T cell redirecting therapeutic binds CD33.

In some embodiments, the T cell redirecting therapeutic comprises a CD33 binding domain comprising the HCDR1 of SEQ ID NO: 84, the HCDR2 of SEQ ID NO: 85, the HCDR3 of SEQ ID NO: 86, the LCDR1 of SEQ ID NO: 87, the LCDR2 of SEQ ID NO: 88 and the LCDR3 of SEQ ID NO: 89, and a CD3 binding domain comprising the HCDR1 of SEQ ID NO: 74, the HCDR2 of SEQ ID NO: 75, the HCDR3 or SEQ ID NO: 76, the LCDR1 or SEQ ID NO: 77, the LCDR2 or SEQ ID NO: 78 and the LCDR3 of SEQ ID NO: 79; and/or the CD33 binding domain comprising the VH of SEQ ID NO: 90 and the VL of SEQ ID NO: 91, and the CD3 biding domain comprising the VH of SEQ ID NO: 80 and the VL of SEQ ID NO: 81.

In some embodiments, the T cell redirecting therapeutic that binds CD33 comprises the HC1 of SEQ ID NO: 92, the LC1 of SEQ ID NO: 93, the HC2 of SEQ ID NO: 82 and the LC2 of SEQ ID NO: 83.

In some embodiments, the T cell redirecting therapeutic that binds CD33 comprises CAR-T/TCR-T cell immunotherapy by Shenzhen BinDeBio, AMG-330, AMV-564, JNJ-67571244, ICG-144, AMG-673, CD33 CAR-T therapy-INXN 3004 by, Ziopharm, huCD33-BsAb, VOR-33, HMBD-004A, GEM-333, TGB-3550 or CD33.taNK.

In some embodiments, the T cell redirecting therapeutic binds CD123.

In some embodiments, the T cell redirecting therapeutic comprises a CD123 binding domain comprising the HCDR1 of SEQ ID NO: 94, the HCDR2 of SEQ ID NO: 95, the HCDR3 of SEQ ID NO: 96, the LCDR1 of SEQ ID NO: 9, the LCDR2 of SEQ ID NO: 10, and the LCDR3 of SEQ ID NO: 59, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38; and/or the CD123 binding domain comprising the VH of SEQ ID NO: 100 and the VL of SEQ ID NO: 61, and the CD3 biding domain comprising the VH of SEQ ID NO: 39 and the VL of SEQ ID NO: 40.

In some embodiments, the T cell redirecting therapeutic that binds CD123 comprises the HC1 of SEQ ID NO: 102, the LC1 of SEQ ID NO: 63, the HC2 of SEQ ID NO: 41 and the LC2 of SEQ ID NO: 42.

In some embodiments, the T cell redirecting therapeutic that binds CD123 comprises acute myeloid leukaemia therapy by TheraVectys, APVO-437, anti-CD123 CAR-T cell therapy by Nanjing Legend Biotech, APVO-436, CD123 CAR-T cell therapy by Hebei Senlang Biotechnology, flotetuzumab, IM-23, JNJ-63709178, MB-102 by Mustang Bio, UCART-123, XmAb-14045 or CD3-CD123 bispecific T-cell engager by Sanofi.

In some embodiments, the T cell redirecting therapeutic comprises any one of CD123 binding domains described in Int. Pat. Publ. No. WO2016/036937.

In some embodiments, the T cell redirecting therapeutic binds CD19.

In some embodiments, the T cell redirecting therapeutic comprises a CD19 binding domain comprising the HCDR1, the HCDR2, the HCDR3, the LCDR1, the LCDR2 and the LCDR3 of the CD19 binding domain of SEQ ID NO: 53 and a CD3 binding domain comprising the HCDR1, the HCDR2, the HCDR3, the LCDR1, the LCDR2 and the LCDR3 of the CD3 binding domain of SEQ ID NO 53; and/or the amino acid sequence of SEQ ID NO: 53.

In some embodiments, the T cell redirecting therapeutic that binds CD19 comprises axicabtagene ciloleucel, blinatumomab, tisagenlecleucel-t, AMG-562, AUTO-1 CAR-T CD19 by Cellular Biomedicine Group, CD19 chimeric antigen receptor T-cell therapy by Ziopharm, CD19-CAR-T cell therapy by ioceltech Therapeutics, CD19-CAR-T cell therapy by Marino Biotechnology, CD19-CAR-T2 cell therapy by Guangdong Zhaotai InVivo, CD19/4-1BBL armored CART cell therapy by Juno Therapeutics, CSG-CD19, DI-B4, ET-190, GC-007F, GC-022, human CD19 T cell therapy by HRAIN Biotechnology, humanized anti-CD19 Control CAR (3rd Gen) by Kite Pharma, ICAR-19 CAR-T cells by Immune Cell Therapy, ICTCAR-003, iPD1 CD19 eCAR T cells by Marino Biotechnology, JWCAR029, PTG-01, PZ01, Sen1_1904 A, Sen1_1904B, UCART-19, UWC-19, AUTO-3, BinD-19, CAR-T cell therapy by Shanghai Unicar-Therapy Biomed, CAR-T/TCR-T cell immunotherapy by Shenzhen BinDeBio, CD-19 CAR-T cell therapy by Miltenyi Biotec, CD19 CAR-T cells by Shanghai Unicar-Therapy Biomed, CD19-CAR T cell therapy by Takara Bio, CD19-CART by Shanghai Bioray Laboratory, CD19-targeted chimeric antigen receptor T-cells by Sinobioway, CD19/CD20 CAR-T cell therapy by Shanghai Longyao Biotechnology, CIK-CAR.CD19, ICTCAR-011, IM-19, JCAR-014, loncastuximab tesirine, MB-CART2019.1, OXS-1550, PBCAR-0191, PCAR-019, PCAR-119, Sen1-001, TI-1007, XmAb-5871, inebilizumab, lisocabtagene maraleucel, XmAb-5574, 3rd generation CD19-CART cells+mbIL15 by Eden BioCell, A-329, ALLO-501, anti-CD19 anti-CD20 Bispecific CAR redirected autologous T-cells by Beijing Doing Biomedical Co, anti-CD19 CAR NK cell therapy, by Allife Medical Science. anti-CD19/BCMA CAR-T cell therapy by Hrain Biotechnology ATA-2431, ATA-3219. AVA-008. CD19 CAR-T cell therapy by Celularity, CD19 chimeric antigen receptor T-cell therapy, 3rd generation by Ziopharm, CD19 dBiTE by Inovio, CD19 TCR-cell therapy by Bellicum, CD19-ATAC by Wilex, CD19/20 CAR-T therapy by Chineo Med (Beijing), CD19/CD22 dual targeting therapy by Eureka Therapeutics, chimeric antigen receptor T cell (CAR-T) therapies by Helix BioPharma, CMD-502, CTX-110, CYAD-04, CYAD-221, ET-019002, FT-596, FT-819, gamma-delta CAR-T therapy by TC Biopharm, ICTCAR-014, iDD-002, KITE-037, NI-2201, RB-1916, Sen1_002, TAC01-CD19, TC-110, TC-310, TCB-003 or TI-7007.

In some embodiments, the T cell redirecting therapeutic binds PSMA.

In some embodiments, the T cell redirecting therapeutic comprises a PSMA binding domain comprising the HCDR1 of SEQ ID NO: 54, the HCDR2 or SEQ ID NO: 55, the HCDR3 or SEQ ID NO: 56, the LCDR1 or SEQ ID NO: 9, the LCDR2 or SEQ ID NO: 10 and the LCDR3 of SEQ ID NO: 59, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38; and/or the PSMA binding domain comprising the VH of SEQ ID NO: 60 and the VL of SEQ ID NO: 61, and the CD3 biding domain comprising the VH of SEQ ID NO: 39 and the VL of SEQ ID NO: 40.

In some embodiments, the T cell redirecting therapeutic that binds PSMA comprises the HC1 of SEQ ID NO: 62, the LC1 of SEQ ID NO: 63, the HC2 of SEQ ID NO: 41 and the LC2 of SEQ ID NO: 42.

In some embodiments, the T cell redirecting therapeutic binds TMEFF2.

In some embodiments, the T cell redirecting therapeutic comprises a TMEFF2 binding domain comprising the HCDR1 of SEQ ID NO: 64, the HCDR2 of SEQ ID NO: 65, the HCDR3 of SEQ ID NO: 66, the LCDR1 of SEQ ID NO: 67, the LCDR2 of SEQ ID NO: 68 and the LCDR3 of SEQ ID NO: 69, and a CD3 binding domain comprising the HCDR1 of SEQ ID NO: 74, the HCDR2 of SEQ ID NO: 75, the HCDR3 or SEQ ID NO: 76, the LCDR1 or SEQ ID NO: 77, the LCDR2 or SEQ ID NO: 78 and the LCDR3 of SEQ ID NO: 79; and/or the TMEFF2 binding domain comprising the VH of SEQ ID NO: 70 and the VL of SEQ ID NO: 71, and the CD3 biding domain comprising the VH of SEQ ID NO: 80 and the VL of SEQ ID NO: 81.

In some embodiments, the T-cell redirecting therapeutic that binds TMEFF2 comprises the HC1 of SEQ ID NO: 72, the LC1 of SEQ ID NO: 73, the HC2 of SEQ ID NO: 82 and the LC2 of SEQ ID NO: 83.

In some embodiments, the T cell redirecting therapeutic binds CD20.

In some embodiments, the T cell redirecting therapeutic binds CD22.

In some embodiments, the T cell redirecting therapeutic binds CD25.

In some embodiments, the T cell redirecting therapeutic binds CD52.

In some embodiments, the T cell redirecting therapeutic binds ROR1.

In some embodiments, the T cell redirecting therapeutic binds HM1.24.

In some embodiments, the T cell redirecting therapeutic binds SLAMF7.

In some embodiments, the T cell redirecting therapeutic is a multispecific antibody, a chimeric antigen receptor (CAR), or a T cell comprising the CAR.

In some embodiments, the T cell redirecting therapeutic is the CAR.

In some embodiments, the T cell redirecting therapeutic is the T cell expressing the CAR.

In some embodiments, the T cell redirecting therapeutic is the multispecific antibody.

In some embodiments, the multispecific antibody is an IgG1, an IgG2, an IgG3 or an IgG4 isotype.

In some embodiments, the multispecific antibody is an IgG1 isotype.

In some embodiments, the multispecific antibody is an IgG2 isotype.

In some embodiments, the multispecific antibody is an IgG3 isotype.

In some embodiments, the multispecific antibody is an IgG4 isotype.

The multispecific antibody may be of any allotype. It is expected that allotype has no influence on properties of the multispecific antibodies, such as binding or Fc-mediated effector functions Immunogenicity of therapeutic antibodies is associated with increased risk of infusion reactions and decreased duration of therapeutic response (Baert et al., (2003) N Engl J Med 348:602-08). The extent to which therapeutic antibodies induce an immune response in the host may be determined in part by the allotype of the antibody (Stickler et al., (2011) Genes and Immunity 12:213-21). Antibody allotype is related to amino acid sequence variations at specific locations in the constant region sequences of the antibody. Table 2 shows select IgG1, IgG2 and IgG4 allotypes.

TABLE 2

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n) | T | M | | | | | | |
| G2m(n-) | P | V | | | | | | |
| G2m(n)/(n-) | T | V | | | | | | |
| nG4m(a) | | | L | R | | | | |
| G1m(17) | | | | | K | E | M | A |
| G1m(17,1) | | | | | K | D | L | A |

In some embodiments, the multispecific antibody comprises one or more Fc substitutions that reduces binding of the multispecific antibody to a Fcγ receptor (FcγR). Substitutions that reduce binding of the multispecific antibody to the FcγR reduces the Fc effector functions such as ADCC, ADCP and/or CDC of the multispecific antibody. The specific substitutions may be made in comparison to the wild-type IgG1 of SEQ ID NO: 103 or the wild-type IgG4 of SEQ ID NO: 104.

In some embodiments, the one or more Fc substitutions is selected from the group consisting of F234A/L235A on IgG4, L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4 and S228P/F234A/L235A/G236-deleted/G237A/P238S on IgG4, wherein residue numbering is according to the EU index.

In some embodiments, the one or more Fc substitutions is F234A/L235A on IgG4.

In some embodiments, the one or more Fc substitutions is L234A/L235A on IgG1.

In some embodiments, the one or more Fc substitutions is V234A/G237A/P238S/H268A/V309L/A330S/P331S on IgG2.

In some embodiments, the one or more Fc substitutions is F234A/L235A on IgG4.

In some embodiments, the one or more Fc substitutions is S228P/F234A/L235A on IgG4.

In some embodiments, the one or more Fc substitutions is N297A on all Ig isotypes.

In some embodiments, the one or more Fc substitutions is V234A/G237A on IgG2.

In some embodiments, the one or more Fc substitutions is K214T/E233P/L234V/L235A/G236-deleted/A327G/P331A/D365E/L358M on IgG1.

In some embodiments, the one or more Fc substitutions is H268Q/V309L/A330S/P331S on IgG2.

In some embodiments, the one or more Fc substitutions is S267E/L328F on IgG1. In some embodiments, the one or more Fc substitutions is L234F/L235E/D265A on IgG1.

In some embodiments, the one or more Fc substitutions is L234A/L235A/G237A/P238S/H268A/A330S/P331S on IgG1.

In some embodiments, the one or more Fc substitutions is S228P/F234A/L235A/G237A/P238S on IgG4 and S228P/F234A/L235A/G236-deleted/G237A/P238S on IgG4.

In some embodiments, the multispecific antibody further comprises a S228P substitution.

In some embodiments, the multispecific antibody comprises one or more asymmetric substitutions in a first CH3 domain or in a second CH3 domain, or in both the first CH3 domain and the second CH3 domain.

In some embodiments, the one or more asymmetric substitutions is selected from the group consisting of F450L/K409R, wild-type/F409L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

In some embodiments, the one or more asymmetric substitutions is F450L/K409R.

In some embodiments, the one or more asymmetric substitutions is wild-type/F409L_R409K.

In some embodiments, the one or more asymmetric substitutions is T366Y/F405A.

In some embodiments, the one or more asymmetric substitutions is T366W/F405W.

In some embodiments, the one or more asymmetric substitutions is F405W/Y407A.

In some embodiments, the one or more asymmetric substitutions is T394W/Y407T.

In some embodiments, the one or more asymmetric substitutions is T394S/Y407A.

In some embodiments, the one or more asymmetric substitutions is T366W/T394S.

In some embodiments, the one or more asymmetric substitutions is F405W/T394S.

In some embodiments, the one or more asymmetric substitutions is T366W/T366S_L368A_Y407V.

In some embodiments, the one or more asymmetric substitutions is L351Y_F405A_Y407V/T394W.

In some embodiments, the one or more asymmetric substitutions is T366I_K392M_T394W/F405A_Y407V.

In some embodiments, the one or more asymmetric substitutions is T366L_K392M_T394W/F405A_Y407V.

In some embodiments, the one or more asymmetric substitutions is L351Y_Y407A/T366A_K409F.

In some embodiments, the one or more asymmetric substitutions is L351Y_Y407A/T366V_K409F.

In some embodiments, the one or more asymmetric substitutions is Y407A/T366A_K409F.

In some embodiments, the one or more asymmetric substitutions is T350V_L351Y_F405A_Y407V/T350V_T366L_K392L_T394W.

In some embodiments, the cancer is a hematological malignancy or a solid tumor.

In some embodiments, the hematological malignancy is a multiple myeloma, a smoldering multiple myeloma, a monoclonal gammopathy of undetermined significance (MGUS), an acute lymphoblastic leukemia (ALL), a diffuse large B-cell lymphoma (DLBCL), a Burkitt's lymphoma (BL), a follicular lymphoma (FL), a mantle-cell lymphoma (MCL), Waldenstrom's macroglobulinema, a plasma cell leukemia, a light chain amyloidosis (AL), a precursor B-cell lymphoblastic leukemia, a precursor B-cell lymphoblastic leukemia, an acute myeloid leukemia (AML), a myelodysplastic syndrome (MDS), a chronic lymphocytic leukemia (CLL), a B cell malignancy, a chronic myeloid leukemia (CML), a hairy cell leukemia (HCL), a blastic plasmacytoid dendritic cell neoplasm, Hodgkin's lymphoma, non-Hodgkin's lymphoma, a marginal zone B-cell lymphoma (MZL), a mucosa-associated lymphatic tissue lymphoma (MALT), plasma cell leukemia, anaplastic large-cell lymphoma (ALCL), leukemia or lymphoma.

In some embodiments, the hematological malignancy is the multiple myeloma.

In some embodiments, the multiple myeloma is a newly diagnosed multiple myeloma.

In some embodiments, the multiple myeloma is a relapsed or a refractory multiple myeloma.

In some embodiments, the multiple myeloma is a high-risk multiple myeloma. Subjects with high-risk multiple myeloma are known to relapse early and have poor prognosis and outcome. Subjects can be classified as having high-risk multiple myeloma is they have one or more of the following cytogenetic abnormalities: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p, or t(4;14)(p16;q32), t(14;16)(q32;q23) and del17p.

In some embodiments, the subject having the high-risk multiple myeloma has one or more chromosomal abnormalities comprising: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p; or t(4;14)(p16;q32), t(14;16)(q32;q23) and del17p, or any combination thereof.

Various qualitative and/or quantitative methods may be used to determine relapse or refractory nature of the disease. Symptoms that may be associated are for example a decline or plateau of the well-being of the patient or re-establishment or worsening of various symptoms associated with solid tumors, and/or the spread of cancerous cells in the body from one location to other organs, tissues or cells.

The cytogenetic abnormalities can be detected for example by fluorescent in situ hybridization (FISH). In chromosomal translocations, an oncogene is translocated to the IgH region on chromosome 14q32, resulting in dysregulation of these genes. t(4;14)(p16;q32) involves translocation of fibroblast growth factor receptor 3 (FGFR3) and multiple myeloma SET domain containing protein (MM-SET) (also called WHSC1/NSD2), and t(14;16)(q32;q23) involves translocation of the MAF transcription factor C-MAF. Deletion of 17p (del17p) involves loss of the p53 gene locus.

In some embodiments, the multiple myeloma is relapsed or refractory to treatment with the anti-CD38 antibody, lenalinomide, bortezomib, pomalidomide, carfilzomib, elotozumab, ixazomib, melphalan or thalidomide, or any combination thereof.

In some embodiments, the multiple myeloma is relapsed or refractory to treatment with the anti-CD38 antibody. In some embodiments, the multiple myeloma is relapsed or refractory to treatment with lenalinomide. In some embodiments, the multiple myeloma is relapsed or refractory to treatment with bortezomib. In some embodiments, the multiple myeloma is relapsed or refractory to treatment with pomalidomide. In some embodiments, the multiple myeloma is relapsed or refractory to treatment with carfilzomib. In some embodiments, the multiple myeloma is relapsed or refractory to treatment with elotozumab. In some embodiments, the multiple myeloma is relapsed or refractory to treatment with ixazomib. In some embodiments, the multiple myeloma is relapsed or refractory to treatment with melphalan. In some embodiments, the multiple myeloma is relapsed or refractory to treatment with or thalidomide.

In some embodiments, the hematological malignancy is the AML.

In some embodiments, the AML is AML with at least one genetic abnormality, AML with multilineage dysplasia, therapy-related AML, undifferentiated AML, AML with minimal maturation, AML with maturation, acute myelomonocytic leukemia, acute monocytic leukemia, acute erythroid leukemia, acute megakaryoblastic leukemia, acute basophilic leukemia, acute panmyelosis with fibrosis or myeloid sarcoma.

In some embodiments, the AML is AML with at least one genetic abnormality. In some embodiments, the AML is AML with multilineage dysplasia. In some embodiments, the AML is therapy-related AML. In some embodiments, the AML is undifferentiated AML. In some embodiments, the AML is AML with minimal maturation. In some embodiments, the AML is AML with maturation. In some embodiments, the AML is acute myelomonocytic leukemia. In some embodiments, the AML is acute monocytic leukemia. In some embodiments, the AML is acute erythroid leukemia. In some embodiments, the AML is acute megakaryoblastic leukemia. In some embodiments, the AML is acute basophilic leukemia. In some embodiments, the AML is acute panmyelosis with fibrosis. In some embodiments, the AML is myeloid sarcoma.

In some embodiments, the at least one genetic abnormality is a translocation between chromosomes 8 and 21, a translocation or an inversion in chromosome 16, a translocation between chromosomes 15 and 17, changes in chromosome 11, or mutation in fms-related tyrosine kinase 3 (FLT3), nucleophosmin (NPM1), isocitrate dehydrogenase 1 (IDH1), isocitrate dehydrogenase 2 (IDH2), DNA (cytosine-5)-methyltransferase 3 (DNMT3A), CCAAT/enhancer binding protein alpha (CEBPA), U2 small nuclear RNA auxiliary factor 1 (U2AF1), enhancer of zeste 2 polycomb repressive complex 2 subunit (EZH2), structural maintenance of chromosomes 1A (SMC1A) or structural maintenance of chromosomes 3 (SMC3).

In some embodiments, the at least one genetic abnormality is the translocation between chromosomes 8 and 21. In some embodiments, the at least one genetic abnormality is the translocation or an inversion in chromosome 16. In some embodiments, the at least one genetic abnormality is the translocation between chromosomes 15 and 17. In some embodiments, the at least one genetic abnormality is changes in chromosome 11. In some embodiments, the at least one genetic abnormality is the mutation in fms-related tyrosine kinase 3 (FLT3). In some embodiments, the at least one genetic abnormality is the mutation in nucleophosmin (NPM1). In some embodiments, the at least one genetic abnormality is the mutation in isocitrate dehydrogenase 1 (IDH1). In some embodiments, the at least one genetic abnormality is the mutation in isocitrate dehydrogenase 2 (IDH2). In some embodiments, the at least one genetic abnormality is the mutation in DNA (cytosine-5)-methyltransferase 3 (DNMT3A). In some embodiments, the at least one genetic abnormality is the mutation in CCAAT/enhancer binding protein alpha (CEBPA). In some embodiments, the at least one genetic abnormality is the mutation in U2 small nuclear RNA auxiliary factor 1 (U2AF1). In some embodiments, the at least one genetic abnormality is the mutation in enhancer of zeste 2 polycomb repressive complex 2 subunit (EZH2). In some embodiments, the at least one genetic abnormality is the mutation in structural maintenance of chromosomes 1A (SMC1A). In some embodiments, the at least one genetic abnormality is the mutation in structural maintenance of chromosomes 3 (SMC3).

In some embodiments, the at least one genetic abnormality is a translocation t(8; 21)(q22; q22), an inversion inv(16)(p13; q22), a translocation t(16; 16)(p13; q22), a translocation t(15; 17)(q22; q12), a mutation FLT3-ITD, mutations R132H or R100Q/R104V/F108L/R119Q/I130V in IDH1 or mutations R140Q or R172 in IDH2.

In some embodiments, the at least one genetic abnormality is the translocation t(8; 21)(q22; q22). In some embodiments, the at least one genetic abnormality is the inversion inv(16)(p13; q22). In some embodiments, the at least one genetic abnormality is the translocation t(16; 16)(p13; q22). In some embodiments, the at least one genetic abnormality is the translocation t(15; 17)(q22; q12). In some embodiments, the at least one genetic abnormality is the mutation FLT3-ITD. In some embodiments, the at least one genetic abnormality is the mutation R132H in IDH1. In some embodiments, the at least one genetic abnormality is the mutation R100Q/R104V/F108L/R119Q/I130V in IDH1. In some embodiments, the at least one genetic abnormality is the mutation R140Q in IDH2. In some embodiments, the at least one genetic abnormality is the mutation R172 in IDH2.

In some embodiments, the hematological malignancy is the ALL.

In some embodiments, the ALL is B-cell lineage ALL, T-cell lineage ALL, adult ALL or pediatric ALL.

In some embodiments, the ALL is B-cell lineage ALL. In some embodiments, the ALL is T-cell lineage ALL. In some embodiments, the ALL is adult ALL. In some embodiments, the ALL is pediatric ALL.

In some embodiments, the subject with ALL has a Philadelphia chromosome or is resistant or has acquired resistance to treatment with a BCR-ABL kinase inhibitor.

In some embodiments, the subject with ALL has the Philadelphia chromosome. In some embodiments, the subject with ALL is resistant or has acquired resistance to treatment with a BCR-ABL kinase inhibitor.

The Ph chromosome is present in about 20% of adults with ALL and a small percentage of children with ALL and is associated with poor prognosis. At a time of relapse, patients with Ph+ positive ALL may be on tyrosine kinase inhibitor (TKI) regimen and may have therefore become resistant to the TKI. The anti-CD38 antibodies may thus be administered to a subject who has become resistant to selective or partially selective BCR-ABL inhibitors. Exemplary BCR-ABL inhibitors are for example imatinib, dasatinib, nilotinib, bosutinib, ponatinib, bafetinib, saracatinib, tozasertib or danusertib.

Other chromosomal rearrangements identified in B-lineage ALL patients are t(v;11q23) (MLL rearranged), t(1;19)(q23;p13.3); TCF3-PBX1 (E2A-PBX1), t(12;21)(p13;q22); ETV6-RUNX1 (TEL-AML1) and t(5;14)(q31;q32); IL3-IGH.

In some embodiments, the subject has ALL with t(v; 11q23) (MLL rearranged), t(1;19)(q23;p13.3); TCF3-PBX1 (E2A-PBX1), t(12;21)(p13;q22); ETV6-RUNX1 (TEL-AML1) or t(5;14)(q31;q32); IL3-IGH chromosomal rearrangement.

Chromosomal rearrangements can be identified using well known methods, for example fluorescent in situ hybridization, karyotyping, pulsed field gel electrophoresis, or sequencing.

In some embodiments, the hematological malignancy is the smoldering multiple myeloma.

In some embodiments, the hematological malignancy is the MGUS.

In some embodiments, the hematological malignancy is the ALL.

In some embodiments, the hematological malignancy is the DLBLC.

In some embodiments, the hematological malignancy is the BL.

In some embodiments, the hematological malignancy is the FL.

In some embodiments, the hematological malignancy is the MCL.

In some embodiments, the hematological malignancy is Waldenstrom's macroglobulinema.

In some embodiments, the hematological malignancy is the plasma cell leukemia.

In some embodiments, the hematological malignancy is the AL.

In some embodiments, the hematological malignancy is the precursor B-cell lymphoblastic leukemia.

In some embodiments, the hematological malignancy is the precursor B-cell lymphoblastic leukemia.

In some embodiments, the hematological malignancy is the myelodysplastic syndrome (MDS).

In some embodiments, the hematological malignancy is the CLL.

In some embodiments, the hematological malignancy is the B cell malignancy.

In some embodiments, the hematological malignancy is the CML.

In some embodiments, the hematological malignancy is the HCL.

In some embodiments, the hematological malignancy is the blastic plasmacytoid dendritic cell neoplasm.

In some embodiments, the hematological malignancy is Hodgkin's lymphoma.

In some embodiments, the hematological malignancy is non-Hodgkin's lymphoma.

In some embodiments, the hematological malignancy is the MZL.

In some embodiments, the hematological malignancy is the MALT.

In some embodiments, the hematological malignancy is the plasma cell leukemia.

In some embodiments, the hematological malignancy is the ALCL.

In some embodiments, the hematological malignancy is leukemia.

In some embodiments, the hematological malignancy is lymphoma.

In some embodiments, the solid tumor is a prostate cancer, a lung cancer, a non-small cell lung cancer (NSCLC), a liver cancer, a cervical cancer, a colon cancer, a breast cancer, an ovarian cancer, an endometrial cancer, a pancreatic cancer, a melanoma, an esophageal cancer, a gastric cancer, a stomach cancer, a renal carcinoma, a bladder cancer, a hepatocellular carcinoma, a renal cell carcinoma, an urothelial carcinoma, a head and neck cancer, a glioma, a glioblastoma, a colorectal cancer, a thyroid cancer, epithelial cancers, adenocarcinomas or advanced solid tumors.

In some embodiments, the solid tumor is the prostate cancer.

In some embodiments, the solid tumor is the lung cancer.

In some embodiments, the solid tumor is the non-small cell lung cancer (NSCLC).

In some embodiments, the solid tumor is the liver cancer.

In some embodiments, the solid tumor is the cervical cancer.

In some embodiments, the solid tumor is the colon cancer.

In some embodiments, the solid tumor is the breast cancer.

In some embodiments, the solid tumor is the ovarian cancer.

In some embodiments, the solid tumor is the endometrial cancer.

In some embodiments, the solid tumor is the pancreatic cancer.

In some embodiments, the solid tumor is the melanoma.

In some embodiments, the solid tumor is the esophageal cancer.

In some embodiments, the solid tumor is the gastric cancer.

In some embodiments, the solid tumor is the stomach cancer.

In some embodiments, the solid tumor is the renal carcinoma.

In some embodiments, the solid tumor is the bladder cancer.

In some embodiments, the solid tumor is the hepatocellular carcinoma.

In some embodiments, the solid tumor is the renal cell carcinoma.

In some embodiments, the solid tumor is the urothelial carcinoma.

In some embodiments, the solid tumor is the head and neck cancer.

In some embodiments, the solid tumor is the glioma.

In some embodiments, the solid tumor is the glioblastoma.

In some embodiments, the solid tumor is the colorectal cancer.

In some embodiments, the solid tumor is the thyroid cancer.

In some embodiments, the solid tumor is epithelial cancers.

In some embodiments, the solid tumor is adenocarcinomas.

In some embodiments, the solid tumor is advanced solid tumors.

In some embodiments, the prostate cancer is a relapsed, a refractory, a malignant or a castration resistant prostate cancer, or any combination thereof.

In some embodiments, the prostate cancer is a relapsed prostate cancer. In some embodiments, the prostate cancer is a refractory prostate cancer. In some embodiments, the prostate cancer is a malignant prostate cancer. In some embodiments, the prostate cancer is a castration resistant prostate cancer.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody is an IgG1 isotype.

In some embodiments, the anti-CD38 antibody comprises the HC of SEQ ID NO: 12 and the LC of SEQ ID NO: 13.

Other anti-CD38 antibodies used in the methods of the invention may be known antibodies, such as mAb003 comprising the VH and the VL sequences of SEQ ID NOs: 14 and 15, respectively and described in U.S. Pat. No. 7,829,673. The VH and the VL of mAb003 may be expressed as IgG1/κ; mAb024 comprising the VH and the VL sequences of SEQ ID NOs: 16 and 17, respectively, described in U.S. Pat. No. 7,829,673. The VH and the VL of mAb024 may be expressed as IgG1/κ; MOR-202 (MOR-03087) comprising the VH and the VL sequences of SEQ ID NOs: 18 and 19, respectively, described in U.S. Pat. No. 8,088,896. The VH and the VL of MOR-202 may be expressed as IgG1/κ; or isatuximab; comprising the VH and the VL sequences of SEQ ID NOs: 20 and 21, respectively, described in U.S. Pat. No. 8,153,765. The VH and the VL of Isatuximab may be expressed as IgG1/κ.

```
(Daratumumab VH)
SEQ ID NO: 4
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSS (Daratumumab VL)
SEQ ID NO: 5
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIK (Daratumumab HCDR1)
SEQ ID NO: 6
SFAMS (Daratumumab HCDR2)
SEQ ID NO: 7
AISGSGGGTYYADSVKG (Daratumumab HCDR3)
SEQ ID NO: 8
DKILWFGEPVFDY (Daratumumab LCDR1)
SEQ ID NO: 9
RASQSVSSYLA (Daratumumab LCDR2)
SEQ ID NO: 10
DASNRAT (Daratumumab LCDR3)
SEQ ID NO: 11
QQRSNWPPTF (Daratumumab HC)
SEQ ID NO: 12
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE
```

-continued

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK (Daratumumab LC)
SEQ ID NO: 13
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 14
QVQLVQSGAEVKKPGSSVKVSCKASGGTFSSYAFSWVRQAPGQGLEWMGR

VIPFLGIANSAQKFQGRVTITADKSTSTAYMDLSSLRSEDTAVYYCARDD

IAALGPFDYWGQGTLVTVSSAS

SEQ ID NO: 15
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPRTFGQ

GTKVEIK

SEQ ID NO: 16
EVQLVQSGAEVKKPGESLKISCKGSGYSFSNYWIGWVRQMPGKGLEWMGI

IYPHDSDARYSPSFQGQVTFSADKSISTAYLQWSSLKASDTAMYYCARHV

GWGSRYWYFDLWGRGTLVTVSS

SEQ ID NO: 17
EIVLTQSPATLSLSPGERATLSCRASQSVSSYLAWYQQKPGQAPGLLIYD

ASNRASGIPARFSGSGSGTDFTLTISSLEPEDFAVYYCQQRSNWPLTFGG

GTKVEIK

SEQ ID NO: 18
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS

SEQ ID NO: 19
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ

SEQ ID NO 20:
QVQLVQSGAEVAKPGTSVKLSCKASGYTFTDYWMQWVKQRPGQGLEWIGT

IYPGDGDTGYAQKFQGKATLTADKSSKTVYMHLSSLASEDSAVYYCARGD

YYGSNSLDYWGQGTSVTVSS

SEQ ID NO: 21:
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIK

In some embodiments, the anti-CD38 antibody comprises the VH of SEQ ID NO: 14 and the VL of SEQ ID NO: 15; the VH of SEQ ID NO: 16 and the VL of SEQ ID NO: 17; the VH of SEQ ID NO: 18 and the VL of SEQ ID NO: 19; or the VH of SEQ ID NO: 20 and the VL of SEQ ID NO: 21.

In some embodiments, the anti-CD38 antibody is an IgG1 isotype.

In some embodiments, the T-cell redirecting therapeutic is a BCMAxCD3 bispecific antibody, a GPRC5DxCD3 bispecific antibody, a CD33xCD3 bispecific antibody, a CD19xCD3 bispecific antibody, a CD123xCD3 bispecific antibody, a PSMAxCD3 bispecific antibody, or a TMEFF2xCD3 bispecific antibody.

In some embodiments, the T-cell redirecting therapeutic is the BCMAxCD3 bispecific antibody.

In some embodiments, the T-cell redirecting therapeutic is the GPRC5DxCD3 bispecific antibody.

In some embodiments, the T-cell redirecting therapeutic is the CD33xCD3 bispecific antibody, In some embodiments, the T-cell redirecting therapeutic is the CD19xCD3 bispecific antibody.

In some embodiments, the T-cell redirecting therapeutic is the CD123xCD3 bispecific antibody.

In some embodiments, the T-cell redirecting therapeutic is the PSMAxCD3 bispecific antibody.

In some embodiments, the T-cell redirecting therapeutic is the TMEFF2xCD3 bispecific antibody.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is the autologous stem cell transplant (ASCT). In some embodiments, the one or more anti-cancer therapies is radiation. In some embodiments, the one or more anti-cancer therapies is surgery. In some embodiments, the one or more anti-cancer therapies is the chemotherapeutic agent. In some embodiments, the one or more anti-cancer therapies is the immunomodulatory agent. In some embodiments, the one or more anti-cancer therapies is targeted cancer therapy.

In some embodiments, the one or more anti-cancer therapies is selected from the group consisting of lenalidomide, thalidomide, pomalidomide, bortezomib, carfilzomib, elotozumab, ixazomib, melphalan, dexamethasone, vincristine, cyclophosphamide, hydroxy daunorubicin, prednisone, rituximab, imatinib, dasatinib, nilotinib, bosutinib, ponatinib, bafetinib, saracatinib, tozasertib or danusertib, cytarabine, daunorubicin, idarubicin, mitoxantrone, hydroxyurea, decitabine, cladribine, fludarabine, topotecan, etoposide 6-thioguanine, corticosteroid, methotrexate, 6-mercaptopurine, azacitidine, arsenic trioxide and all-trans retinoic acid, or any combination thereof.

In some embodiments, the anti-CD38 antibody is administered at a dose of between about 8 mg/kg and about 16 mg/kg.

In some embodiments, the anti-CD38 antibody is administered or provided for administration in a pharmaceutical composition comprising between about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the anti-CD38 antibody is administered or provided for administration in a pharmaceutical composition comprising about 1,800 mg of the anti-CD38 antibody and about 30,000 U of rHuPH20.

In some embodiments, the anti-CD38 antibody is administered or provided for administration in a pharmaceutical composition comprising about 120 mg/mL of the anti-CD38 antibody and about 2,000 U/mL of rHuPH20.

In some embodiments, the –CD38 antibody is administered or provided for administration in a pharmaceutical composition comprising
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the anti-CD38 antibody is administered or provided for administration in a pharmaceutical composition comprising
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the anti-CD38 antibody is administered or provided for administration in a pharmaceutical composition comprising
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

Combinations of Anti-CD38 Antibodies and BCMAxCD3 Bispecific Antibodies

The disclosure also provides a method of treating a cancer in a subject, comprising administering a therapeutically effective amount of a BCMAxCD3 bispecific antibody and an anti-CD38 antibody to the subject to treat the cancer.

The disclosure also provides a method of treating a cancer in a subject, comprising administering a therapeutically effective amount of a BCMAxCD3 bispecific antibody to the subject to treat the cancer, wherein the subject has been treated with an anti-CD38 antibody prior to administering the BCMAxCD3 bispecific antibody.

The disclosure also provides a method of treating a cancer in a subject, comprising administering a therapeutically effective amount of a BCMAxCD3 bispecific antibody to the subject to treat the cancer, wherein the subject is relapsed or refractory to treatment with a prior anti-cancer therapeutic.

T cell redirecting therapeutics such as BCMAxCD3 bispecific antibodies such as JNJ-957 redirect T cells to the BCMA-positive tumor cells such as multiple myeloma cells, which is followed by perforin/granzyme release or activation of the FASL/FAS pathway, and ultimately death of the BCMA-positive tumor cell death. Efficacy of the T cell redirecting therapeutics such as BCMAxCD3 bispecific antibodies may hence be influenced by the availability and activity of the recruited T cells as well as possible modulated expression of a tumor associated antigen such as BCMA on tumor cells.

In some embodiments, the cancer is a BCMA expressing cancer.

B-cell maturation antigen (BCMA) is a cell membrane bound tumor necrosis factor receptor family member involved in differentiation of B-cells to plasma cells. Expression of BCMA is restricted to the B-cell lineage where it is predominantly expressed in the interfollicular region of germinal centers and on differentiated plasma cells and plasmablasts. BCMA is virtually absent on naïve and memory B cells (Tai and Anderson, Immunotherapy 7: 1187-99, 2015).

In some embodiments, the cancer is a hematologic malignancy.

In some embodiments, the cancer is a multiple myeloma, a smoldering myeloma, a monoclonal gammopathy of undetermined significance (MGUS), a B-cell acute lymphoblastic leukemia, a diffuse large B-cell lymphoma, a Burkitt's lymphoma, a follicular lymphoma, a mantle-cell lymphoma, Waldenstrom's macroglobulinema, plasma cell leukemia, light chain amyloidosis or non-Hodgkin's lymphoma. An experienced physician makes the cancer diagnosis.

In some embodiments, the subject is relapsed or refractory to treatment with the anti-CD38 antibody or lenalinomide, or a combination thereof.

In some embodiments, the subject is relapsed or refractory to treatment with the anti-CD38 antibody. In some embodiments, the subject is relapsed or refractory to treatment with lenalinomide.

In some embodiments, the subject is relapsed or refractory to treatment with a prior anti-cancer therapeutic, such as a therapeutic used to treat multiple myeloma or other hematological malignancies.

In some embodiments, the subject is refractory or relapsed to treatment with THALOMID® (thalidomide), REVLIMID® (lenalidomide), POMALYST® (pomalidomide), VELCADE® (bortezomib), NINLARO (ixazomib), KYPROLIS® (carfilzomib), FARADYK® (panobinostat), AREDIA® (pamidronate), ZOMETA® (zoledronic acid), DARZALEX® (daratumumab), elotozumab or melphalan.

In some embodiments, the subject is relapsed to treatment with DARZALEX® (daratumumab).

In some embodiments, the BCMAxCD3 bispecific antibody and the anti-CD38 antibody are antigen binding fragments. Exemplary antigen binding fragments are Fab, F(ab')2, Fd and Fv fragments.

In some embodiments, the BCMAxCD3 bispecific antibody is chimeric, humanized or human.

In some embodiments, the BCMAxCD3 bispecific antibody is an IgG1, an IgG2, an IgG3 or an IgG4 isotype.

In some embodiments, the BCMAxCD3 bispecific antibody is an IgG4 isotype.

In some embodiments, the BCMAxCD3 bispecific antibody comprises a BCMA binding domain comprising the HCDR1 of SEQ ID NO: 23, the HCDR2 of SEQ ID NO: 24, the HCDR3 of SEQ ID NO: 25, the LCDR1 of SEQ ID NO: 26, the LCDR2 of SEQ ID NO: 27 and the LCDR3 of SEQ ID NO: 28 and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38.

In some embodiments, the BCMA binding domain comprises the VH of SEQ ID NO: 29 and the VL of SEQ ID NO: 30 and the CD3 biding domain comprises the VH of SEQ ID NO: 39 and the VL of SEQ ID NO: 40.

In some embodiments, the BCMAxCD3 bispecific antibody is an IgG4 isotype and comprises phenylalanine at position 405 and arginine at position 409 in a first heavy chain (HC1) and leucine at position 405 and lysine at position 409 in a second heavy chain (HC2), wherein residue numbering is according to the EU Index.

In some embodiments, the BCMAxCD3 bispecific antibody further comprises proline at position 228, alanine at position 234 and alanine at position 235 in both the HC1 and the HC2.

In some embodiments, the BCMAxCD3 bispecific antibody comprises the HC1 of SEQ ID NO: 31, a first light chain (LC1) of SEQ ID NO: 32, the HC2 of SEQ ID NO: 41 and a second light chain (LC2) of SEQ ID NO: 42.

In some embodiments, the BCMAxCD3 bispecific antibody is BI 836909, PF-06863135, AMG-701 or CC-93269.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody comprises a heavy chain (HC) of SEQ ID NO: 12 and a light chain (LC) of SEQ ID NO: 13.

In some embodiments, the anti-CD38 antibody is DARZALEX® (daratumumab).

In some embodiments, the anti-CD38 antibody comprises
the VH of SEQ ID NO: 14 and the VL of SEQ ID NO: 15;
the VH of SEQ ID NO: 16 and the VL of SEQ ID NO: 17;
the VH of SEQ ID NO: 18 and the VL of SEQ ID NO: 19; or
the VH of SEQ ID NO: 20 and the VL of SEQ ID NO: 21.

In some embodiments, the anti-CD38 antibody is chimeric, humanized or human.

In some embodiments, the anti-CD38 antibody is an IgG1, an IgG2, an IgG3 or an IgG4 isotype.

In some embodiments, the anti-CD38 antibody is an IgG1 isotype.

In some embodiments, the anti-CD38 antibody is administered at a dose of between about 8 mg/kg and about 16 mg/kg.

In some embodiments, the BCMAxCD3 bispecific antibody and the anti-CD38 antibody are administered by an intravenous injection.

In some embodiments, the BCMAxCD3 bispecific antibody is administered by an intravenous injection and the anti-CD38 antibody is administered by a subcutaneous injection.

In some embodiments, the BCMAxCD3 bispecific antibody and the anti-CD38 antibody is administered by a subcutaneous injection.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is selected from the group consisting of lenalidomide, thalidomide, pomalidomide, bortezomib, carfilzomib, elotozumab, ixazomib, melphalan, prednisone or dexamethasone, or any combination thereof.

In some embodiments, the anti-CD38 antibody is administered or provided for administration in a pharmaceutical composition comprising between about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the anti-CD38 antibody is administered or provided for administration in a pharmaceutical composition comprising about 1,800 mg of the anti-CD38 antibody and about 30,000 U of rHuPH20.

In some embodiments, the anti-CD38 antibody is administered or provided for administration in a pharmaceutical composition comprising about 120 mg/mL of the anti-CD38 antibody and about 2,000 U/mL of rHuPH20.

In some embodiments, the anti-CD38 antibody is administered or provided for administration in a pharmaceutical composition comprising
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the anti-CD38 antibody is administered or provided for administration in a pharmaceutical composition comprising
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the anti-CD38 antibody is administered or provided for administration in a pharmaceutical composition comprising
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

The dose of the BCMAxCD3 bispecific antibody and the anti-CD38 antibody given to a subject having cancer, such as multiple myeloma, is sufficient to alleviate or at least partially arrest the disease being treated ("therapeutically effective amount") and includes from about 0.005 mg to about 100 mg/kg, e.g. about 0.05 mg to about 30 mg/kg or about 5 mg to about 25 mg/kg, or about 4 mg/kg, about 8 mg/kg, about 16 mg/kg, or about 24 mg/kg of the antibody. Suitable doses include, for example, about 1, 2, 3, 4, 5, 6, 7, 8, 9, 10, 15, 16, 17, 18, 19, 20, 21, 22, 23, 24, 25, 30, 40, 50, 60, 70, 80, 90, or 100 mg/kg.

A fixed unit dose of the BCMAxCD3 bispecific antibody and/or the anti-CD38 antibody may also be given, for example, 50, 100, 200, 500, or 1000 mg, or the dose may be based on the patient's surface area, e.g., 500, 400, 300, 250, 200, or 100 mg/m². Usually between 1 and 8 doses, (e.g., 1, 2, 3, 4, 5, 6, 7, or 8) may be administered to treat a cancer, such as a multiple myeloma, but 9, 10, 11, 12, 13, 14, 15, 16, 17, 18, 19, 20, or more doses may be given.

The administration of the BCMAxCD3 bispecific antibody and/or the anti-CD38 antibody may be repeated after one day, two days, three days, four days, five days, six days, one week, two weeks, three weeks, one month, five weeks, six weeks, seven weeks, two months, three months, four months, five months, six months, or longer. Repeated courses of treatment are also possible, as is chronic administration. The repeated administration may be at the same dose or at a different dose. For example, the BCMAxCD3 bispecific antibody and the anti-CD38 antibody may be administered at 8 mg/kg or at 16 mg/kg at weekly intervals for 8 weeks, followed by administration at 8 mg/kg or at 16 mg/kg every two weeks for an additional 16 weeks, followed by administration at 8 mg/kg or at 16 mg/kg every four weeks by intravenous infusion.

The BCMAxCD3 bispecific antibody and the anti-CD38 antibody may be administered by maintenance therapy, such as, e.g., once a week for a period of 6 months or more. For example, the BCMAxCD3 bispecific antibody and the anti-CD38 antibody may be provided as a daily dosage in an amount of about 0.1 mg/kg to about 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90, or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19, or 20 after initiation of treatment, or any combination thereof, using single or divided doses of every 24, 12, 8, 6, 4, or 2 hours, or any combination thereof.

The BCMAxCD3 bispecific antibody and the anti-CD38 antibody may also be administered prophylactically in order to reduce the risk of developing the cancer, such as the multiple myeloma, delay the onset of the occurrence of an event in cancer progression, and/or reduce the risk of recurrence when the cancer is in remission.

In some embodiments, the BCMAxCD3 bispecific antibody is administered to the subject after the subject has been administered the anti-CD38 antibody. The BCMAxCD3 bispecific antibody may be administered one week, two weeks, three weeks, one month, five weeks, six weeks, seven weeks, two months, three months, four months, five months, six months, or longer after administering the anti-CD38 antibody. In some embodiments, the subject administered the BCMAxCD3 antibody is resistant and/or refractory to treatment with the anti-CD38 antibody.

The invention also provides pharmaceutical composition comprising a BCMAxCD3 bispecific antibody comprising a BCMA binding domain comprising a VH of SEQ ID NO: 29 and a VL of SEQ ID NO: 30 and a CD3 binding domain comprising the VH of SEQ ID NO: 39 and the VL of SEQ ID NO: 40, and an anti-CD38 antibody comprising a VH of SEQ ID NO: 4 and the VL of SEQ ID NO: 5.

In some embodiments, the pharmaceutical composition comprises the BCMAxCD3 bispecific antibody comprising the HC1 of SEQ ID NO: 31, the LC1 of SEQ ID NO: 32, the HC2 of SEQ ID NO: 41 the LC2 of SEQ ID NO: 42, and the anti-CD38 antibody comprising the HC of SEQ ID NO: 12 and the LC of SEQ ID NO: 13.

In some embodiment, the pharmaceutical composition is a non-fixed combination.

In some embodiments, the pharmaceutical composition comprises from about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

The BCMAxCD3 bispecific antibody may be formulated as a pharmaceutical composition comprising about 20 mg/mL to about 120 mg/mL antibody, acetic acid, histidine, sodium chloride, mannitol and/or polysorbate-20.

In some embodiments, the pharmaceutical composition comprises about 1,800 mg of the anti-CD38 antibody and about 30,000 U of rHuPH20.

In some embodiments, the pharmaceutical composition comprises about 120 mg/mL of the anti-CD38 antibody and about 2,000 U/mL of rHuPH20.

In some embodiments, the pharmaceutical composition further comprises one or more excipients.

In some embodiments, the one or more excipients is histidine, methionine, sorbitol or polysorbate-20 (PS-20), or any combination thereof.

In some embodiments, the pharmaceutical composition comprises
between about 100 mg/mL and about 120 mg/mL of the anti-CD38 antibody formulated in
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the pharmaceutical composition comprises about 10 mM histidine.

In some embodiments, the pharmaceutical composition comprises about 300 mM sorbitol.

In some embodiments, the pharmaceutical composition comprises about 0.04% (w/v) PS-20.

In some embodiments, the pharmaceutical composition comprises about 1 mg/mL methionine.

In some embodiments, the pharmaceutical composition comprises
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the pharmaceutical composition comprises
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

The disclosure also provides a kit comprising the pharmaceutical composition comprising the BCMAxCD3 bispecific antibody and the anti-CD38 antibody.

Treatment with BCMAxCD3 Bispecific Antibodies in Relapsed or Refractory Subjects The disclosure also provides a method of treating a cancer in a subject, comprising administering a therapeutically effective amount of a BCMAxCD3 bispecific antibody to the subject to treat the cancer, wherein the subject is relapsed or refractory to treatment with a prior anti-cancer therapeutic.

In some embodiments, the BCMAxCD3 bispecific antibody comprises a BCMA binding domain comprising the HCDR1 of SEQ ID NO: 23, the HCDR2 of SEQ ID NO: 24, the HCDR3 of SEQ ID NO: 25, the LCDR1 of SEQ ID NO: 26, the LCDR2 of SEQ ID NO: 27 and the LCDR3 of SEQ ID NO: 28, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38.

In some embodiments, the BCMA binding domain comprises the VH of SEQ ID NO: 29 and the VL of SEQ ID NO: 30, and the CD3 biding domain comprises the VH of SEQ ID NO: 39 and the VL of SEQ ID NO: 40.

In some embodiments, the BCMAxCD3 bispecific antibody is an IgG4 isotype and comprises phenylalanine at position 405 and arginine at position 409 in the HC1 and leucine at position 405 and lysine at position 409 in the HC2, wherein residue numbering is according to the EU Index.

In some embodiments, the BCMAxCD3 bispecific antibody further comprises proline at position 228, alanine at position 234 and alanine at position 235 in both the HC1 and the HC2.

In some embodiments, the BCMAxCD3 bispecific antibody comprises the HC1 of SEQ ID NO: 31, the LC1 of SEQ ID NO: 32, the HC2 of SEQ ID NO: 41 and the LC2 of SEQ ID NO: 42.

In some embodiments, the cancer is a hematological malignancy.

In some embodiments, the hematological malignancy is a multiple myeloma.

In some embodiments, the multiple myeloma is a high-risk multiple myeloma.

In some embodiments, the subject having the high-risk multiple myeloma has one or more chromosomal abnormalities comprising:
t(4;14)(p16;q32);
t(14;16)(q32;q23);
del17p;
1qAmp;
t(4;14)(p16;q32) and t(14;16)(q32;q23);
t(4;14)(p16;q32) and del17p;
t(14;16)(q32;q23) and del17p; or
t(4;14)(p16;q32), t(14;16)(q32;q23) and del17p, or any combination thereof.

In some embodiments, the subject is relapsed or refractory to treatment with the anti-CD38 antibody, lenalinomide, bortezomib, pomalidomide, carfilzomib, elotozumab, ixazomib, melphalan or thalidomide, or any combination thereof.

In some embodiments, the subject is relapsed or refractory to treatment with lenalinomide. In some embodiments, the subject is relapsed or refractory to treatment with bortezomib. In some embodiments, the subject is relapsed or refractory to treatment with pomalidomide. In some embodiments, the subject is relapsed or refractory to treatment with carfilzomib. In some embodiments, the subject is relapsed or refractory to treatment with elotozumab. In some embodiments, the subject is relapsed or refractory to treatment with ixazomib. In some embodiments, the subject is relapsed or refractory to treatment with melphalan. In some embodiments, the subject is relapsed or refractory to treatment with thalidomide.

In some embodiments, the subject is relapsed to treatment with the anti-CD38 antibody.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody is an IgG1 isotype.

In some embodiments, the anti-CD38 antibody comprises the HC of SEQ ID NO: 12 and the LC of SEQ ID NO: 13.

In some embodiments, the anti-CD38 antibody comprises the VH of SEQ ID NO: 14 and the VL of SEQ ID NO: 15; the VH of SEQ ID NO: 16 and the VL of SEQ ID NO: 17; the VH of SEQ ID NO: 18 and the VL of SEQ ID NO: 19; or
the VH of SEQ ID NO: 20 and the VL of SEQ ID NO: 21.

In some embodiments, the anti-CD38 antibody is an IgG1 isotype.

In some embodiments, the subject is a human.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is selected from the group consisting of lenalidomide, thalidomide, pomalidomide, bortezomib, carfilzomib, elotozumab, ixazomib, melphalan, prednisone or dexamethasone, or any combination thereof.

Combination Therapies with T Cell Redirecting Therapeutics that Binds GPRC5D and Anti-CD38 Antibodies The disclosure also provides a method of treating a cancer in a subject, comprising administering a therapeutically effective amount of a T-cell redirecting therapeutic that binds GPRC5D and an anti-CD38 antibody to the subject to treat the cancer.

In some embodiments, the anti-CD38 antibody is administered to subject prior to administering the T cell redirecting therapeutic that binds GPRC5D.

In some embodiments, the subject is relapsed or refractory to treatment with a prior anti-cancer therapeutic.

In some embodiments, the cancer is a GPRC5D expressing cancer.

In some embodiments, the GPRC5D expressing cancer is a hematological malignancy or a solid tumor.

In some embodiments, the hematological malignancy is a leukemia, a lymphoma, or a multiple myeloma.

In some embodiments, the hematological malignancy is the leukemia. In some embodiments, the hematological malignancy is the lymphoma. In some embodiments, the hematological malignancy is the multiple myeloma.

In some embodiments, the solid tumor is an ovarian cancer, a lung cancer, a stomach cancer, a prostate cancer, a renal carcinoma, a liver cancer, a pancreatic cancer, a colon cancer, an oesophageal cancer, a bladder cancer, a cervical carcinoma or a malignant melanoma. GPRC5D has been disclosed to be expressed in these tumors, see, e.g Int. Pat. Publ. No. WO2018/147245.

In some embodiments, the subject is relapsed or refractory to treatment with the anti-CD38 antibody, lenalinomide, bortezomib, pomalidomide, carfilzomib, elotozumab, ixazomib, melphalan or thalidomide, or any combination thereof.

In some embodiments, the subject is relapsed or refractory to treatment with lenalinomide. In some embodiments, the subject is relapsed or refractory to treatment with bortezomib. In some embodiments, the subject is relapsed or refractory to treatment with pomalidomide. In some embodiments, the subject is relapsed or refractory to treatment with carfilzomib. In some embodiments, the subject is relapsed or refractory to treatment with elotozumab. In some embodiments, the subject is relapsed or refractory to treatment with ixazomib. In some embodiments, the subject is relapsed or refractory to treatment with melphalan. In some embodiments, the subject is relapsed or refractory to treatment with thalidomide. In some embodiments, the subject is relapsed or refractory to treatment with the anti-CD38 antibody.

In some embodiments, the multiple myeloma is a newly diagnosed multiple myeloma.

In some embodiments, the multiple myeloma is a relapsed or refractory multiple myeloma.

In some embodiments, the multiple myeloma is a high-risk multiple myeloma.

In some embodiments, the subject having the high-risk multiple myeloma has one or more chromosomal abnormalities comprising:
t(4;14)(p16;q32);
t(14;16)(q32;q23);
del17p;
1 qAmp;
t(4;14)(p16;q32) and t(14;16)(q32;q23);

t(4;14)(p16;q32) and del17p;
t(14;16)(q32;q23) and del17p; or
t(4;14)(p16;q32), t(14;16)(q32;q23) and del17p, or any combination thereof.

In some embodiments, the T-cell redirecting therapeutic binds CD3, CD3 epsilon (CD3ε), CD8, K12L4, NKG2E, NKG2D, NKG2F, BTNL3, CD186, BTNL8, PD-1, CD195, or NKG2C.

In some embodiments, the T-cell redirecting therapeutic comprises a GPRC5D binding domain comprising the HCDR1 of SEQ ID NO: 43, the HCDR2 of SEQ ID NO: 44, the HCDR3 of SEQ ID NO: 45, the LCDR1 of SEQ ID NO: 46, the LCDR2 of SEQ ID NO: 47 and the LCDR3 of SEQ ID NO: 48, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38.

In some embodiments, the GPRC5D binding domain comprises the VH of SEQ ID NO: 49 and the VL of SEQ ID NO: 50 and the CD3 binding domain comprises the VH of SEQ ID NO: 39 and the VL of SEQ ID NO: 40.

In some embodiments, the T-cell redirecting therapeutic that binds GPRCSC is a multispecific antibody, a CAR or a T cell expressing the CAR.

In some embodiments, the multispecific antibody is an IgG1, an IgG2, an IgG3 or an IgG4 isotype.

In some embodiments, the multispecific antibody is the IgG1 isotype. In some embodiments, the multispecific antibody is the IgG2 isotype. In some embodiments, the multispecific antibody is the IgG3 isotype. In some embodiments, the multispecific antibody is the IgG4 isotype.

In some embodiments, the multispecific antibody comprises one or more Fc substitutions that reduces binding of the multispecific antibody to a Fcγ receptor (FcγR).

In some embodiments, the one or more Fc substitutions is selected from the group consisting of F234A/L235A on IgG4, L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4 and S228P/F234A/L235A/G236-deleted/G237A/P238S on IgG4, wherein residue numbering is according to the EU index.

In some embodiments, the multispecific antibody further comprises a S228P substitution.

In some embodiments, the multispecific antibody comprises one or more asymmetric substitutions in a first CH3 domain or in a second CH3 domain, or in both the first CH3 domain and the second CH3 domain.

In some embodiments, one or more asymmetric substitutions is selected from the group consisting of F450L/K409R, wild-type/F409L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

In some embodiments, the multispecific antibody comprises the HC1 of SEQ ID NO: 51, the LC1 of SEQ ID NO: 52, the HC2 of SEQ ID NO: 41 and the LC2 of SEQ ID NO: 42.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody is an IgG1 isotype.

In some embodiments, the anti-CD38 antibody comprises the HC of SEQ ID NO: 12 and the LC of SEQ ID NO: 13.

In some embodiments, the anti-CD38 antibody comprises
the VH of SEQ ID NO: 14 and the VL of SEQ ID NO: 15;
the VH of SEQ ID NO: 16 and the VL of SEQ ID NO: 17;
the VH of SEQ ID NO: 18 and the VL of SEQ ID NO: 19; or
the VH of SEQ ID NO: 20 and the VL of SEQ ID NO: 21.

In some embodiments, the anti-CD38 antibody is an IgG1 isotype.

In some embodiments, the anti-CD38 antibody is administered at a dose of between about 8 mg/kg and about 16 mg/kg.

In some embodiments, the T-cell redirecting therapeutic that binds GPRC5D and the anti-CD38 antibody are administered by an intravenous injection.

In some embodiments, the T-cell redirecting therapeutic that binds GPRC5D is administered by an intravenous injection and the anti-CD38 antibody is administered by a subcutaneous injection.

In some embodiments, the T-cell redirecting therapeutic that binds GPRC5D and the anti-CD38 antibody is administered by a subcutaneous injection.

In some embodiments, the subject is a human.

In some embodiments, the T cell redirecting therapeutic that binds GPRC5D is a GPRC5DxCD3 bispecific antibody.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is selected from the group consisting of lenalidomide, thalidomide, pomalidomide, bortezomib, carfilzomib, elotozumab, ixazomib, melphalan, dexamethasone or prednisone.

In some embodiments, the anti-CD38 antibody is administered or provided for administration in a pharmaceutical composition comprising between about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the anti-CD38 antibody is administered or provided for administration in a pharmaceutical composition comprising about 1,800 mg of the anti-CD38 antibody and about 30,000 U of rHuPH20.

In some embodiments, the anti-CD38 antibody is administered or provided for administration in a pharmaceutical composition comprising about 120 mg/mL of the anti-CD38 antibody and about 2,000 U/mL of rHuPH20.

In some embodiments, the anti-CD38 antibody is administered or provided for administration in a pharmaceutical composition comprising
between about 100 mg/mL and about 120 mg/mL of the anti-CD38 antibody;
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the anti-CD38 antibody is administered or provided for administration in a pharmaceutical composition comprising
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the anti-CD38 antibody is administered or provided for administration in a pharmaceutical composition comprising
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

The disclosure also provides a pharmaceutical combination comprising a GPRC5DxCD3 bispecific antibody comprising a GPRC5D binding domain comprising the HCDR1 of SEQ ID NO: 43, the HCDR2 of SEQ ID NO: 44, the HCDR3 of SEQ ID NO: 45, the LCDR1 of SEQ ID NO: 46, the LCDR2 of SEQ ID NO: 47 and the LCDR3 of SEQ ID NO: 48, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38 and an anti-CD38 antibody comprising the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the GPRC5D binding domain comprises the VH of SEQ ID NO: 49 and the VL of SEQ ID NO: 50 and the CD3 binding domain comprises the VH of SEQ ID NO: 39 and the VL of SEQ ID NO: 40, and the anti-CD38 antibody comprises the VH of SEQ ID NO: 4 and the VL of SEQ ID NO: 5.

In some embodiments, the GPRC5DxCD3 bispecific antibody comprises the HC1 of SEQ ID NO: 51, the LC1 of SEQ ID NO: 52, the HC2 of SEQ ID NO: 41 and the LC2 of SEQ ID NO: 42, and the anti-CD38 antibody comprises the HC of SEQ ID NO: 12 and the LC of SEQ ID NO: 13.

In some embodiments, the pharmaceutical combination is a non-fixed combination.

In some embodiments, the pharmaceutical combination comprises from about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the pharmaceutical combination comprises about 1,800 mg of the anti-CD38 antibody and about 30,000 U of rHuPH20.

In some embodiments, the pharmaceutical combination comprises about 120 mg/mL of the anti-CD38 antibody and about 2,000 U/mL of rHuPH20.

In some embodiments, the pharmaceutical combination further comprises one or more excipients.

In some embodiments, the one or more excipients is histidine, methionine, sorbitol or polysorbate-20 (PS-20), or any combination thereof.

In some embodiments, the pharmaceutical composition comprises
between about 100 mg/mL and about 120 mg/mL of the anti-CD38 antibody;
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the pharmaceutical combination comprises about 10 mM histidine.

In some embodiments, the pharmaceutical combination comprises about 300 mM sorbitol.

In some embodiments, the pharmaceutical combination comprises about 0.04% (w/v) PS-20.

In some embodiments, the pharmaceutical combination comprises about 1 mg/mL methionine.

In some embodiments, the pharmaceutical combination comprises
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the pharmaceutical combination comprises
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

The disclosure also provides a pharmaceutical combination comprising the T cell redirecting therapeutic that binds GPRC5D and the anti-CD38 antibody.

Treatment with GPRC5DxCD3 Bispecific Antibodies in Relapsed or Refractory Subjects The disclosure also provides a method of treating a cancer in a subject, comprising administering a therapeutically effective amount of a GPRC5DxCD3 bispecific antibody to the subject to treat the cancer, wherein the subject is relapsed or refractory to treatment with a prior anti-cancer therapeutic.

In some embodiments, the GPRC5DxCD3 bispecific antibody comprises a GPRC5D binding domain comprising the HCDR1 of SEQ ID NO: 43, the HCDR2 of SEQ ID NO: 44, the HCDR3 of SEQ ID NO: 45, the LCDR1 of SEQ ID NO: 46, the LCDR2 of SEQ ID NO: 47 and the LCDR3 of SEQ ID NO: 48, and a CD3 binding domain comprising the HCDR1 of SEQ ID NO: 33, the HCDR2 of SEQ ID NO: 34, the HCDR3 of SEQ ID NO: 35, the LCDR1 of SEQ ID NO: 36, the LCDR2 of SEQ ID NO: 37 and the LCDR3 of SEQ ID NO: 38.

In some embodiments, the GPRC5D binding domain comprises the VH of SEQ ID NO: 49 and the VL of SEQ ID NO: 50 and the CD3 binding domain comprises the VH of SEQ ID NO: 39 and the VL of SEQ ID NO: 40.

In some embodiments, the GPRC5DxCD3 bispecific antibody is an IgG4 isotype and comprises phenylalanine at position 405 and arginine at position 409 in the HC1 and leucine at position 405 and lysine at position 409 in the HC2, wherein residue numbering is according to the EU Index.

In some embodiments, the GPRC5DxCD3 bispecific antibody further comprises proline at position 228, alanine at position 234 and alanine at position 235 in both the HC1 and the HC2.

In some embodiments, the GPRC5DxCD3 bispecific antibody comprises the HC1 of SEQ ID NO: 51, the LC1 of SEQ ID NO: 52, the HC2 of SEQ ID NO: 41 and the LC2 of SEQ ID NO: 42.

In some embodiments, the cancer is a hematological malignancy or a solid tumor

In some embodiments, the cancer is a multiple myeloma, a lymphoma, a melanoma, a breast cancer, an endometrial cancer, an ovarian cancer, a lung cancer, stomach cancer, a prostate cancer, a renal carcinoma, a liver cancer, a pancreatic cancer, a colon cancer, an oesophageal cancer, a bladder cancer or a cervical carcinoma.

In some embodiments, the multiple myeloma is a high-risk multiple myeloma.

In some embodiments, the subject having the high-risk multiple myeloma has one or more chromosomal abnormalities comprising:
t(4;14)(p16;q32);
t(14;16)(q32;q23);
del17p;
1qAmp;
t(4;14)(p16;q32) and t(14;16)(q32;q23);
t(4;14)(p16;q32) and del17p;
t(14;16)(q32;q23) and del17p; or
t(4;14)(p16;q32), t(14;16)(q32;q23) and del17p, or any combination thereof.

In some embodiments, the subject is refractory or relapsed to treatment with the anti-CD38 antibody, lenalinomide, bortezomib, pomalidomide, carfilzomib, elotozumab, ixazomib, melphalan or thalidomide, or any combination thereof.

In some embodiments, the subject is relapsed or refractory to treatment with the anti-CD38 antibody.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody is an IgG1 isotype.

In some embodiments, the anti-CD38 antibody comprises the HC of SEQ ID NO: 12 and the LC of SEQ ID NO: 13.

In some embodiments, the anti-CD38 antibody comprises
the VH of SEQ ID NO: 14 and the VL of SEQ ID NO: 15;
the VH of SEQ ID NO: 16 and the VL of SEQ ID NO: 17;
the VH of SEQ ID NO: 18 and the VL of SEQ ID NO: 19; or
the VH of SEQ ID NO: 20 and the VL of SEQ ID NO: 21.

In some embodiments, the anti-CD38 antibody is an IgG1 isotype.

In some embodiments, the subject is a human.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is selected from the group consisting of lenalidomide, thalidomide, pomalidomide, bortezomib, carfilzomib, elotozumab, ixazomib, melphalan, dexamethasone, vincristine, cyclophosphamide, hydroxy daunorubicin, prednisone, rituximab, imatinib, dasatinib, nilotinib, bosutinib, ponatinib, bafetinib, saracatinib, tozasertib or danusertib, cytarabine, daunorubicin, idarubicin, mitoxantrone, hydroxyurea, decitabine, cladribine, fludarabine, topotecan, etoposide 6-thioguanine, corticosteroid, methotrexate, 6-mercaptopurine, azacitidine, arsenic trioxide and all-trans retinoic acid, or any combination thereof.

Combination Therapies with T Cell Redirecting Therapeutics that Bind CD19 and Anti-CD38 Antibodies The disclosure also provides a method of treating a cancer in a subject, comprising administering a therapeutically effective amount of a T-cell redirecting therapeutic that binds
CD19 and an anti-CD38 antibody to the subject to treat the cancer.

In some embodiments, the subject has been treated with an anti-CD38 antibody prior to administering the T-cell redirecting therapeutic that binds CD19.

The disclosure also provides a method of enhancing efficacy of a T cell redirecting therapeutic that binds CD19 in a subject having a cancer, comprising administering to the subject an anti-CD38 antibody prior to administering the T cell redirecting therapeutic that binds CD19.

In some embodiments, the subject is relapsed or refractory to treatment with a prior anti-cancer therapeutic.

In some embodiments, the cancer is a hematological malignancy or a solid tumor.

In some embodiments, the hematological malignancy is lymphoma, a B cell malignancy, Hodgkin's lymphoma, non-Hodgkin's lymphoma, a DLBLC, a FL, a MCL, a marginal zone B-cell lymphoma (MZL), a mucosa-associated lymphatic tissue lymphoma (MALT), a CLL, an ALL, an AML, Waldenstrom's Macroglobulinemia or a T-cell lymphoma.

In some embodiments, the solid tumor is a lung cancer, a liver cancer, a cervical cancer, a colon cancer, a breast cancer, an ovarian cancer, a pancreatic cancer, a melanoma, a glioblastoma, a prostate cancer, an esophageal cancer or a gastric cancer. WO2019057124A1 discloses cancers that are amenable to treatment with T cell redirecting therapeutics that bind CD19.

In some embodiments, the T-cell redirecting therapeutic binds CD3 epsilon (CD3ε), CD8, KI2L4, NKG2E, NKG2D, NKG2F, BTNL3, CD186, BTNL8, PD-1, CD195, or NKG2C.

In some embodiments, the T-cell redirecting therapeutic that binds CD19 comprises a CD19 binding domain of blinatumomab, axicabtagene ciloleucel, tisagenlecleucel-t, inebilizumab, lisocabtagene maraleucel, XmAb-5574, CIK-CAR.CD19, ICTCAR-011, IM-19, JCAR-014, loncastuximab tesirine, MB-CART2019.1, OXS-1550, PBCAR-0191, PCAR-019, PCAR-119, Sen1-001, TI-1007, XmAb-5871, PTG-01, PZ01, Sen1_1904A, Sen1_1904B, UCART-19, CSG-CD19, DI-B4, ET-190, GC-007F or GC-022.

In some embodiments, the T cell redirecting therapeutic that binds CD19 comprises blinatumomab, axicabtagene ciloleucel, tisagenlecleucel-t, inebilizumab, lisocabtagene maraleucel, XmAb-5574, CIK-CAR.CD19, ICTCAR-011, IM-19, JCAR-014, loncastuximab tesirine, MB-CART2019.1, OXS-1550, PBCAR-0191, PCAR-019, PCAR-119, Sen1-001, TI-1007, XmAb-5871, PTG-01, PZ01, Sen1_1904A, Sen1_1904B, UCART-19, CSG-CD19, DI-B4, ET-190, GC-007F or GC-022.

In some embodiments, the T-cell redirecting therapeutic that binds CD19 is a multispecific antibody, a CAR or a T cell expressing the CAR.

In some embodiments, the anti-CD38 antibody comprises the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody is an IgG1 isotype.

In some embodiments, the anti-CD38 antibody comprises the HC of SEQ ID NO: 12 and the LC of SEQ ID NO: 13.

In some embodiments, the anti-CD38 antibody comprises
the VH of SEQ ID NO: 14 and the VL of SEQ ID NO: 15;
the VH of SEQ ID NO: 16 and the VL of SEQ ID NO: 17;
the VH of SEQ ID NO: 18 and the VL of SEQ ID NO: 19; or
the VH of SEQ ID NO: 20 and the VL of SEQ ID NO: 21.

In some embodiments, the anti-CD38 antibody is an IgG1 isotype.

In some embodiments, the anti-CD38 antibody is administered at a dose of between about 8 mg/kg and about 16 mg/kg.

In some embodiments, the T-cell redirecting therapeutic that binds CD19 and the anti-CD38 antibody are administered by an intravenous injection.

In some embodiments, the T-cell redirecting therapeutic that binds CD19 is administered by an intravenous injection and the anti-CD38 antibody is administered by a subcutaneous injection.

In some embodiments, the T-cell redirecting therapeutic that binds CD19 and the anti-CD38 antibody is administered by a subcutaneous injection.

In some embodiments, the subject is a human.

In some embodiments, the T cell redirecting therapeutic that binds CD19 is a CD19xCD3 bispecific antibody.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

The disclosure also provides a pharmaceutical combination comprising a CD19xCD3 bispecific antibody comprising blinatumomab of SEQ ID NO: 53 an anti-CD38 antibody comprising the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

In some embodiments, the anti-CD38 antibody comprises the VH of SEQ ID NO: 4 and the VL of SEQ ID NO: 5.

In some embodiments, the anti-CD38 antibody comprises the HC of SEQ ID NO: 12 and the LC of SEQ ID NO: 13.

In some embodiments, the pharmaceutical combination is a non-fixed combination.

In some embodiments, the pharmaceutical combination comprises from about 20 mg/mL to about 120 mg/mL of the anti-CD38 antibody in about 25 mM acetic acid, about 60 mM sodium chloride, about 140 mannitol and about 0.04% w/v polysorbate-20 (PS-20); at pH about 5.5.

In some embodiments, the pharmaceutical combination comprises about 1,800 mg of the anti-CD38 antibody and about 30,000 U of rHuPH20.

In some embodiments, the pharmaceutical combination comprises about 120 mg/mL of the anti-CD38 antibody and about 2,000 U/mL of rHuPH20.

In some embodiments, the pharmaceutical combination further comprises one or more excipients.

In some embodiments, the one or more excipients is histidine, methionine, sorbitol or polysorbate-20 (PS-20), or any combination thereof.

In some embodiments, the pharmaceutical combination comprises
between about 100 mg/mL and about 120 mg/mL of the anti-CD38 antibody;
between about 5 mM and about 15 mM histidine;
between about 100 mM and about 300 mM sorbitol;
between about 0.01% w/v and about 0.04% w/v PS-20; and
between about 1 mg/mL and about 2 mg/mL methionine, at a pH of about 5.5-5.6.

In some embodiments, the pharmaceutical combination comprises about 10 mM histidine.

In some embodiments, the pharmaceutical combination comprises about 300 mM sorbitol.

In some embodiments, the pharmaceutical combination comprises about 0.04% (w/v) PS-20.

In some embodiments, the pharmaceutical combination comprises about 1 mg/mL methionine.

In some embodiments, the pharmaceutical combination comprises
about 1,800 mg of the anti-CD38 antibody;
about 30,000 U of rHuPH20;
about 10 mM histidine;
about 300 mM sorbitol;
about 0.04% (w/v) PS-20; and
about 1 mg/mL methionine, at a pH of about 5.6.

In some embodiments, the pharmaceutical combination comprises
about 120 mg/mL of the anti-CD38 antibody;
about 2,000 U/mL of rHuPH20;
about 10 mM histidine;
about 300 mM sorbitol;
about 0.04% (w/v) PS-20; and
about 1 mg/mL methionine, at a pH of about 5.6.

In some embodiments, the pharmaceutical combination comprises 35 mcg of blinatumomab formulated with citric acid monohydrate (3.35 mg), lysine hydrochloride (23.23 mg), polysorbate 80 (0.64 mg), trehalose dihydrate (95.5 mg), and sodium hydroxide to adjust pH to 7.0.

In some embodiments, blinatumomab is reconstitution with 3 mL of preservative-free Sterile Water for Injection, USP.

A kit comprising the pharmaceutical combination comprising blinatumomab of SEQ ID NO: 53 an anti-CD38 antibody comprising the HCDR1 of SEQ ID NO: 6, the HCDR2 of SEQ ID NO: 7, the HCDR3 of SEQ ID NO: 8, the LCDR1 of SEQ ID NO: 9, the LCDR2 of SEQ ID NO: 10 and the LCDR3 of SEQ ID NO: 11.

T Cell Redirecting Therapeutics
Multispecific Antibodies

T cell redirecting therapeutic may be a multispecific molecule such as a bispecific antibody. Various multispecific and/or bispecific formats include formats described herein and recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule, or multispecific antibodies generated by arm exchange. Exemplary multispecific and/or bispecific formats include dual targeting molecules include Dual Targeting (DT)-Ig (GSK/Domantis), Two-in-one Antibody (Genentech) and mAb2 (F-Star), Dual Variable Domain (DVD)-Ig (Abbott), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS) and Dual Affinity Retargeting Technology (Fc-DART) (MacroGenics), F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech), Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies. Various formats of bispecific antibodies have been described, for example in Chames and Baty (2009) Curr Opin Drug Disc Dev 12: 276 and in Nunez-Prado et al., (2015) Drug Discovery Today 20(5):588-594.

Methods of Generating Antibodies Used in the Methods of the Invention

The antibodies used in the methods of the invention binding specific antigens may be selected de novo from, for example, a phage display library, where the phage is engineered to express human immunoglobulins or portions thereof such as Fabs, single chain antibodies (scFv), or unpaired or paired antibody variable regions (Knappik et al., *J Mol Biol* 296:57-86, 2000; Krebs et al., *J Immunol Meth* 254:67-84, 2001; Vaughan et al., *Nature Biotechnology* 14:309-14, 1996; Sheets et al., *PITAS* (USA) 95:6157-62, 1998; Hoogenboom and Winter, *J Mol Biol* 227:381, 1991; Marks et al., *J Mol Biol* 222:581, 1991). Phage display libraries expressing antibody heavy and light chain variable regions as fusion proteins with bacteriophage pIX coat protein as described in Shi et al (2010) J. Mol. Biol. 397:385-96 and Int'l Pat. Pub. No. WO2009/085462. The antibody libraries may be screened for binding to the desired antigen, such as BCMA, CD3, CD38, CD123, CD19, CD33, PSMA or TMEFF2 extracellular domain and the obtained positive clones may be further characterized and the Fabs isolated from the clone lysates, and subsequently cloned as full length antibodies. Such phage display methods for isolating human antibodies are established in the art. See for example: U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081.

T cell redirecting bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

Additional CH3 mutations that may be used include technologies such as Duobody® mutations (Genmab), Knob-in-Hole mutations (Genentech), electrostatically-matched mutations (Chugai, Amgen, NovoNordisk, Oncomed), the Strand Exchange Engineered Domain body (SEEDbody) (EMD Serono), and other asymmetric mutations (e.g. Zymeworks).

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHIL-MQVY/K409R, L368ADEGHNRSTVQ/K409AGRH, D3-99FHKRQ/K409AGRH, F405IKLSTVW/K409AGRH and Y407LWQ/K409AGRH.

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T3-66A_K409F, or T350V_L351Y_F405A_Y407V/T350V_T366L_K392L_T394W as described in US2012/0149876 or US2013/0195849.

SEEDbody mutations involve substituting select IgG residues with IgA residues to promote heavy chain heterodimerization as described in US20070287170.

Other exemplary mutations that may be used are R409D_K370E/D399K_E357K, S354C_T366W/Y349C_ T366S_L368A_Y407V, Y349C_T366W/S354C_ T366S_L368A_Y407V, T366K/L351D, L351K/Y349E, L351K/Y349D, L351K/L368E, L351Y_Y407A/T366A_K409F, L351Y_Y407A/T366V_K409F, K392D/D399K, K392D/E356K, K253E_D282K_K322D/D239K_E240K_K292D, K392D_K409D/D356K_D399K as described in WO2007/147901, WO 2011/143545, WO2013157954, WO2013-096291 and US2018/0118849.

Additional bispecific or multispecific structures that can be used as T cell redirecting therapeutics include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Fc Engineering of Antibodies

The Fc region of the T cell redirecting therapeutics such as bispecific or multispecific antibodies or the anti-CD38 antibodies may comprise at least one substitution in the Fc region that reduces binding of the T cell redirecting therapeutics to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be substituted to reduce binding of the Fc to the activating FcγR and subsequently to reduce effector function are substitutions L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4.

Fc substitutions that may be used to reduce CDC is a K322A substitution.

Well-known S228P substitution may further be made in IgG4 antibodies to enhance IgG4 stability.

An exemplary wild-type IgG1 comprises an amino acid sequence of SEQ ID NO: 103.

SEQ ID NO: 103:
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

An exemplary wild-type IgG4 comprises an amino acid sequence of SEQ ID NO: 104.

SEQ ID NO: 104:
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells (NK), monocytes, macrophages and neutrophils via Fc gamma receptors (FcγR) expressed on effector cells. For example, NK cells express FcγRIIIa, whereas monocytes express FcγRI, FcγRII and FcγRIIIa. ADCC activity of the antibodies may be assessed using an in vitro assay using cells expressing the protein the antibody binds to as target cells and NK cells as effector cells. Cytolysis may be detected by the release of label (e.g. radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and cells that express the protein the antibody binds to as target cells also engineered to express GFP or another labeled molecule. In an exemplary assay, effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the CD11$^+$CD14$^+$ macrophages using standard methods.

"Complement-dependent cytotoxicity", or "CDC", refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate CDC by binding complement receptors (e.g., CR3) on leukocytes. CDC of cells may be measured for example by plating Daudi cells at 1×10$^5$ cells/well (50 µL/well) in RPMI-B (RPMI supplemented with 1% BSA), adding 50 µL of test antibodies to the wells at final concentration between 0-100 µg/mL, incubating the reaction for 15 min at room temperature, adding 11 µL of pooled human serum to the wells, and incubation the reaction for 45 min at 37° C. Percentage (%) lysed cells may be detected as % propidium iodide stained cells in FACS assay using standard methods.

Binding of the antibody to FcγR or FcRn may be assessed on cells engineered to express each receptor using flow cytometry. In an exemplary binding assay, 2×10$^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 µL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel, respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

Chimeric Antigen Receptors (CAR)

Chimeric antigen receptors (CARs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

CAR typically comprises an extracellular domain that binds the antigen (e.g. prostate neoantigen), an optional linker, a transmembrane domain, and a cytosolic domain comprising a costimulatory domain and/or a signaling domain.

The extracellular domain of CAR may contain any polypeptide that binds the desired antigen (e.g. prostate neoantigen). The extracellular domain may comprise a scFv, a portion of an antibody or an alternative scaffold. CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD19, IL2R beta, IL2R gamma, IL7R a, ITGA1, VLA1, CD49a, ITGA4, IA4, CD49D, ITGA6, VLA-6, CD49f, ITGAD, CDI 1d, ITGAE, CD103, ITGAL, CDI 1a, LFA-1, ITGAM, CDI 1b, ITGAX, CDI 1c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMF1), CD152 (CTLA4), CD223 (LAG3), CD270 (HVEM), CD278 (ICOS), DAP10, LAT, NKD2C SLP76, TRIM, and ZAP70.

The intracellular signaling domain of CAR may be derived from the signaling domains of for example OO3ζ, CD3ε, CD22, CD79a, CD66d or CD39. "Intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of CAR positioned between the extracellular domain and the transmembrane domain may be a polypeptide of about 2 to 100 amino acids in length. The linker can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin.

Exemplary CARs that may be used are for example CAR that contains an extracellular domain that binds the prostate neoantigen of the invention, CD8 transmembrane domain and CD3ζ signaling domain. Other exemplary CARs contain an extracellular domain that binds the prostate neoantigen of the invention, CD8 or CD28 transmembrane domain, CD28, 41BB or OX40 costimulatory domain and CD3ζ signaling domain.

CARs are generated by standard molecular biology techniques. The extracellular domain that binds the desired antigen may be derived from antibodies or their antigen binding fragments generated using the technologies described herein.

While having described the invention in general terms, the embodiments of the invention will be further disclosed in the following examples that should not be construed as limiting the scope of the claims.

EXAMPLES

The following examples are provided to further describe some of the embodiments disclosed herein. The examples are intended to illustrate, not to limit, the disclosed embodiments.

General Materials and Methods

Antibodies and Reagents

Anti-BCMA/anti-CD3 antibody JNJ-957 (described in WO2017031104A1) and daratumumab were made by Janssen Pharmaceuticals. CNTO7008 (CD3xnull), BC3B4 (BCMAxnull) and 3930 (IgG isotype control), all made by Janssen Pharmaceuticals, were used as control antibodies. JNJ-957 is also called JNJ-7957.

JNJ-957 comprises a BCMA binding arm BCMB69 and a CD3 binding arm CD3B219, the amino acid sequences of which are shown in Table 3 and Table 4, respectively.

TABLE 3

| | Region | Sequence | SEQ ID NO: |
|---|---|---|---|
| BCMB69 | HCDR1 | SGSYFWG | 23 |
| | HCDR2 | SIYYSGITYYNPSLKS | 24 |
| | HCDR3 | HDGAVAGLFDY | 25 |
| | LCDR1 | GGNNIGSKSVH | 26 |
| | LCDR2 | DDSDRPS | 27 |
| | LCDR3 | QVWDSSSDHVV | 28 |
| | VH | QLQLQESGPGLVKPSETLSLTCTVSGGSISSGSYFWG WIRQPPGKGLEWIGSIYYSGITYYNPSLKSRVTISVD TSKNQFSLKLSSVTAADTAVYYCARHDGAVAGLFD YWGQGTLVTVSS | 29 |
| | VL | SYVLTQPPSVSVAPGQTARITCGGNNIGSKSVHWYQ QPPGQAPVVVVYDDSDRPSGIPERFSGSNSGNTATL TISRVEAGDEAVYYCQVWDSSSDHVVFGGGTKLTV LGQP | 30 |
| | HC | QLQLQESGPGLVKPSETLSLTCTVSGGSISSGSYFWG WIRQPPGKGLEWIGSIYYSGITYYNPSLKSRVTISVD TSKNQFSLKLSSVTAADTAVYYCARHDGAVAGLFD YWGQGTLVTVSSASTKGPSVFPLAPCSRSTSESTAA LGCLVKDYFPEPVTVSWNSGALTSGVHTFPAVLQS SGLYSLSSVVTVPSSSLGTKTYTCNVDHKPSNTKVD KRVESKYGPPCPPCPAPEAAGGPSVFLFPPKPKDTL MISRTPEVTCVVVDVSQEDPEVQFNWYVDGVEVH NAKTKPREEQFNSTYRVVSVLTVLHQDWLNGKEY KCKVSNKGLPSSIEKTISKAKGQPREPQVYTLPPSQE EMTKNQVSLTCLVKGFYPSDIAVEWESNGQPENNY KTTPPVLDSDGSFFLYSRLTVDKSRWQEGNVFSCSV MHEALHNHYTQKSLSLSLGK | 31 |
| | LC | SYVLTQPPSVSVAPGQTARITCGGNNIGSKSVHWYQ QPPGQAPVVVVYDDSDRPSGIPERFSGSNSGNTATL TISRVEAGDEAVYYCQVWDSSSDHVVFGGGTKLTV LGQPKAAPSVTLFPPSSEELQANKATLVCLISDFYPG AVTVAWKGDSSPVKAGVETTTPSKQSNNKYAASS YLSLTPEQWKSHRSYSCQVTHEGSTVEKTVAPTECS | 32 |

TABLE 4

| | Region | Sequence | SEQ ID NO: |
|---|---|---|---|
| CD3B219 | HCDR1 | TYAMN | 33 |
| | HCDR2 | RIRSKYNNYATYYAASVKG | 34 |
| | HCDR3 | HGNFGNSYVSWFAY | 35 |

TABLE 4-continued

| Region | Sequence | SEQ ID NO: |
|---|---|---|
| LCDR1 | RSSTGAVTTSNYAN | 36 |
| LCDR2 | GTNKRAP | 37 |
| LCDR3 | ALWYSNLWV | 38 |
| VH | EVQLVESGGGLVQPGGSLRLSCAASGFTFNTYA MNWVRQAPGKGLEWVARIRSKYNNYATYYAAS VKGRFTISRDDSKNSLYLQMNSLKTEDTAVYYC ARHGNFGNSYVSWFAYWGQGTLVTVSS | 39 |
| VL | QTVVTQEPSLTVSPGGTVTLTCRSSTGAVTTSNY ANWVQQKPGQAPRGLIGGTNKRAPGTPARFSGS LLGGKAALTLSGVQPEDEAEYYCALWYSNLWV FGGGTKLTVLGQP | 40 |
| HC | EVQLVESGGGLVQPGGSLRLSCAASGFTFNTYA MNWVRQAPGKGLEWVARIRSKYNNYATYYAAS VKGRFTISRDDSKNSLYLQMNSLKTEDTAVYYC ARHGNFGNSYVSWFAYWGQGTLVTVSSASTKG PSVFPLAPCSRSTSESTAALGCLVKDYFPEPVTVS WNSGALTSGVHTFPAVLQSSGLYSLSSVVTVPSS SLGTKTYTCNVDHKPSNTKVDKRVESKYGPPCP PCPAPEAAGGPSVFLFPPKPKDTLMISRTPEVTCV VVDVSQEDPEVQFNWYVDGVEVHNAKTKPREE QFNSTYRVVSVLTVLHQDWLNGKEYKCKVSNK GLPSSIEKTISKAKGQPREPQVYTLPPSQEEMTKN QVSLTCLVKGFYPSDIAVEWESNGQPENNYKTTP PVLDSDGSFLLYSKLTVDKSRWQEGNVFSCSVM HEALHNHYTQKSLSLSLGK | 41 |
| LC | QTVVTQEPSLTVSPGGTVTLTCRSSTGAVTTSNY ANWVQQKPGQAPRGLIGGTNKRAPGTPARFSGS LLGGKAALTLSGVQPEDEAEYYCALWYSNLWV FGGGTKLTVLGQPKAAPSVTLFPPSSEELQANKA TLVCLISDFYPGAVTVAWKADSSPVKAGVETTTP SKQSNNKYAASSYLSLTPEQWKSHRSYSCQVTH EGSTVEKTVAPTECS | 42 |

Bone Marrow and Peripheral Blood Mononuclear Cells

Peripheral blood mononuclear cells (PBMCs) from healthy donors and MM patients, and bone marrow mononuclear cells (BM-MNCs) from MM patient BM aspirates were isolated by Ficoll-Hypaque density-gradient centrifugation.

Cell Lines and Culture

The luciferase (LUC)-transduced multiple myeloma cell lines UM9, RPMI8226, U266 and MM1.S, as well as the non-transduced multiple myeloma cell lines NCI-H929 and RPMI8226, were cultured in RPMI 1640 (Invitrogen), supplemented with 10% fetal bovine serum (FBS; Lonza) and antibiotics (100 units/mL penicillin, 100 µg/ml streptomycin; both Life Technologies).

Flow Cytometric Analysis of Bone Marrow and Blood Samples from MM Patients

BM-localized MM cells were identified and analysed for cell surface marker expression levels by staining $1.0\times10^6$ cells/mL with HuMax-003 (CD38) FITC (this antibody binds to an epitope distinct from the epitope bound by daratumumab, Janssen Pharmaceuticals), CD138 PE, CD56 PC7, CD45 Krome Orange (all Beckman Coulter), CD269 (BCMA) APC (Biolegend), CD274 (PD-L1) BV421 and CD19 APC-H7 (both Becton Dickinson). BM or PB immune cell subsets were identified and analysed for cell surface marker expression levels by staining $1.0\times10^6$ cells/mL with CD45 Krome Orange, CD56 PC7 (both Beckman Coulter), CD14 APC-H7, CD19 APC-H7, CD3 V450, CD4 APC-H7 or PE, CD8 FITC, CD45-RA APC, CD127 PE.Cy7, CD62L PE, CD274 (PD-1) BV421, CD16 APC, HLA-DR APC-H7 (all Becton Dickinson) and CD25 PE (Dako). All BM samples were analysed within 24 hours from the time the sample was collected.

Flow cytometry was performed using a 7-laser LSR-FORTESSA (Becton Dickinson). Fluorescent labeled beads (CS&T beads, Becton Dickinson) were used daily to monitor the performance of the flow cytometer and verify optical path and stream flow. This procedure enables controlled standardized results and allows the determination of long-term drifts and incidental changes within the flow cytometer. No changes were observed which could affect the results. Compensation beads were used to determine spectral overlap, compensation was automatically calculated using Diva software. Flow cytometry data were analyzed using FACS Diva software.

Flow Cytometry-Based Ex Vivo Lysis Assays in BM-MNCs

BM-MNCs derived from MM patients containing tumor cells, but also autologous effector cells, were used in lysis assays. Sample viability at incubation was more than 98%, as assessed by using 7-AAD (Becton Dickinson). For lysis assays, BM-MNCs were incubated in RPMI+10% fetal bovine serum with control antibody or JNJ-957 (0.0064-4.0 µg/mL) and/or daratumumab (10 µg/mL) in 96-well U-bottom plates for 48 hours. The survival of primary CD138+ MM cells in the BM-MNCs was determined by flow cytometry as previously described (van der Veers et al., *Haematologica*. 2011; 96(2):284-290; van der Veer M S et al., *Blood Cancer J*. 2011; 1(10):e41; Nijhof I S et al., *Leukemia* 2015; 29(10):2039-2049; Nijhof I S, et al., *Blood* 2016; 128(7):959-970.). In both assays, surviving MM cells were enumerated by single platform flow cytometric analysis of CD138+ cells in the presence of Flow-Count Fluorospheres (Beckman Coulter) and LIVE/DEAD Fixable Dead Cell Stain Near-IR fluorescent reactive dye (Invitrogen) to determine absolute numbers of viable MM cells. The percentage of lysis induced by JNJ-957 was then calculated using the following formula: % lysis MM cells=1−(absolute number of surviving CD138+ cells in the presence of JNJ-957/absolute number of surviving CD138+ cells in untreated wells)×100%.

The JNJ-957-induced activation and degranulation of CD4+ and CD8+ T-cells were analyzed by the flow cytometric detection of CD25 and CD107a cell surface expression, respectively.

Flow Cytometry-Based Lysis Assay in MM Cell Lines with PB MNCs as Effector Cells.

BCMA-positive MM cell lines were co-cultured with PB MNCs from healthy donors or MM patients at an effector to target ratio of 9:1 in 96-wells U-bottom plates in the presence of control antibodies or JNJ-957 (0.00256-4.0 µg/mL) for 48 hours. The survival of MM cells was determined by flow cytometry as described above.

Bioluminescence Imaging (BLI)-Based Lysis Assay Using LUC-Transduced MM Cell Lines LUC-transduced MM cell lines were cultured in the presence or absence of pooled BM stromal cells (BMSCs) obtained from newly diagnosed MM patient (n=12) for 16 hours prior to incubation with effector cells (freshly isolated PBMCs from healthy donors) at an effector to target ratio of 9:1, and serial dilutions of JNJ-957 (0.00256-4.0 µg/mL) or control antibodies in 96-well flat bottom plates (Greiner-Bio-One) for 48 hours. The survival of LUC+-MM cells was then determined by BLI, 10 minutes after addition of the substrate luciferin (150 µg/mL; Promega). Lysis of MM cells was determined using the following formula: % lysis=1−(mean BLI signal in the presence of effector cells and JNJ-957/mean BLI signal in the presence of effector cells in untreated wells)×100%.

To evaluate the effect of in vivo pretreatment of PB MNCs with daratumumab monotherapy on efficacy of JNJ-957, the LUC-transduced MM cell line 4 was also co-cultured with PB MNCs, obtained from MM patients before initiation of daratumumab monotherapy and at the time of best response to daratumumab monotherapy (effector to target ratio of 9:1). The BLI assay was performed as described before.

Cytogenetic Analysis

Cytogenetic abnormalities were assessed in purified MM cells by fluorescence in situ hybridization (FISH) and single nucleotide polymorphism (SNP) array. High-risk disease was defined by the presence of del(17p), del(1p), ampl(1q), t(4;14) or t(14;16)[2].

Soluble BCMA Assay

Soluble BCMA (sBCMA) was measured in cell culture supernatants using MSD GOLD™ 96-well Small Spot Streptavidin SECTOR plates (Meso Scale Diagnostics), according to the manufacturer's recommended protocol.

Granzyme B Assay

Granzyme B was measured in cell culture supernatants using MSD R-Plex Granzyme B assay plates (Meso Scale Diagnostics), according to the manufacturer's protocol.

Multiplex Cytokine Assay

Cytokines [interferon-gamma (IFN-γ), interleukin (IL)-2, IL-6, IL-8, IL-10, and tumor necrosis factor-alpha (TNF-α)] in the cell culture supernatants were analyzed using V-Plex proinflammatory Panel 1 Human Kit (Meso Scale Diagnostics), according to the manufacturer's protocol.

Statistics

Comparisons between variables were performed using two-tailed (paired) Student's t-test, or Mann-Whitney U test or Wilcoxon matched-pairs signed-rank test in case the data do not follow a normal distribution. Correlations between variables were made using the Spearman's rank correlation coefficient. P-values below 0.05 were considered significant. In case of combinatorial treatment of JNJ-957 and daratumumab, the expected lysis values were calculated to test the null hypothesis that there is only an additive effect between JNJ-957 and daratumumab, using the following formula: % expected lysis=(% lysis with JNJ-957+% lysis with daratumumab)−(% lysis with JNJ-957×% lysis with daratumumab), as described before[20, 23, 24]. The null hypothesis of "additive effects" was rejected, if the observed values were significantly higher (P<0.05) than the expected values.

Example 1 Anti-BCMA/Anti-CD3 Antibody JNJ-957-Mediated Lysis of BCMA+ Multiple Myeloma Cell Lines is Accompanied by T-Cell Activation and Degranulation Effect of JNJ-957 on mediating lysis of RPMI8226 (FIG. 1), UM9 (FIG. 2), U226 (FIG. 3) and MM1.S (FIG. 4) multiple myeloma cell lines was assessed using healthy donor (HD) peripheral blood mononuclear cells as effector cells over a concentration range of JNJ-957 (0.00128-4.0 µg/mL). JNJ-957 mediated lysis of all tested cell lines in a dose-dependent manner and achieved nearly 100% maximal efficacy at antibody concentration of about 0.1 µg/ml, depending on the cell line as seen in FIG. 1, FIG. 2, FIG. 3 and FIG. 4.

It has previously been shown that BMSCs protect MM cells against various anti-MM agents including daratumumab and MM-reactive T-cells. The potential impact of BMSC-MM cell interactions on the efficacy of JNJ-957 was therefore assessed. The activity of JNJ-957 against the MM cell lines RPMI-8226, UM9 and U266 was not affected by the presence of BMSCs (data not shown). Although JNJ-957-mediated MM cell lysis was modestly inhibited by BMSCs in MM1.S cells at lower concentrations (P<0.0001), this effect was completely abrogated by increasing the JNJ-7957 dose.

Figure 5:
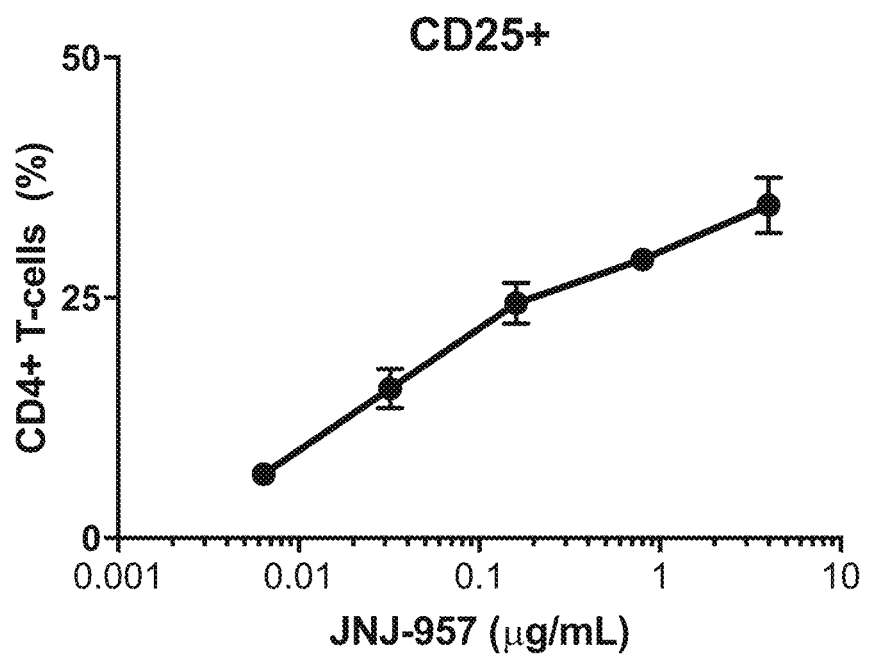
FIG. 5 shows that, in a representative example (n=2) of RPMI 8226 cells incubated with healthy donor PB MNCs, JNJ-957-mediated MM cell lysis was accompanied by CD4$^+$ T cell activation and degranulation as determined by increased surface expression of CD25 (activation).
Figure 6:
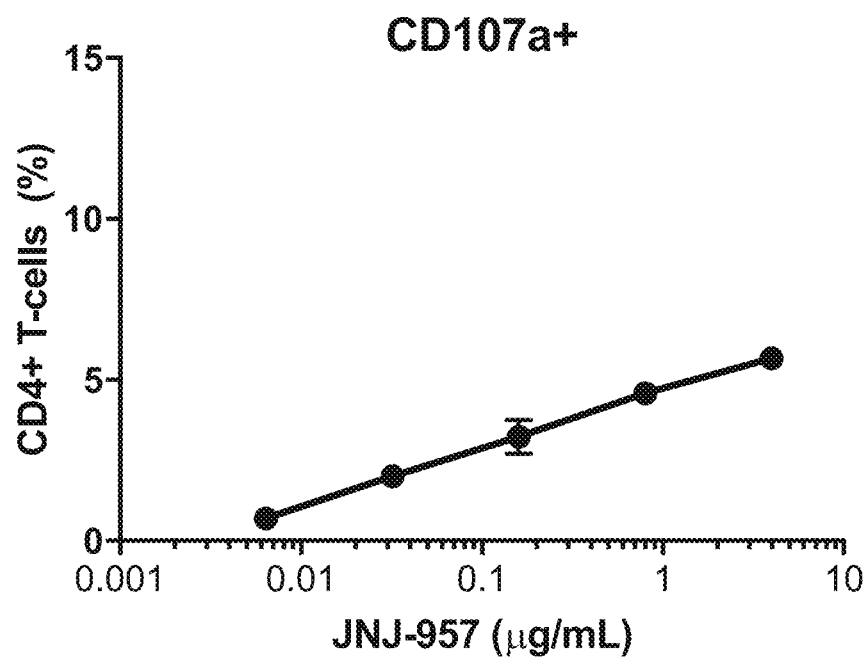
FIG. 6 shows that, in a representative example (n=2) of RPMI 8226 cells incubated with healthy donor PB MNCs, JNJ-957-mediated MM cell lysis was accompanied by CD4$^+$ T cell activation and degranulation as determined by increased surface expression of CD107a (degranulation).
Figure 7:
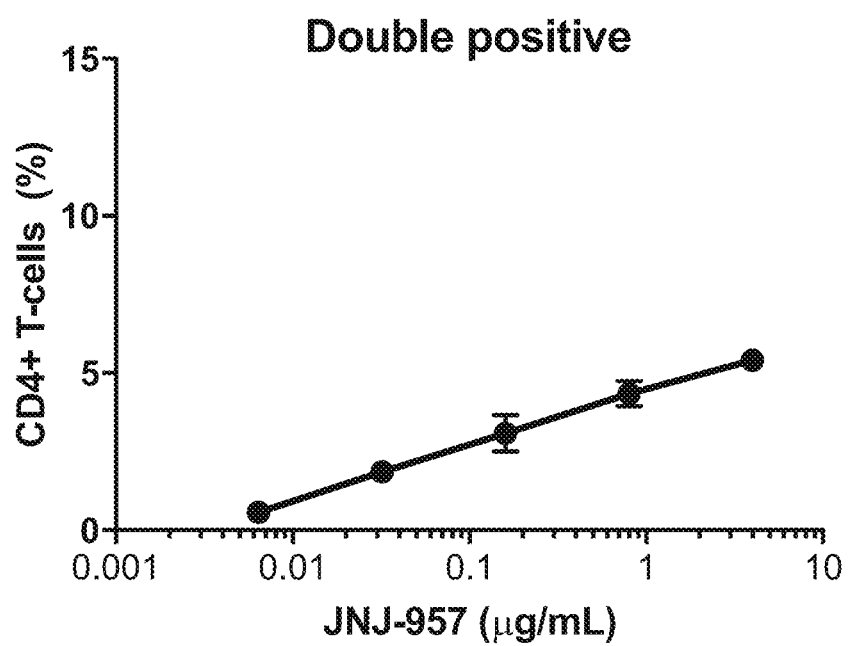
FIG. 7 shows that, in a representative example (n=2) of RPMI 8226 cells incubated with healthy donor PB MNCs, JNJ-957-mediated MM cell lysis was accompanied by CD4$^+$ T cell activation and degranulation as determined by the proportion of CD25 and CD107a double positive CD4+ T cells.
Figure 8:
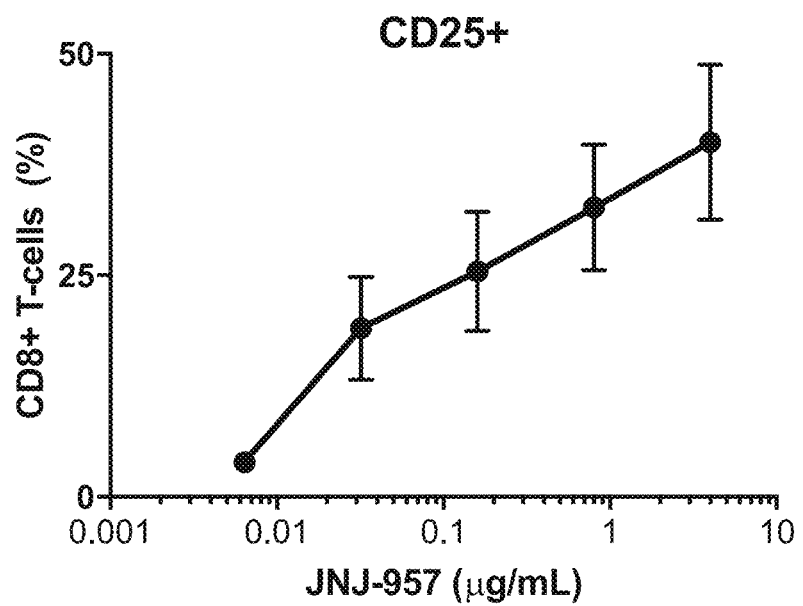
FIG. 8 shows that, in a representative example (n=2) of RPMI 8226 cells incubated with healthy donor PB MNCs, JNJ-957-mediated MM cell lysis was accompanied by CD8$^+$ T cell activation and degranulation as determined by increased surface expression of CD25 (activation).
Figure 9:
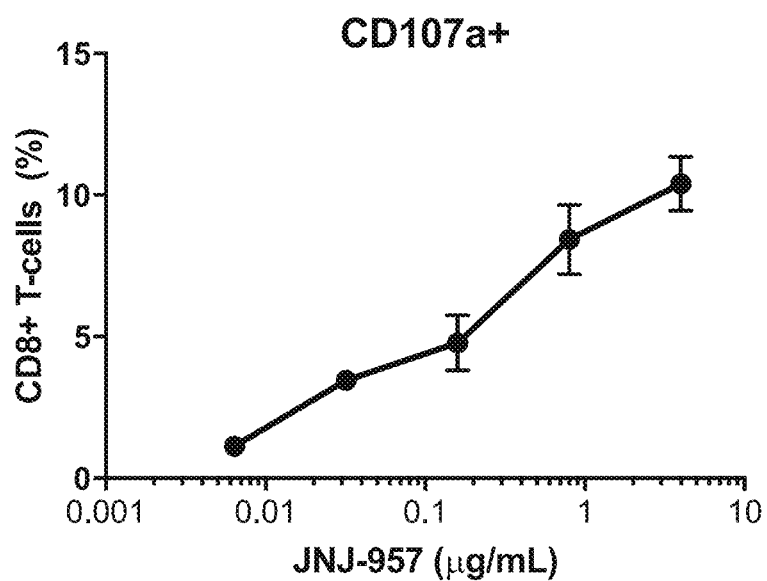
FIG. 9 shows that, in a representative example (n=2) of RPMI 8226 cells incubated with healthy donor PB MNCs, JNJ-957-mediated MM cell lysis was accompanied by CD8$^+$ T cell activation and degranulation as determined by increased surface expression of CD107a (degranulation)
Figure 10:
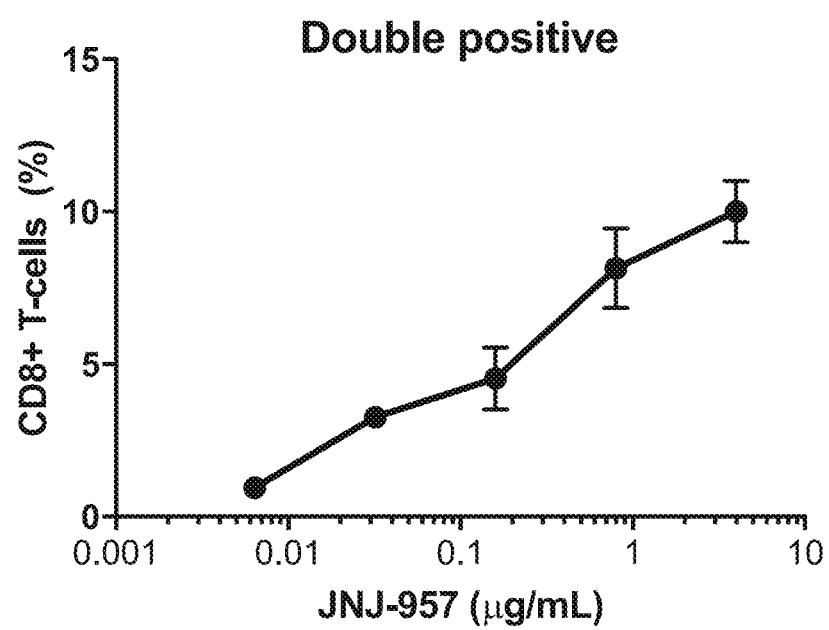
FIG. 10 shows that, in a representative example (n=2) of RPMI 8226 cells incubated with healthy donor PB MNCs, JNJ-957-mediated MM cell lysis was accompanied by CD8$^+$ T cell activation and degranulation as determined by increased proportion of CD25 and CD107a double positive CD4+ T cells.

T cell activation was assessed in RPMI 8226 cell line. Treatment with JNJ-957 resulted in activation and degranulation of both CD4+ and CD8+ T cells in a dose dependent manner, as evidenced by increased cell surface expression of CD25 and CD107a, respectively, or by the proportion of double positive CD25 and CD107a cells. FIG. 5 shows JNJ-957-mediated increase in the percentage of CD25+ CD4 T cells. FIG. 6 shows JNJ-957-mediated increase in the percentage of CD107a+CD4 T cells. FIG. 7 shows JNJ-957-mediated increase in the percentage of the double positive CD25+ CD107+ CD4 T cells. FIG. 8 shows JNJ-957-mediated increase in the percentage of CD25+ CD8 T cells. FIG. 9 shows JNJ-957-mediated increase in the percentage of CD107a+CD8 T cells. FIG. 10 shows JNJ-957-mediated increase in the percentage of the double positive CD25+ CD107+ CD8 T cells.

Example 2 Daratumumab Improved Efficacy of T Cell Redirecting Antibodies Patients BCMA expression levels, composition of immune cells subsets, and ex vivo efficacy of JNJ-957, were assessed in 55 BM aspirates obtained from 11 newly diagnosed MM patients, 21 daratumumab-naïve relapsed/refractory MM patients, and 17 daratumumab-refractory relapsed/refractory MM patients (daratumumab relapsed/refractory patients were enrolled in Phase 1 and Phase 2 study of daratumumab in combination with all-trans retinoic acid (ATRA); clinical trial identifier NCT02751255) and primary plasma cell leukemia (pPCL; n=6). Sequential BM samples were obtained from 8 patients treated in the DARA/ATRA study, directly before initiation of daratumumab monotherapy and at the time of progressive disease during daratumumab treatment. In the same study, we obtained from 10 patients sequential peripheral blood samples, directly before initiation of daratumumab monotherapy and at the time of maximum response achieved with daratumumab.

In the DARA/ATRA study (NCT02751255), patients had MM requiring systemic treatment and were relapsed from or refractory to ≥2 prior lines of therapy. Patients were ≥18 years of age, had a life expectancy of ≥3 months, a WHO performance status of ≤2 and measurable disease.

During the first phase of the study, daratumumab was given according to the recommended dose and schedule (16 mg/kg weekly for 8 weeks, then every 2 weeks for 16 weeks, and every 4 weeks until PD). Study site ethics committees or institutional review boards approved the protocols, which were conducted according to the principles of the Declaration of Helsinki, the International Conference on Harmonization, and the Guidelines for Good Clinical Practice. All patients gave written informed consent.

Baseline characteristics of patients enrolled in Phase 1 and Phase 2 study NCT02751255 is shown in Table 5 and Table 6. RRMM patients had received on average 5 (range 1-9) previous lines of therapies and RRMM dara R patients had received on average 6 (range 3-12) previous lines of therapies. Table 7 shows an updated summary of baseline characteristics of patients enrolled in Phase 1 and Phase 2 study.

TABLE 5

|  | NDMM n = 11 | RRMM n = 19 | RRMM dara R n = 15 |
|---|---|---|---|
| Age, median | 66 | 66 | 68 |
| (range) | (31-80) | (46-77) | (48-80) |
| Sex, male n (%) | 5 (46) | 11 (58) | 9 (60) |
| M-protein, n (%) | | | |
| IgG | 5 (46) | 13 (68) | 11 (73) |
| IgA | 0 | 0 | 2 (13) |
| FLC only | 6 (55) | 6 (32) | 2 (13) |

NDMM: newly diagnosed multiple myeloma
RRMM: relapsed/refractory multiple myeloma
RRMM: daraR daratumumab refractory multiple myeloma

TABLE 6

|  | RRMM n = 19 | | RRMM dara R n = 15 | |
|---|---|---|---|---|
| Previous lines, n (range) | 5 (1-9) | | 6 (3-12) | |
|  | Exposed n (%) | Refractory n (%) | Exposed n (%) | Refractory n (%) |
| Lenalidomide | 16 (84) | 16 (84) | 15 (100) | 15 (100) |
| Bortezomib | 14 (74) | 14 (74) | 14 (93) | 9 (60) |
| Pomalidomide | 12 (63) | 12 (63) | 10 (67) | 10 (67) |
| Carfilzomib | 5 (21) | 4 (21) | 4 (26) | 4 (26) |
| Daratumumab | 0 | 0 | 15 (100) | 15 (100) |

TABLE 7

| Parameter | NDMM n = 11 | RRMM patients, dara-naïve n = 21 | RRMM patients, dara-refractory n = 17 | pPCL n = 6 |
|---|---|---|---|---|
| Median age, years (range) | 66 (31-80) | 66 (46-77) | 68 (48-80) | 65 (57-98) |
| Sex, male, n (%) | 5 (45) | 11 (52) | 9 (53) | 2 (33) |
| M-protein type | | | | |
| IgG, n (%) | 5 (45) | 15 (71) | 13 (76) | 2 (33) |
| IgA, n (%) | 0 | 1 (5) | 2 (12) | 0 |
| FLC only, n (%) | 6 (55) | 5 (24) | 2 (12) | 3 (50) |
| Unknown | 0 | 0 | 0 | 1 (17) |
| Cytogenetics, n (%) | | | | |
| High risk* | 5 (45) | 12 (57) | 9 (53) | 3 (50) |
| Standard risk | 5 (45) | 7 (33) | 5 (29) | 1 (17) |
| Not assessed | 1 (9) | 2 (10) | 3 (18) | 2 (33) |
| Previous lines of therapy, n (range) | 0 | 3 (1-9) | 6 (3-12) | 0 |
| Most recent treatment | | | | |
| No treatment | 11 (100) | 0 | 0 | 6 (100) |
| PI based | 0 | 2 (10) | 0 | 0 |
| IMiD based | 0 | 15 (71) | 1 (6)# | 0 |
| PI + IMiD | 0 | 4 (19) | 1 (6)# | 0 |
| Daratumumab | 0 | 0 | 15 (88) | 0 |
| Lenalidomide | | | | |
| exposed, n (%) | n.a. | 19 (90)§ | 17 (100) | n.a. |
| refractory**, n (%) | | 18 (86) | 17 (100) | |
| Bortezomib | | | | |
| exposed, n (%) | n.a. | 17 (81)† | 16 (94)‡ | n.a. |
| refractory**, n (%) | | 10 (48) | 11 (65) | |
| Pomalidomide refractory**, n (%) | n.a. | 13 (62) | 10 (59) | n.a. |
| Carfilzomib refractory**, n (%) | n.a. | 4 (19) | 4 (24) | n.a. |

TABLE 7-continued

| Parameter | NDMM n = 11 | RRMM patients, dara-naïve n = 21 | RRMM patients, dara-refractory n = 17 | pPCL n = 6 |
|---|---|---|---|---|
| Daratumumab refractory**, n (%) | n.a. | 0 | 17 (100) | n.a. |
| Elotuzumab refractory**, n (%) | n.a. | 2 (10) | 1 (6) | n.a. |
| Ixazomib refractory**, n (%) | n.a. | 1 (5) | 1 (6) | n.a. |

*High-risk disease was defined by the presence of del(17p), del(1p), ampl(1q), t(4;14) or t(14;16).
**Refractory disease is defined as progressive disease during therapy, no response (less than PR), or progressive disease within 60 days of stopping treatment, according to the International Uniform Response Criteria for Multiple Myeloma.
BM aspirates were obtained immediately at the time of development of progressive disease during daratumumab monotherapy (n = 15), while 2 BM samples were obtained 22 and 48 months after development of progression during daratumumab monotherapy, after 3 and 5 other lines of treatment, respectively.
§Additionally, 1 out of 19 patients was lenalidomide intolerant;
†Additionally, 4 out of 17 patients were bortezomib intolerant;
‡Additionally, 3 out of 16 patients were bortezomib intolerant;
Abbreviations:
MM, multiple myeloma;
NDMM, newly diagnosed MM;
RRMM, relapsed/refractory MM;
Dara, daratumumab;
pPCL, primary plasma cell leukemia;
n, number;
IgG, immunoglobulin G;
IgA, immunoglobulin A;
FLC, free light chain;
del, deletion;
amp, amplification;
t, translocation;
PI, proteasome inhibitor;
IMiD, immunomodulatory drug;

Results

Figure 11:
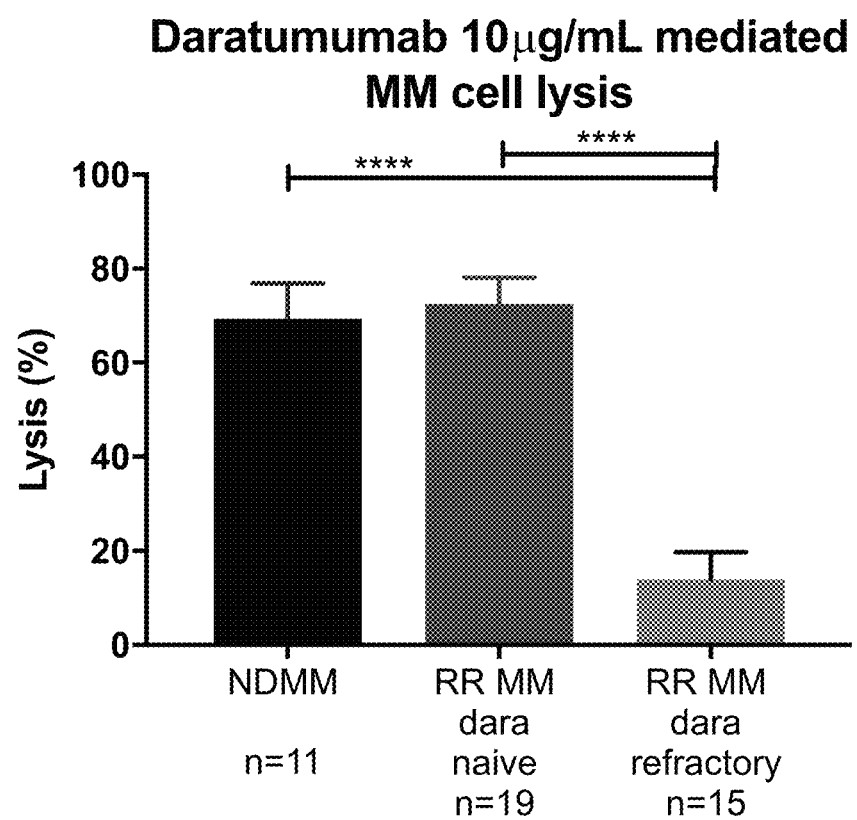
FIG. 11 shows the in vitro daratumumab-mediated lysis of MM cells from newly diagnosed multiple myeloma (NDMM) and daratumumab naïve relapsed/refractory MM (RRMM) patients. Multiple myeloma cells from daratumumab refractory RRMM patients were resistant to daratumumab-mediated lysis ****P<0.0001

Daratumumab mediated efficient lysis of MM cells from newly diagnosed (NDMM) and relapsed/refractory daratumumab naïve patients while cells from RRMM daratumumab refractory patients were resistant to lysis (FIG. 11).

Figure 12:
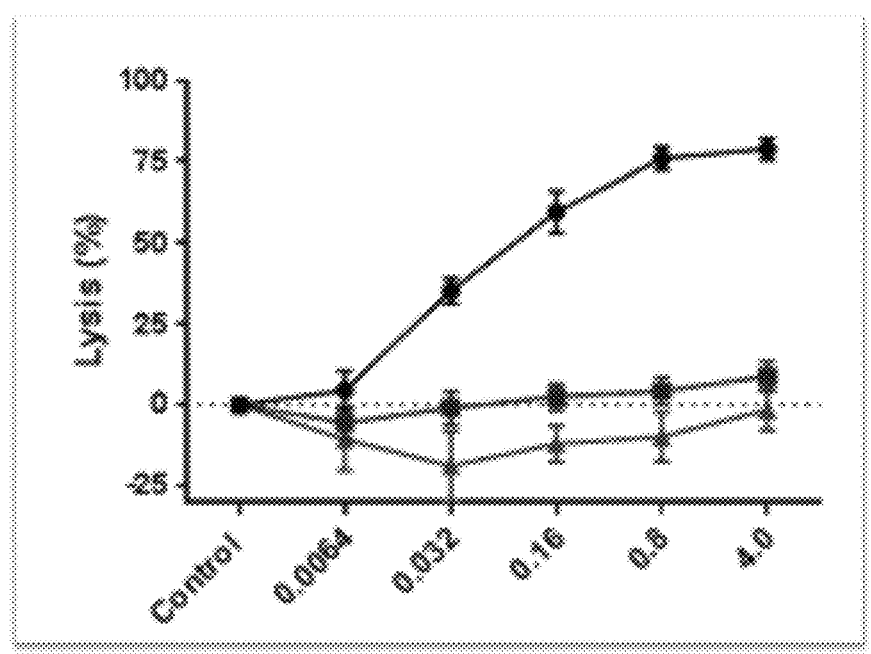
FIG. 12 shows the dose response of JNJ-957-mediated lysis of plasma cells, T cell and NK cells in fully autologous bone marrow (BM) MNCs obtained from newly diagnosed multiple myeloma patients (NDMM, n=8). Percent lysis was measured at various antibody concentrations (0.0064-4.0 μg/mL) as indicated in the Figure. Circles (Top line): plasma cells; Squares (Middle line): T cells; Triangles (Bottom line): NK cells.
Figure 13:
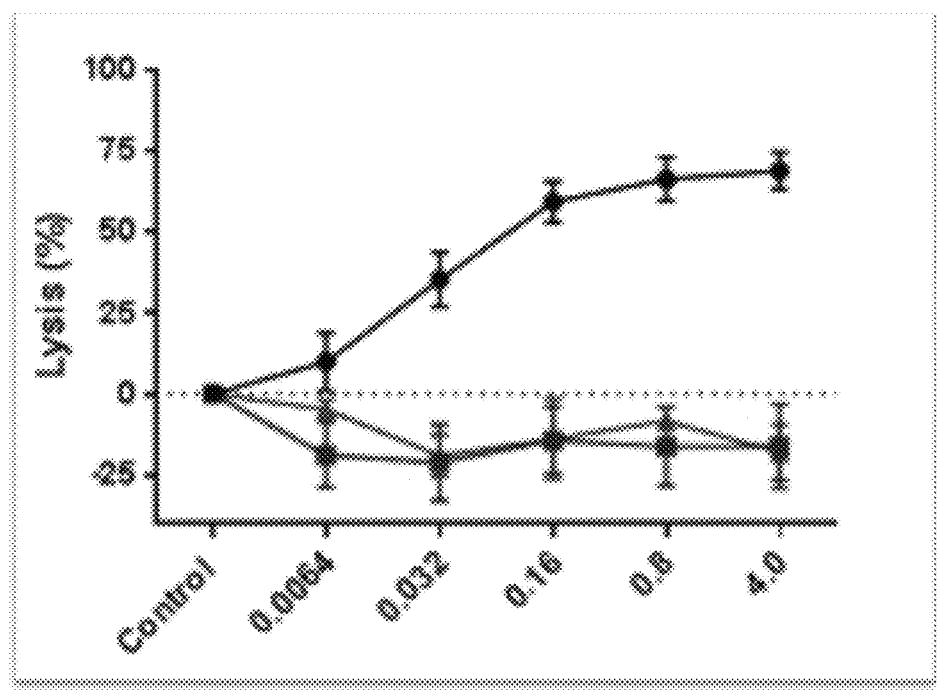
FIG. 13 shows the dose response of JNJ-957-mediated lysis of plasma, T cell and NK cells in fully autologous bone marrow (BM) MNCs obtained from multiple myeloma (MM) patients who were refractory to lenalidomide treatment (n=15). Percent lysis was measured at various antibody concentrations (0.0064-4.0 μg/mL) as indicated in the Figure. Circles (Top line): plasma cells; Squares (Middle line): T cells; Triangles (Bottom line): NK cells.
Figure 14:
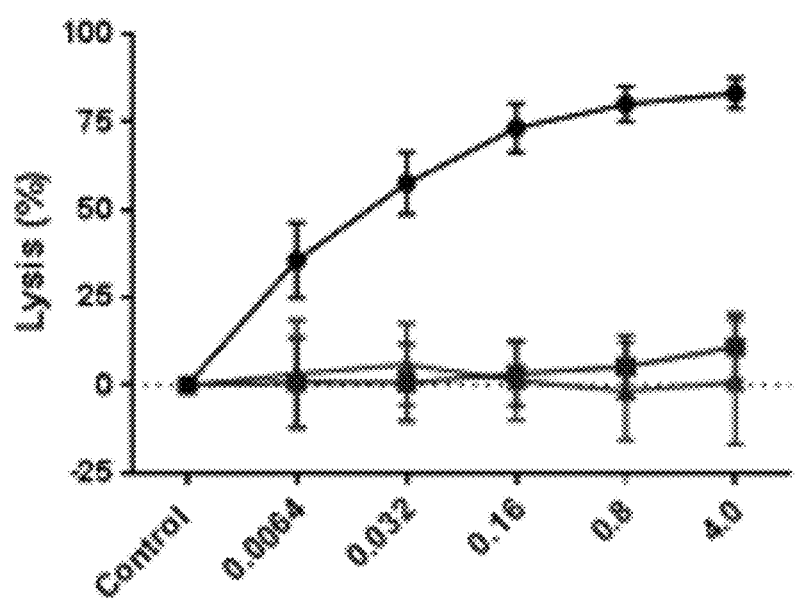
FIG. 14 shows the dose response of JNJ-957-mediated lysis of plasma, T cell and NK cells in fully autologous bone marrow (BM) MNCs obtained from MM patients who were refractory to treatment with lenalidomide and daratumumab (n=11). Percent lysis was measured at various antibody concentrations (0.0064-4.0 μg/mL) as indicated in the Figure. Circles (Top line): plasma cells; Squares (Middle line): T cells; Triangles (Bottom line): NK cells.

In newly diagnosed (ND) MM patient samples (n=8), the mean lysis of MM cells by JNJ-957 4.0 µg/mL was 79% (range: 66-92%; FIG. 12) Similar MM lysis, but with a larger variation, was achieved in lenalidomide (LEN) refractory patient samples (n=15; mean lysis at 4.0 µg/mL: 69%; range: 24-98%; FIG. 13), who were also bortezomib (73%), pomalidomide (82%) and carfilzomib (9%) refractory. JNJ-957 was also effective in samples from MM patients who were daratumumab (DARA) refractory (n=11; mean lysis at 4.0 µg/mL: 83%; range: 52-99%; FIG. 14). NK- and T-cell frequencies were not affected in any of the samples tested.

The CD3xnull and BCMAxnull control antibodies showed significantly lower activity in the different patient samples, when compared to JNJ-957, indicating the requirement for cross-linking of the MM cell and the effector T-cells, as well as absence of a direct effect of BCMA blockade.

Figure 15:
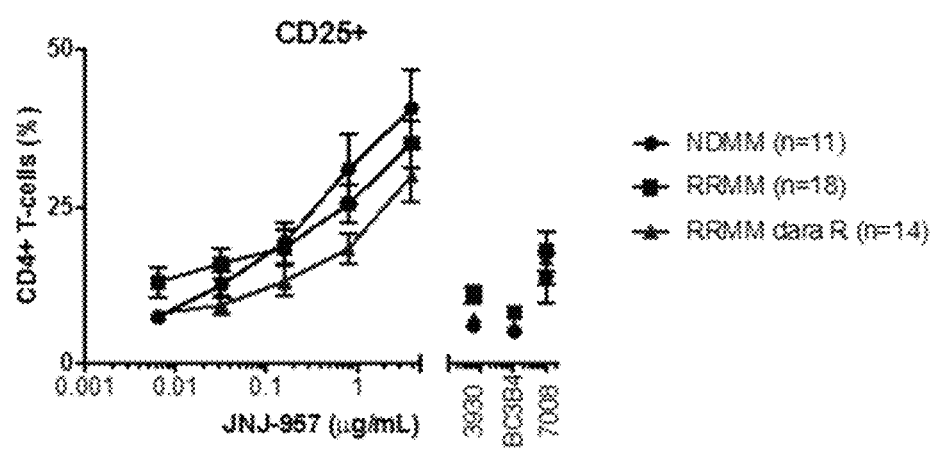
FIG. 15 shows that JNJ-957-mediated MM cell lysis was accompanied by activation (as assessed by increased CD25 surface expression) of CD4$^+$ T cells in the BM samples from NDMM, daratumumab naïve RRMM (RRMM) and daratumumab refractory RRMM (RRMM daraR) patients. 3930: Isotype control; BC3B4: BCMAxnull bispecific antibody; 7008: nullxCD3 bispecific antibody.
Figure 16:
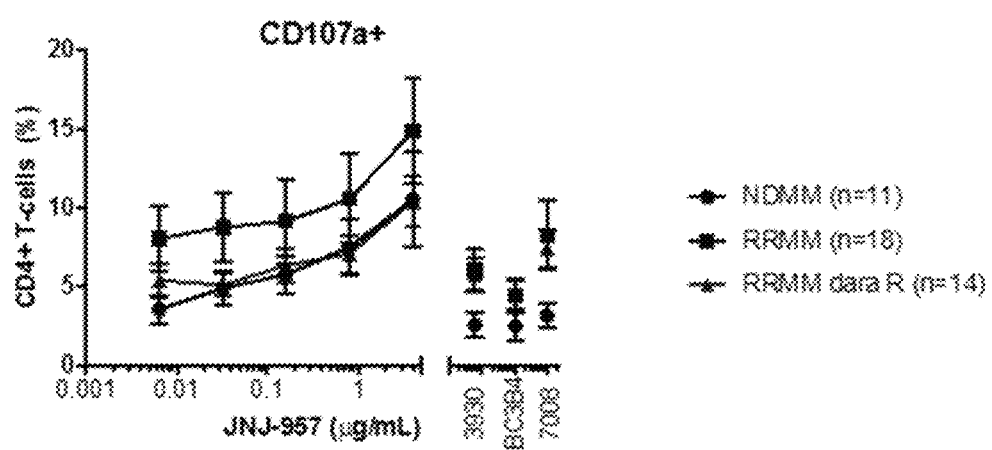
FIG. 16 shows that JNJ-957-mediated MM cell lysis was accompanied by degranulation (as assessed by increased CD107a surface expression) of CD4$^+$ T cells in the BM samples from NDMM, daratumumab naïve RRMM (RRMM) and daratumumab refractory RRMM (RRMM daraR) patients. 3930: Isotype control; BC3B4: BCMAxnull bispecific antibody; 7008: nullxCD3 bispecific antibody.
Figure 17:
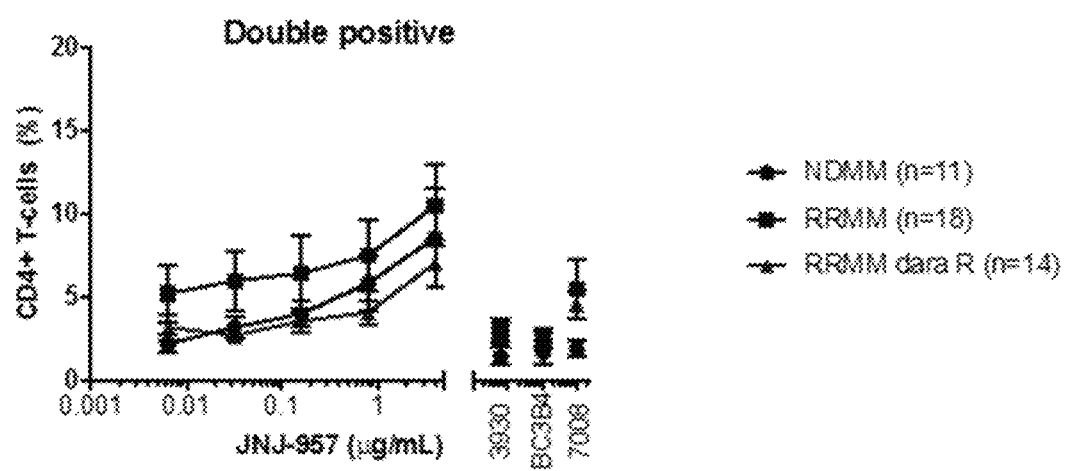
FIG. 17 shows the double positive CD25$^+$CD107a$^+$ cells as a percentage of CD4$^+$ T cells in the BM samples from NDMM, daratumumab naïve RRMM (RRMM) and daratumumab refractory RRMM (RRMM daraR) patients treated with JNJ-957 at indicated concentrations. 3930: Isotype control; BC3B4: BCMAxnull bispecific antibody; 7008: nullxCD3 bispecific antibody. Double positive: CD25 and CD107a double positive CD4$^+$ T cells.
Figure 18:
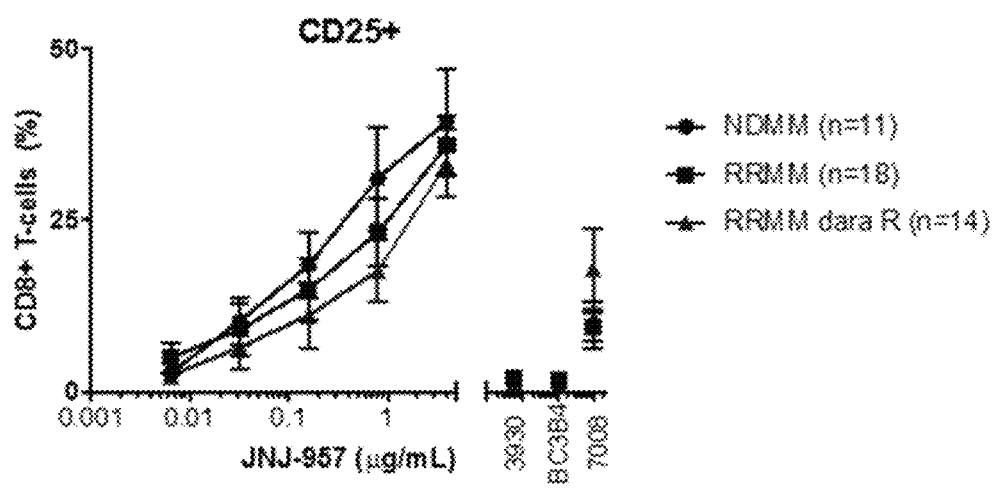
FIG. 18 shows that JNJ-957-mediated MM cell lysis was accompanied by activation (as assessed by increased CD25 surface expression) of CD8$^+$ T cells in the BM samples from NDMM, daratumumab naïve RRMM (RRMM) and daratumumab refractory RRMM (RRMM daraR) patients. 3930: Isotype control; BC3B4: BCMAxnull bispecific antibody; 7008: nullxCD3 bispecific antibody.
Figure 19:
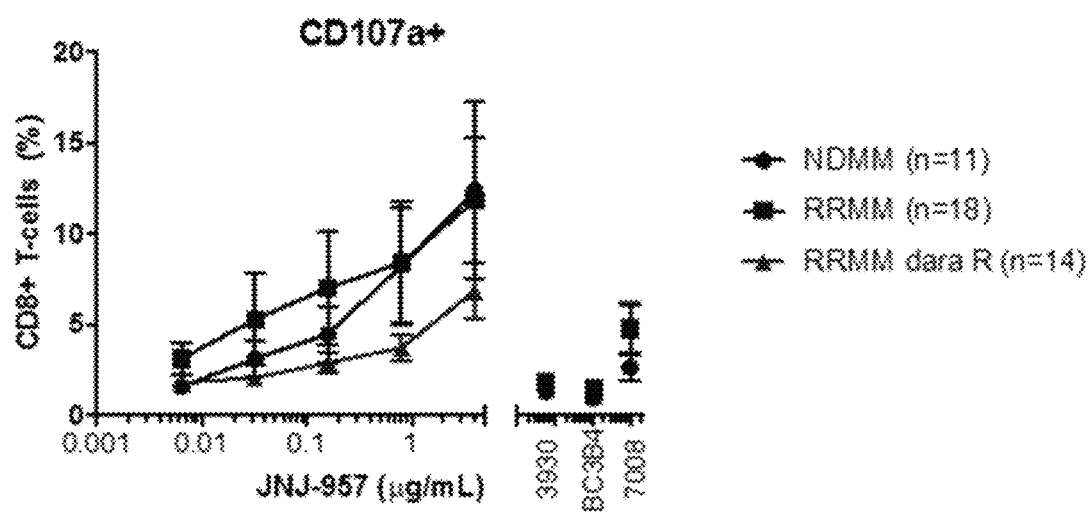
FIG. 19 shows that JNJ-957-mediated MM cell lysis was accompanied by degranulation (as assessed by increased CD107a surface expression) of CD8$^+$ T cells in the BM samples from NDMM, daratumumab naïve RRMM (RRMM) and daratumumab refractory RRMM (RRMM daraR) patients. 3930: Isotype control; BC3B4: BCMAxnull bispecific antibody; 7008: nullxCD3 bispecific antibody.
Figure 20:
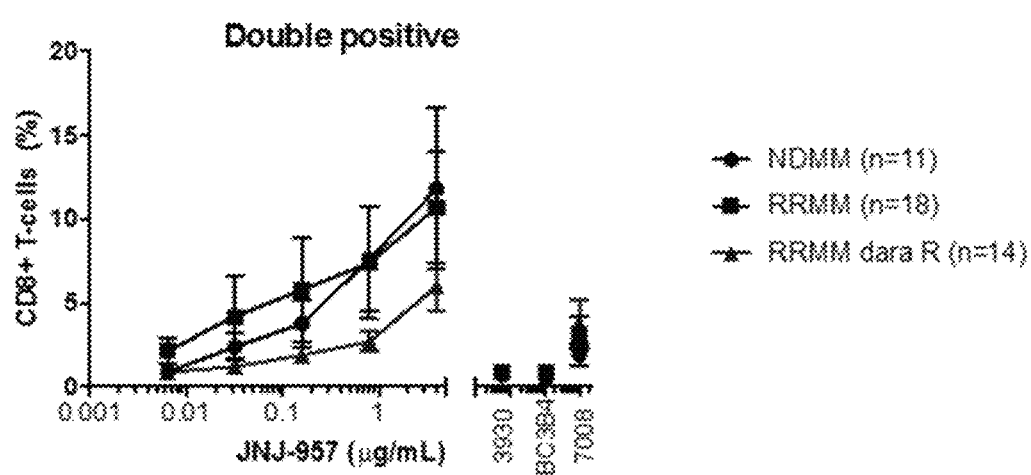
FIG. 20 shows the double positive CD25$^+$CD107a$^+$ cells as a percentage of CD8$^+$ T cells in the BM samples from NDMM, daratumumab naïve RRMM (RRMM) and daratumumab refractory RRMM (RRMM daraR) patients treated with JNJ-957 at indicated concentrations. 3930: Isotype control; BC3B4: BCMAxnull bispecific antibody; 7008: nullxCD3 bispecific antibody. Double positive: CD25 and CD107a double positive CD8$^+$ T cells.

JNJ-957 mediated lysis of primary MM cells was associated with a dose-dependent increase in the percentage of activated CD4$^+$ and CD8$^+$ T-cells, as assessed by the expression of CD25 activation antigen. JNJ-957 treatment also resulted in degranulation of CD4$^+$ and CD8$^+$ T-cells, as determined by cell surface expression of CD107a. There was no difference in extent of T-cell activation and degranulation between NDMM, daratumumab-naïve RRMM and daratumumab-refractory RRMM patients. FIG. 15 shows JNJ-957-mediated increase in the percentage of CD25+ CD4 T cells. FIG. 16 shows JNJ-957-mediated increase in the percentage of CD107a+CD4 T cells. FIG. 17 shows JNJ-957-mediated increase in the percentage of the double positive CD25+ CD107+ CD4 T cells. FIG. 18 shows JNJ-957-mediated increase in the percentage of CD25+ CD8 T cells. FIG. 19 shows JNJ-957-mediated increase in the percentage of CD107a+CD8 T cells. FIG. 20 shows JNJ-957-mediated increase in the percentage of the double positive CD25+ CD107+ CD8 T cells.

Levels of granzyme B and various cytokines in the supernatant of the JNJ-957-treated BM-MNCs from daratumumab-naïve and daratumumab-refractory RRMM patients was also assessed. JNJ-957-mediated T-cell activation resulted in a dose-dependent increase in levels of granzyme B, IFN-γ, IL-2, IL-6, IL-8, IL-10, and TNF-α (data not shown).

Figure 21:
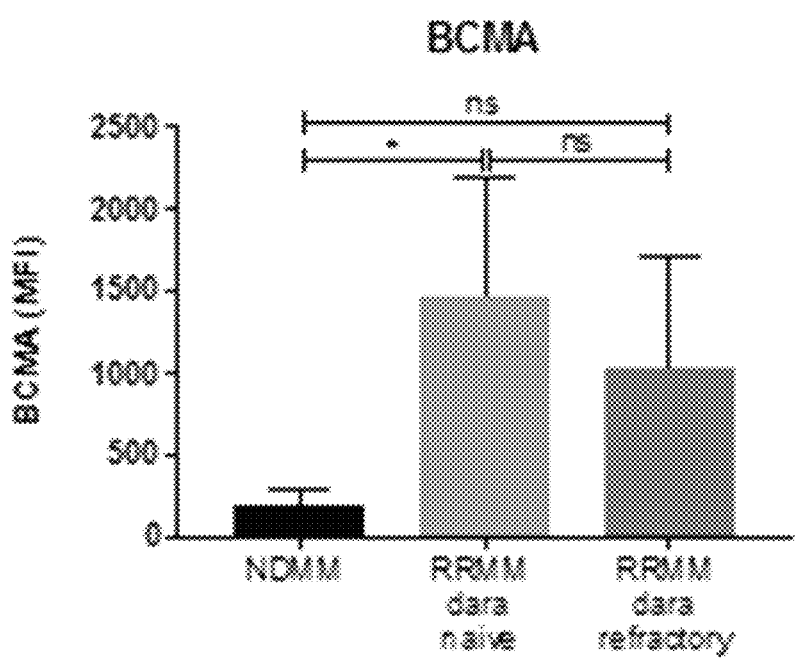
FIG. 21 shows BCMA expression levels on MM cells (mean MFI±SEM) in NDMM, daratumumab naïve RRMM and daratumumab refractory RRMM subjects. P-values between the indicated groups were calculated using Mann-Whitney U test; *P<0.05; ns: not significant.
Figure 22:
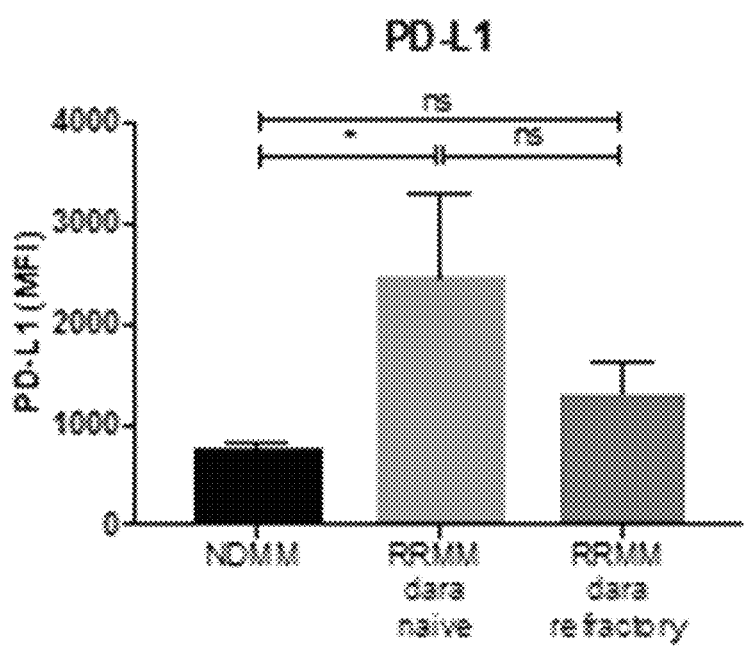
FIG. 22 shows PD-L1 expression levels on MM cells (mean MFI±SEM) in NDMM, daratumumab naïve RRMM and daratumumab refractory RRMM subjects. P-values between the indicated groups were calculated using Mann-Whitney U test; *P<0.05; ns: not significant.

JNJ-957 efficacy in mediating MM cell killing was neither associated with tumor characteristics (BCMA or PD-L1 expression, the presence of standard or high-risk cytogenetic abnormalities) nor patient's characteristics such as effector: target ratio, composition of T-cell system or PD-1/HLA-DR expression on T-cells across all BM samples. However, when patient categories were analyzed separately, BCMA (FIG. 21) and PD-L1 (FIG. 22) expression levels were significantly higher in RRMM patients, compared to NDMM patients, irrespective of daratumumab exposure. Although patient numbers were small, the activity of JNJ-957 was inversely correlated with PD-L1 expression levels in daratumumab-naïve RRMM patients (P=0.045).

The composition of the immune cells in the BM aspirates NDMM, daratumumab naïve RRMM and daratumumab RRMM samples were evaluated to gain understanding on the differential effect of JNJ-957 in samples obtained from the three patient subgroups. In the combined group of patients, a high T-cell frequency (P=0.034) and high E:T ratio (P=0.029) were associated with enhanced JNJ-7957-mediated lysis of MM cells. Other immune parameters (number of T-cells, Tregs, PD-1$^+$ T cells, HLA-DR$^+$ T cells or naïve T cells) did not affect JNJ-7957 mediated MM cell lysis.

Figure 23:
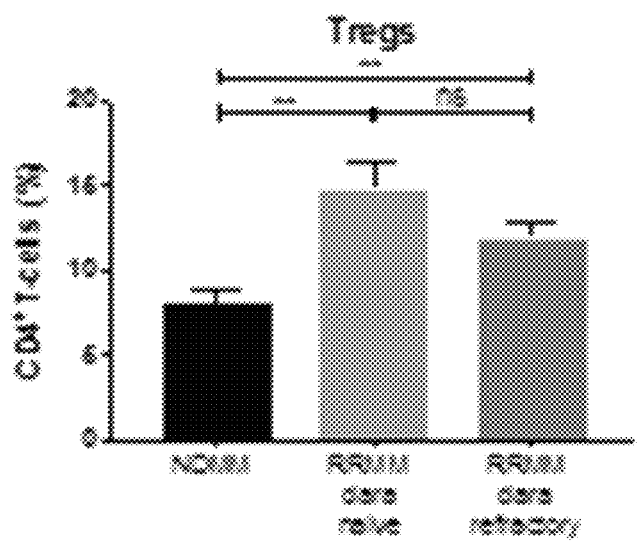
FIG. 23 shows the baseline percentage of Tregs in BM MNCs from NDMM, daratumumab naïve RRMM and daratumumab refractory RRMM. **p<0.01; ns: not significant.
Figure 24:
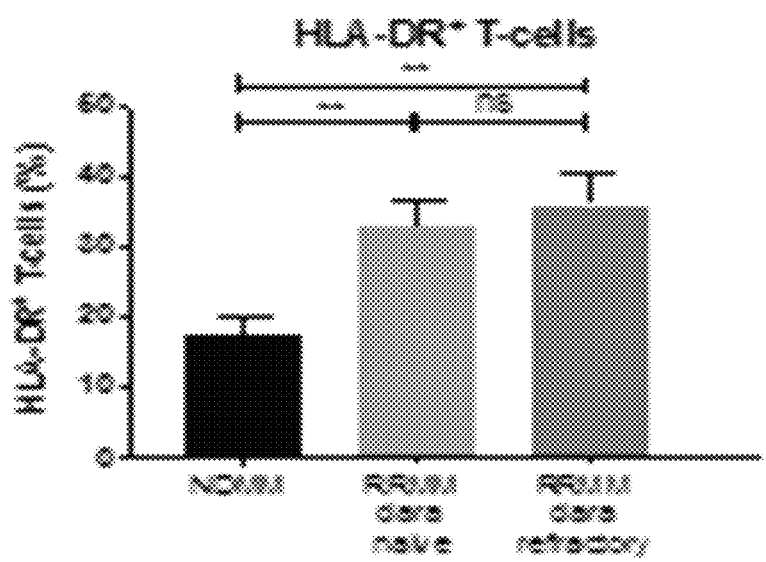
FIG. 24 shows the baseline percentage of activated T cells (as assessed by HLA-DR positivity) in BM MNCs from NDMM, daratumumab naïve RRMM and daratumumab refractory RRMM. **p<0.01; ns: not significant.
Figure 25:
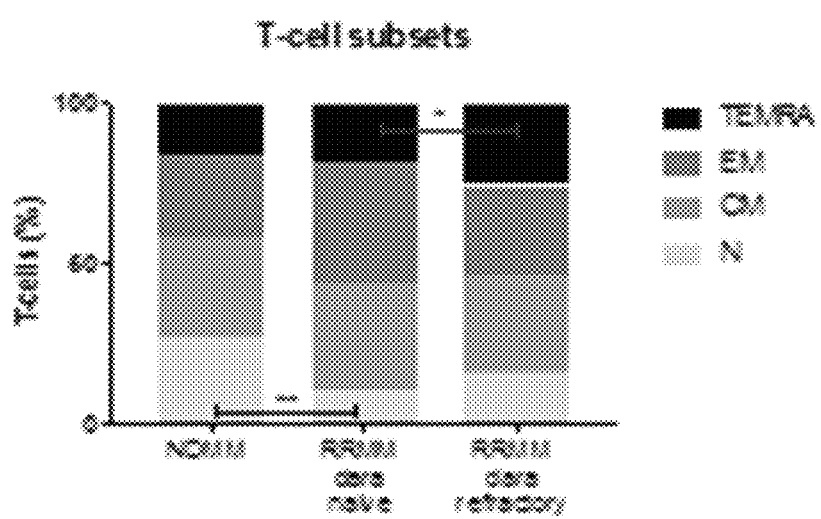
FIG. 25 shows the baseline percentage of the various T cell subsets in BM MNCs from NDMM, daratumumab naïve RRMM and daratumumab refractory RRMM. *p<0.05; **p<0.01; Ns: not significant. TEMRA: CD45RA$^+$CCR7-T cells; EM: effector memory CM: central memory; N: naïve T cells.
Figure 26:
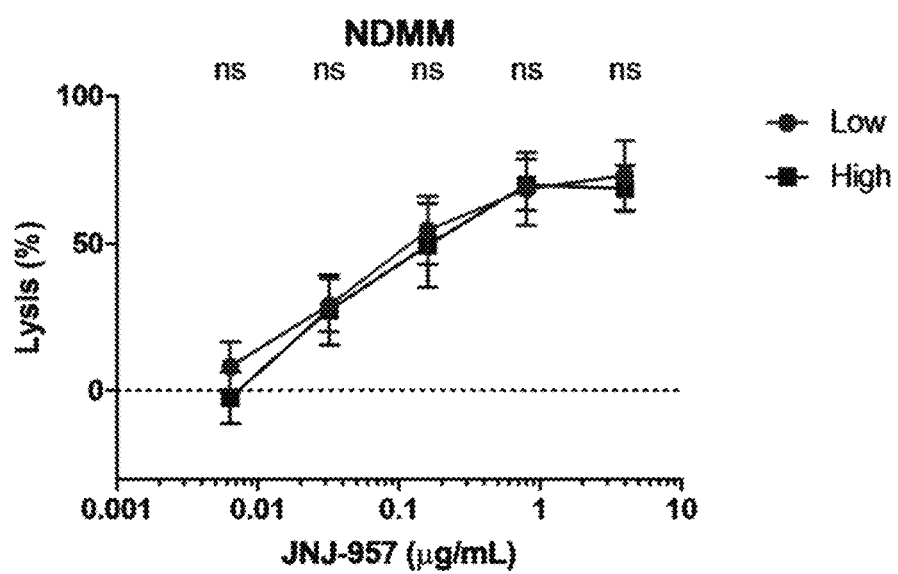
FIG. 26 shows JNJ-957-mediated lysis of multiple myeloma cells from NDMM patients mediated by autologous BM MNCs. Samples were dichotomized for the frequency of Tregs at baseline (low ≤50$^{th}$ percentile, high >50$^{th}$ percentile). Ns: not significant.
Figure 27:
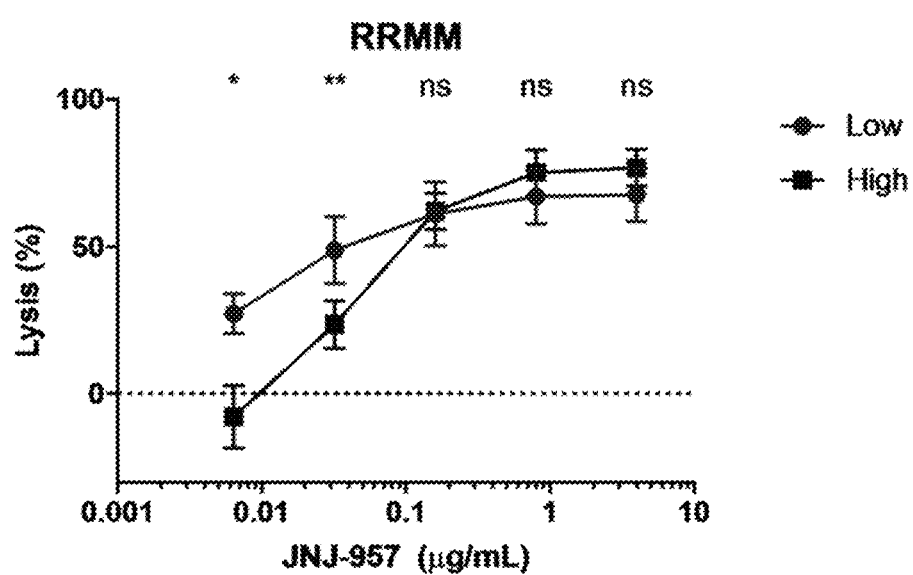
FIG. 27 shows JNJ-957-mediated lysis of multiple myeloma cells from daratumumab naïve RRMM patients mediated by autologous BM MNCs. Samples were dichotomized for the frequency of Tregs at baseline (low ≤50$^{th}$ percentile, high >50$^{th}$ percentile). *p<0.05; **p<0.01; Ns: not significant.
Figure 28:
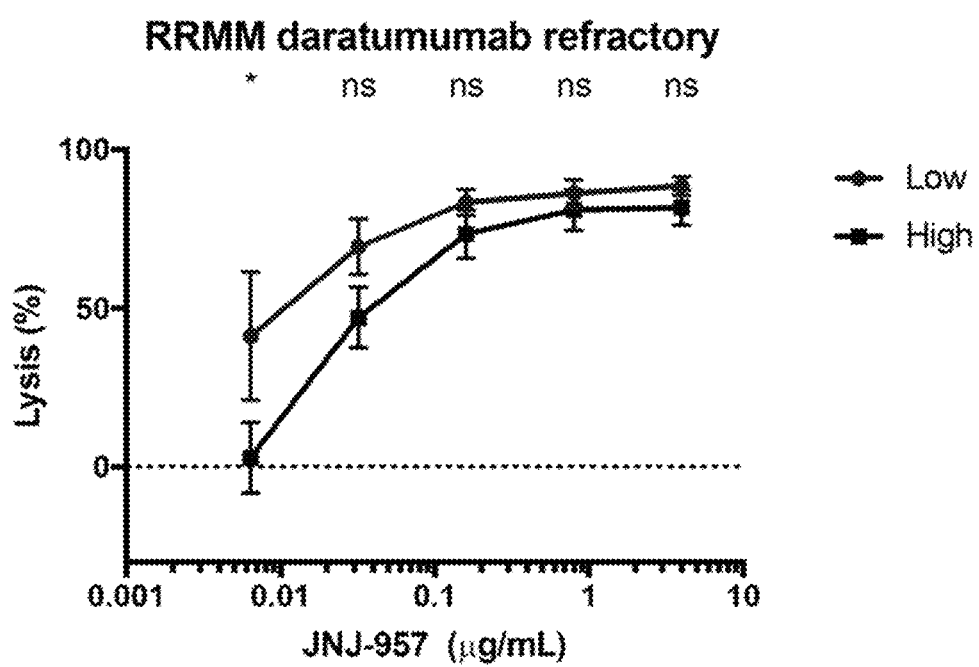
FIG. 28 shows JNJ-957-mediated lysis of multiple myeloma cells from daratumumab refractory RRMM patients mediated by autologous BM MNCs. Samples were dichotomized for the frequency of Tregs at baseline (low ≤50$^{th}$ percentile, high >50$^{th}$ percentile). *p<0.05; ns: not significant.

In the subgroup analysis, RRMM patients had a significantly higher frequency of Tregs (FIG. 23) and activated T-cells (defined by expression of HLA-DR) (FIG. 24), and a lower frequency of naïve T-cells, when compared to NDMM patients. In addition, daratumumab-refractory patient samples contained significantly more TEMRA T-cells than daratumumab-naïve samples (FIG. 25). However, frequencies of activated, naïve, central memory (CM), effector memory (EM) or TEMRA T-cells were not associated with response to JNJ-7957 in this subgroup analysis. A high baseline percentage of Tregs showed a negative influence on JNJ-957 mediated MM cell lysis in RRMM patient samples, which was overcome by optimal dosing. JNJ-597-mediated lysis of NDMM (FIG. 26), daratumumab naïve RRMM (FIG. 27) and daratumumab refractory RRMM (FIG. 28) patient samples mediated by autologous effector cells, dichotomized according to baseline percentage of Tregs was assessed. The $50^{th}$ percentile was used to categorize samples as "low" or "high" in terms of Treg content: NDMM: low: ≤7.34%, high: >7.34%. Daratumumab naïve RRMM: low ≤15.57%, high >15.57%. Daratumumab refractory RRMM: low ≤11.24%, high >11.24%. Higher Treg concentration dampened JNJ-957-mediated lysis of MM cells in daratumumab naïve RRMM and daratumumab refractory RRMM samples. The Treg effect was abrogated at higher JNJ-957 concentrations.

The proportion of PD-1$^+$ T-cells and E:T ratio were similar in the three patient groups. Only in NDMM patients, a low frequency of T-cells (P=0.010) and a high frequency of PD-1$^+$ T-cells (P=0.048) impaired JNJ-957-mediated lysis of MM cells (data not shown).

Figure 29:
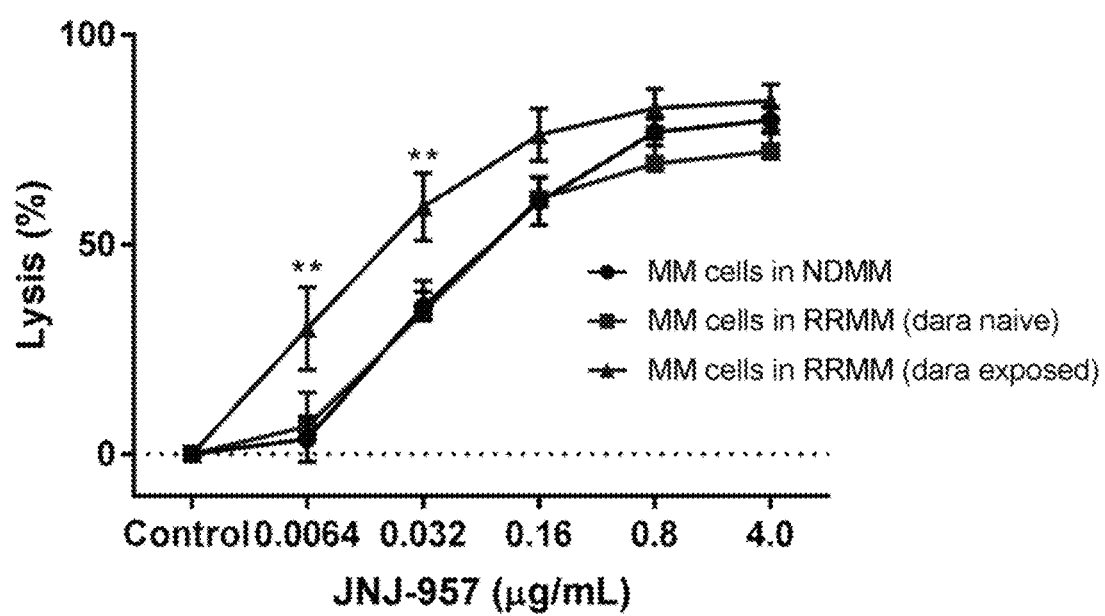
FIG. 29 shows JNJ-957-mediated lysis of MM cells from BM samples from NDMM (n=9), daratumumab naïve RRMM (n=18) and daratumumab-refractory RRMM (n=13) patients after a 48-hour incubation. Data was depicted as mean±SEM, P values were calculated using student t-test. **P<0.01

The effect of daratumumab treatment to JNJ-957 efficacy was evaluated by assessing JNJ-957-mediated lysis in BM samples from NDMM (n=9), daratumumab naïve RRMM (n=18) and daratumumab-refractory RRMM (n=13) patients after a 48-hour incubation. At relatively low concentrations of JNJ-957 (0.0064-0.032 µg/mL), tumor cell lysis was significantly better in the daratumumab-exposed patients, as compared to both daratumumab naïve RRMM and NDMM patients. FIG. 29 shows the percentage lysis in the patient populations. Data are depicted as mean±SEM, P values are calculated using student t-test.

Figure 30:
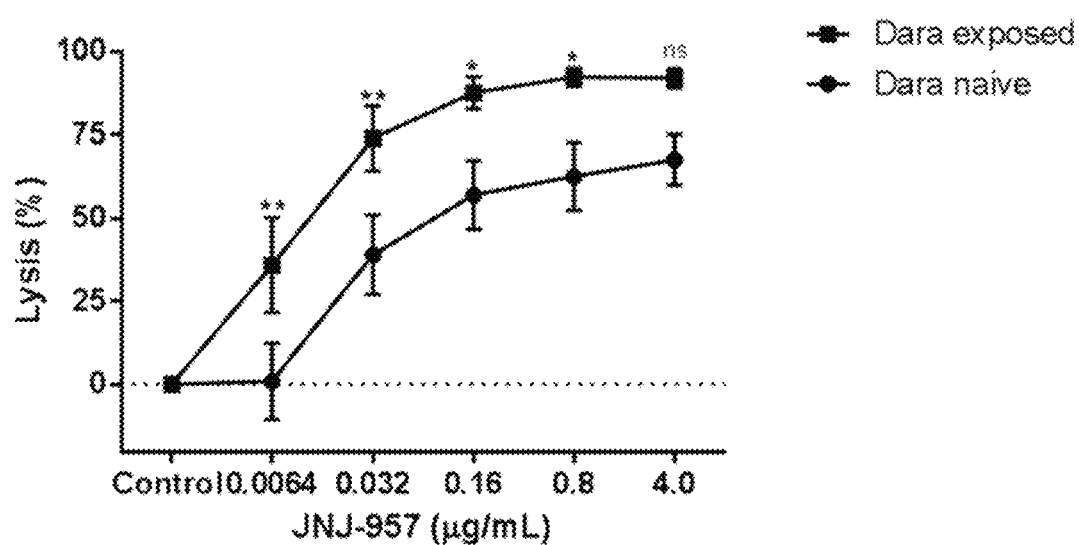
FIG. 30 shows that JNJ-957-mediated lysis of MM cells from bone marrow (BM) samples obtained from relapsed/refractory multiple myeloma patients (RRMM) (n=8) was augmented in samples from patients who had received daratumumab ("Dara exposed") when compared to samples from the same patients before initiation of daratumumab treatment ("Dara naïve"). Data was depicted as mean±SEM; P values were calculated using a paired t-test. ns: not significant; *P<0.05, **P<0.01.
Figure 31:
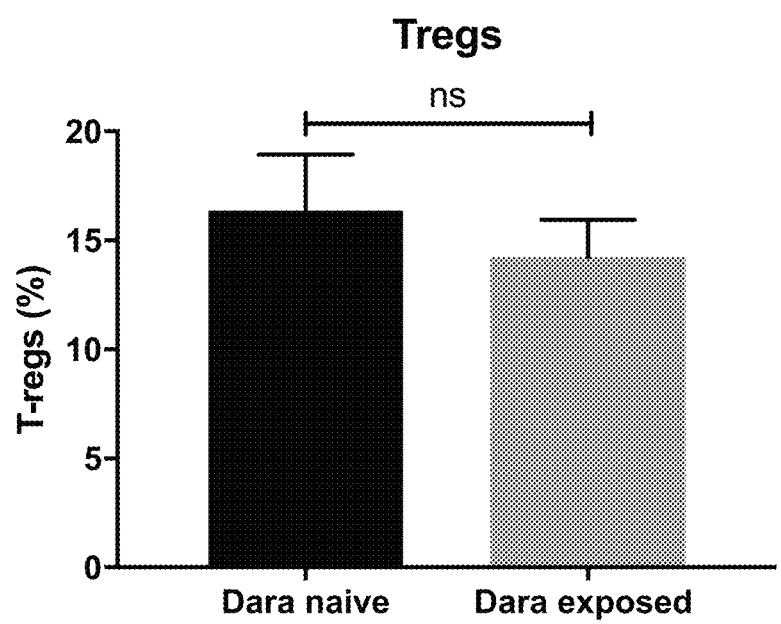
FIG. 31 shows the percentage of Tregs in the sequential BM aspirates from RRMM patients before initiation of daratumumab (before dara) and at development of daratumumab refractory disease (dara exposed). ns: not significant.
Figure 32:
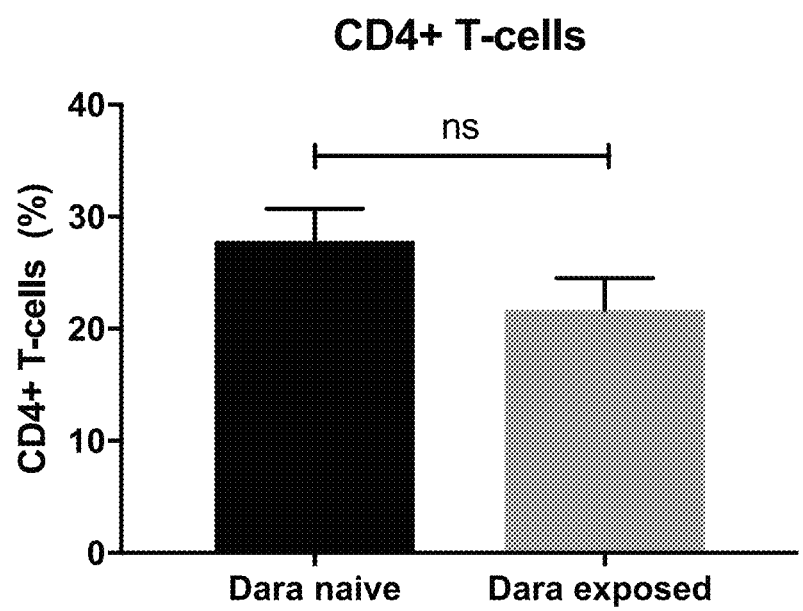
FIG. 32 shows the percentage of CD4$^+$ cells in the sequential BM aspirates from RRMM patients before initiation of daratumumab (before dara) and at development of daratumumab refractory disease (dara exposed). ns: not significant.
Figure 33:
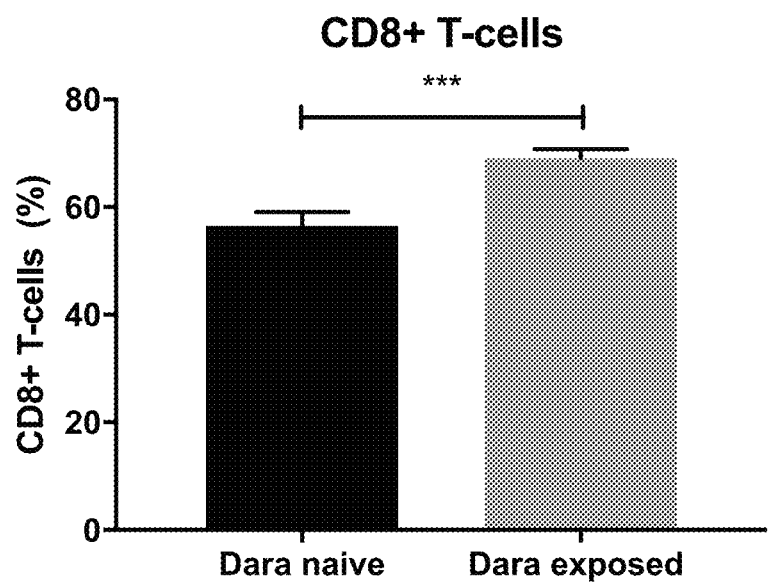
FIG. 33 shows the percentage of CD8$^+$ T cells in the sequential BM aspirates from RRMM patients before initiation of daratumumab (before dara) and at development of daratumumab refractory disease (dara exposed).

Since improvement in tumor reduction could be aided by the recently discovered immune stimulatory effects of DARA, sequential BM aspirates from MM patients were analyzed before and after DARA treatment (n=5). Here we observed comparable BCMA expression, yet improved MM cell lysis by JNJ-957 in samples obtained after disease progression during DARA compared to samples before DARA initiation (mean lysis at 4.0 µg/mL: 93 vs 74%; FIG. 30). In these BM aspirates, the percentage of Tregs (FIG. 31) and CD4$^+$ cells (FIG. 32) were slightly decreased whereas the percentage of CD8+ cells (FIG. 33) was increased in daratumumab naïve vs. daratumumab exposed patient samples. In this study, the samples were obtained from patients whose median duration of daratumumab monotherapy treatment of patients was 3 (1-7) months. In a follow-up study with samples from 8 RRMM patients, the percentage of CD38$^+$ Tregs and Bregs were significantly reduced in dara refractory vs. daratumumab naïve patient samples (data not shown).

Figure 34:
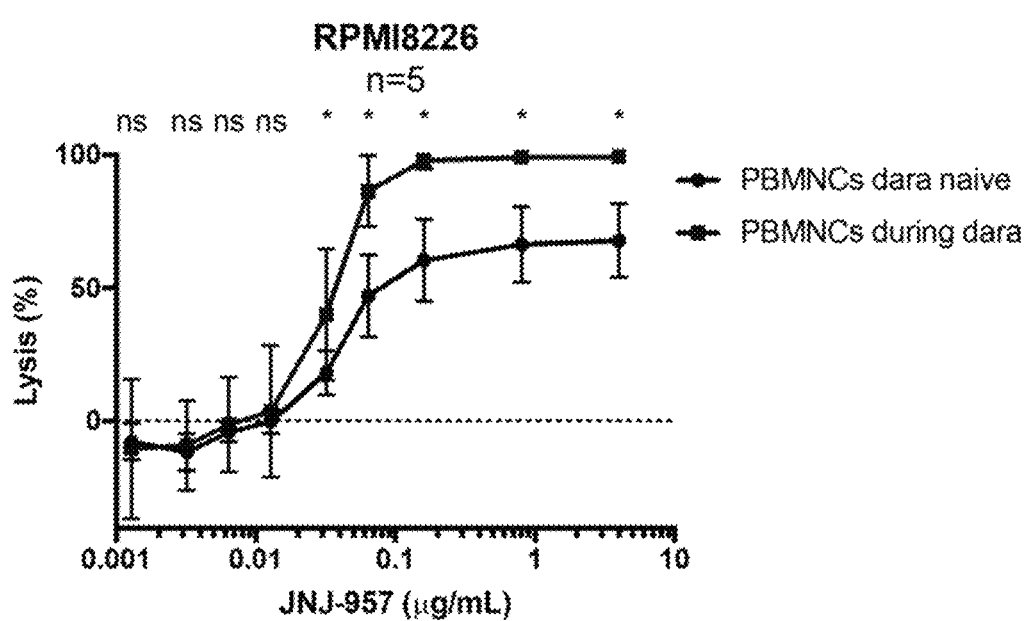
FIG. 34 shows that JNJ-957-mediated lysis of RPMI8226 multiple myeloma cells using patient derived PB MNCs as effector cells was augmented by PB MNCs from patients who had received daratumumab ("PBMNCs during dara") when compared to samples from the same patients before initiation of daratumumab treatment ("PBMNCs dara naïve") (n=5). Data was depicted as mean±SEM; P values were calculated using a paired t-test. ns: not significant; *P<0.05.
Figure 35:
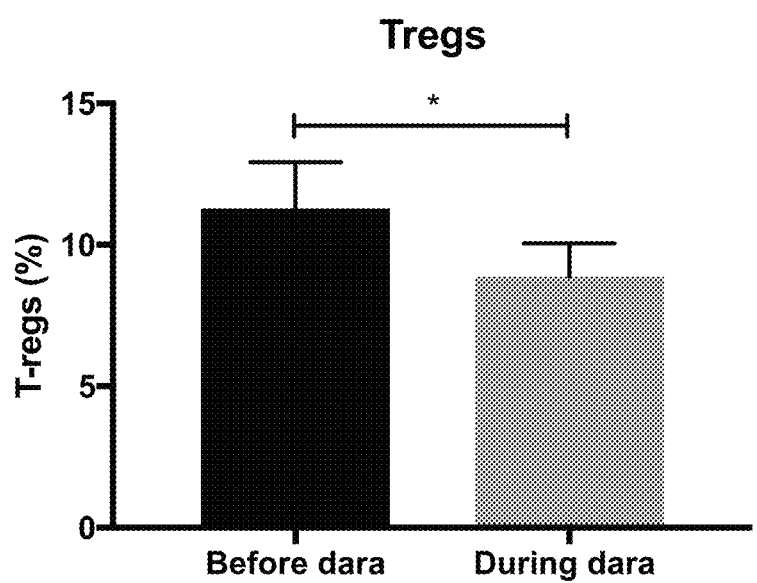
FIG. 35 shows the percentage of Tregs in PB-MNC samples from daratumumab naïve (before dara) and daratumumab refractory (during dara) RRMM patients.
Figure 36:
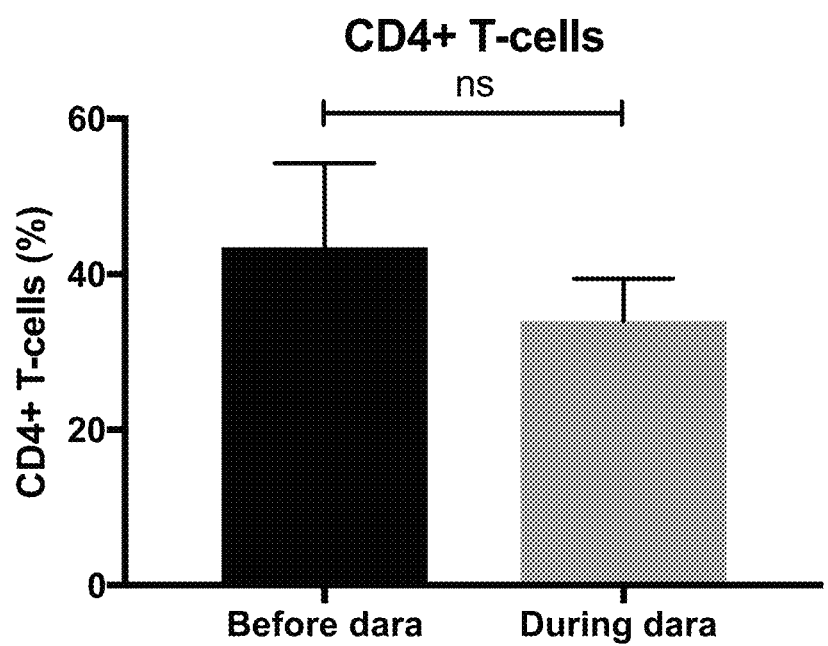
FIG. 36 shows the percentage of CD4$^+$ T cells in PB-MNC samples from daratumumab naïve (before dara) and daratumumab refractory (during dara) RRMM patients. ns: not significant.
Figure 37:
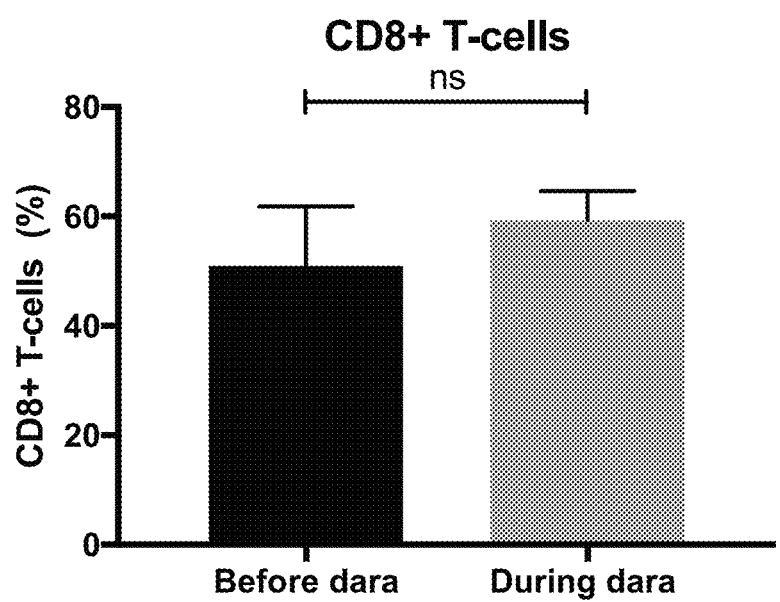
FIG. 37 shows the percentage of CD8$^+$ T cells in PB-MNC samples from daratumumab naïve (before dara) and daratumumab refractory (during dara) RRMM patients. ns: not significant.

JNJ-957-mediated lysis of RPMI 8226 multiple myeloma cell line was tested using sequential PB MNC samples from RRMM patients before and during daratumumab treatment as effector cells. Dara exposed PB MNCs were obtained during daratumumab treatment from patients with good response (either partial response, very good partial response or complete response) with median duration of daratumumab treatment 11 months (range 7-14 months). FIG. 34 shows that JNJ-957 mediated lysis of RPMI 8226 was enhanced using PB MNCs from dara exposed patients. In the PB-MNC samples, the percentage of Tregs (FIG. 35) and CD4+ cells (FIG. 36) were slightly decreased whereas the percentage of CD8+ cells (FIG. 37) was increased in daratumumab naïve vs. daratumumab exposed patient samples. In this study, the samples were obtained from patients whose median duration of daratumumab treatment of patients was 3 (1-7) months.

Figure 38:
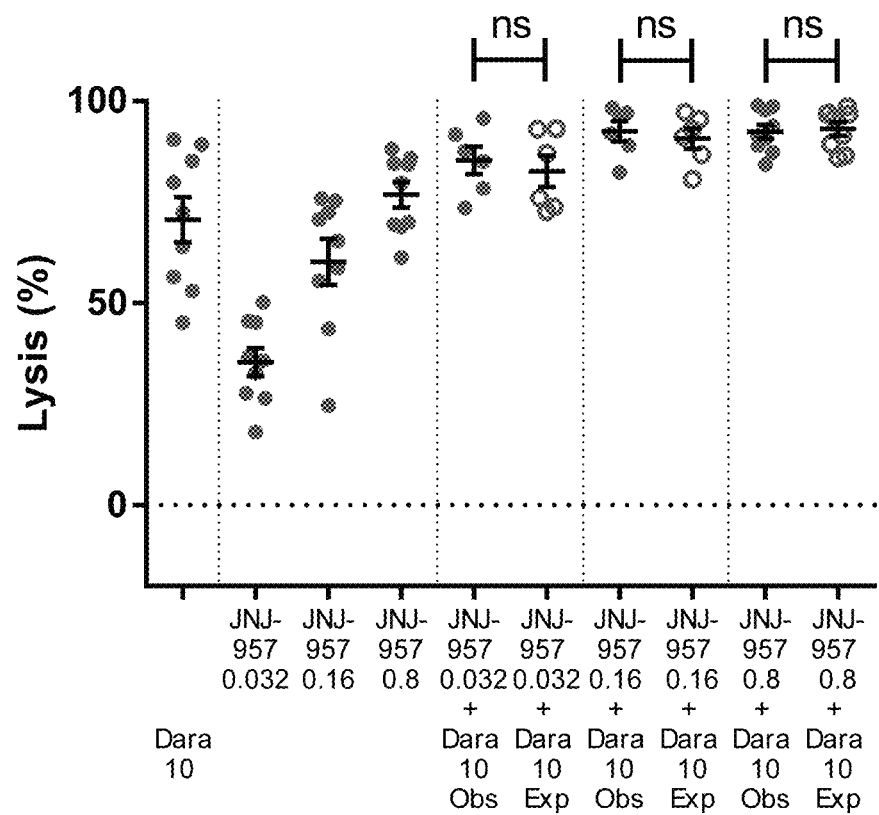
FIG. 38 shows that the addition of daratumumab augmented JNJ-957-mediated MM cell lysis. BM mononuclear cells (MNC) from NDMM (n=8) patients were treated with JNJ-957 (0.032-0.8 µg/mL) alone or in combination with 10 µg/mL daratumumab for 48 hours. The observed (Obs) lysis levels of MM cells by JNJ-957 and daratumumab were compared to the expected (Exp) lysis levels, which were calculated with the assumption that the combinatorial effect is achieved by additive effects as indicated in methods. Black bars depict the group mean value±SEM. P values were calculated using a paired student t-test. ns: not significant.
Figure 39:
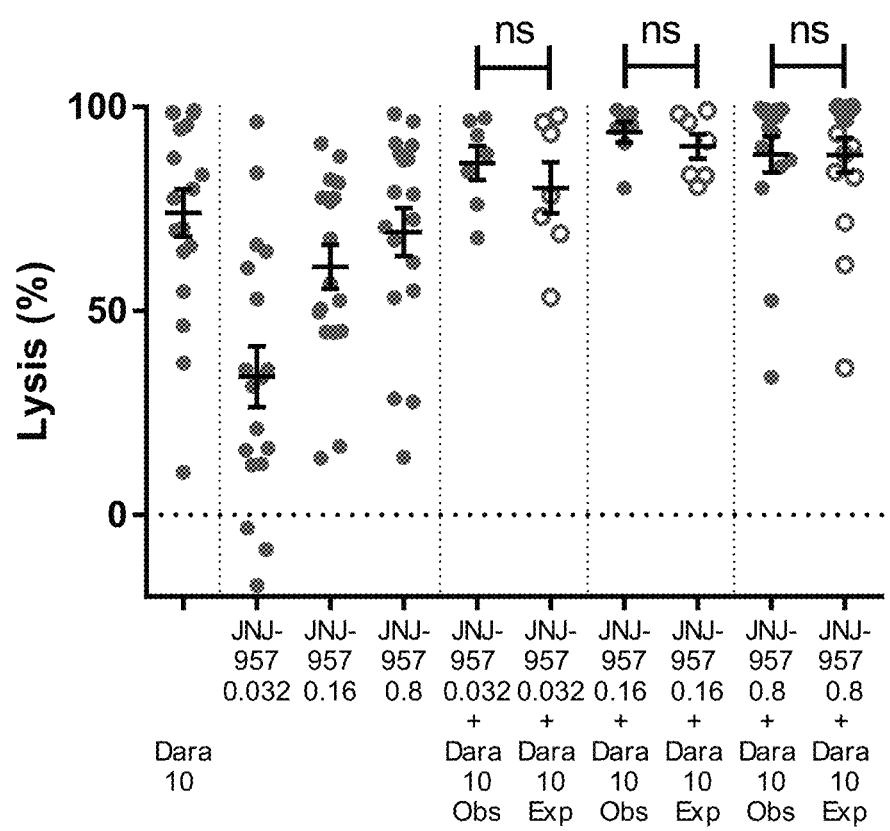
FIG. 39 shows that the addition of daratumumab augmented JNJ-957-mediated MM cell lysis. BM MNC of daratumumab naïve RRMM (n=17) patients were treated with JNJ-957 (0.032-0.8 µg/mL) alone or in combination with 10 µg/mL daratumumab for 48 hours. The observed (Obs) lysis levels of MM cells by JNJ-957 and daratumumab were compared to the expected (Exp) lysis levels, which were calculated with the assumption that the combinatorial effect is achieved by additive effects as indicated in methods. Black bars depict the group mean value±SEM. P values were calculated using a paired student t-test. ns: not significant.
Figure 40:
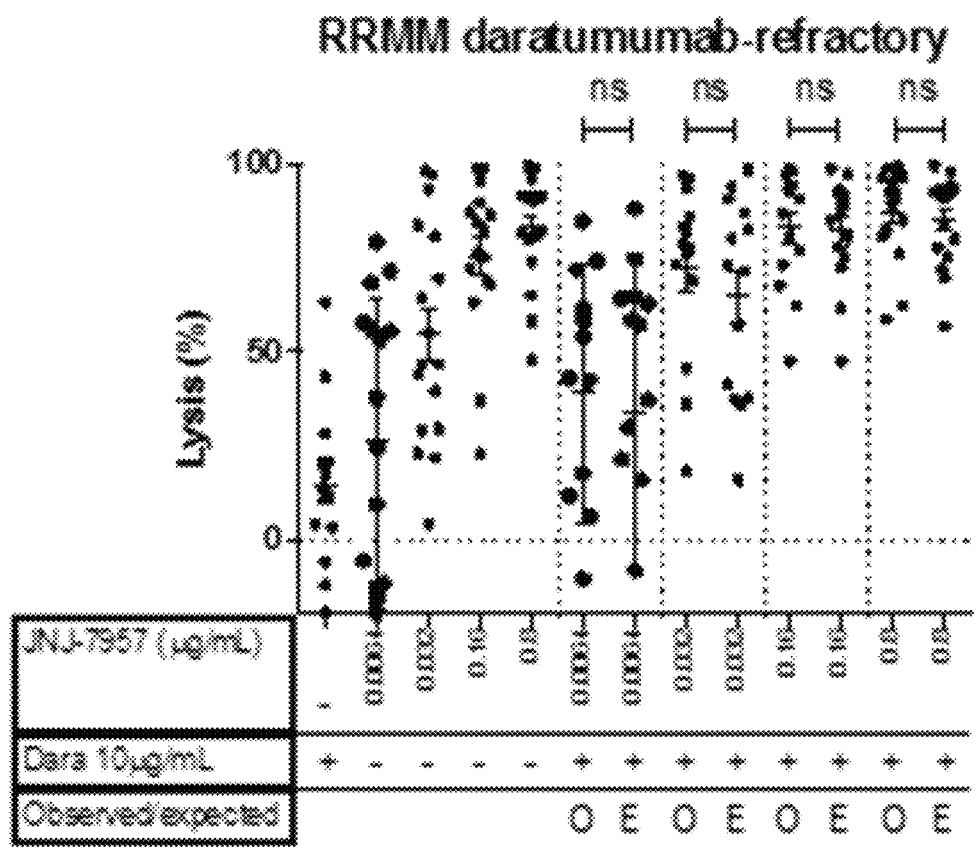
FIG. 40 shows that the addition of daratumumab augmented JNJ-957-mediated MM cell lysis. BM MNC of daratumumab refractory RRMM (n=14) patients were treated with JNJ-957 (0.032-0.8 µg/mL) alone or in combination with 10 µg/mL daratumumab for 48 hours. The observed (O) lysis levels of MM cells by JNJ-957 and daratumumab were compared to the expected (E) lysis levels, which were calculated with the assumption that the combinatorial effect is achieved by additive effects as indicated in methods. Black bars depict the group mean value±SEM. P values were calculated using a paired student t-test. JNJ-957 is referred to as JNJ-7957 in the Figure. Dara: daratumumab. ns: not significant.

Combination of JNJ-957 and daratumumab was also tested for the efficacy in killing MM cells obtained from NDMM or RRMM dara naïve patients. FIG. 38 shows the percentage lysis of BM MNC of newly diagnosed MM (NDMM) (n=8) patients treated with JNJ-957 (0.032-0.8 µg/mL) alone or in combination with daratumumab 10 µg/mL for 48 hours. The observed (obs) lysis levels of MM cells by JNJ-957 and daratumumab were compared to the expected (exp) lysis levels, which were calculated with the assumption that the combinatorial effect is achieved by additive effects as indicated in methods. Black bars depict the group mean value±SEM. P values are calculated using a paired student t-test. FIG. 39 shows the percentage lysis of BM MNCs inf RRNN dara naive patients. FIG. 40 shows the percentage lysis of BM MNCs in RRMM daratumumab refractory patients.

The study therefore demonstrated that JNJ-957 was effective in newly diagnosed and heavily pretreated MM patient samples. A high percentage or regulatory T cells negatively influenced JNJ-957 efficacy at low dosages however the negative effect was overcome by dose increase of JNJ-957. Daratumumab pretreatment in vivo enhanced the efficacy of JNJ-957 against MM cells.

The combination of JNJ-957 and daratumumab ex vivo showed additive efficacy; furthermore, in vivo pretreatment with daratumumab augmented the ex vivo efficacy of BCMAxCD3.

Example 3 Daratumumab Treatment Enhanced Ex Vivo Efficacy of Blinatumomab

Figure 41:
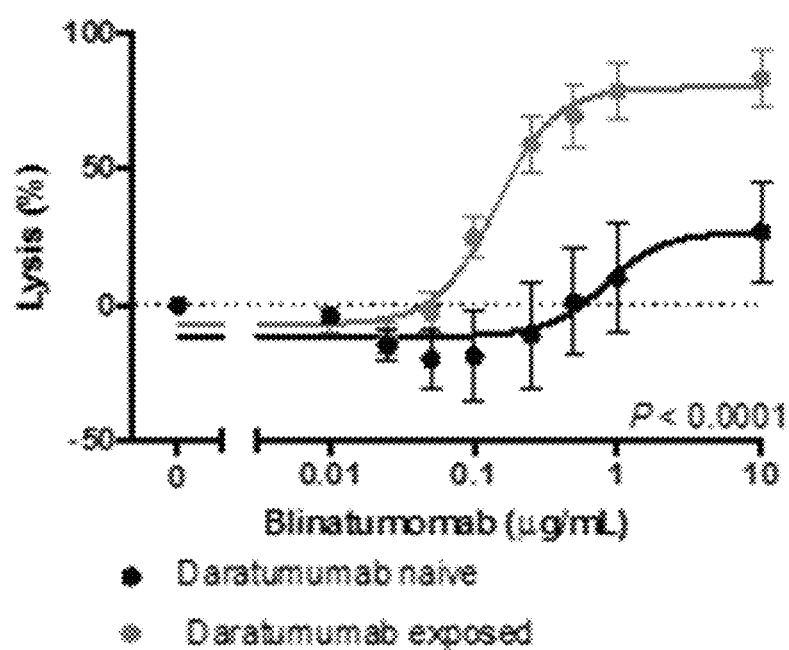
FIG. 41 shows blinatumomab-mediated lysis of the Raji cell line, using sequential PB samples from 11 RRMM patients as effector cells (E:T of 10:1), which were obtained directly before initiation of daratumumab treatment (black, bottom lin) and during daratumumab treatment (grey, top line); median duration of treatment 7 months, range 2-14 months. Blinatumomoab-based cytotoxicity assay was performed after a 48-hour incubation of Raji cells with blinatumomab (0.01-10 µg/mL) in the presence of these PB-MNCs. Data represents mean±SEM, experiments were performed in duplicate. The statistical significance (P-value) between the indicated groups was calculated using nonlinear regression analysis.

To assess if daratumumab treatment is also beneficial for other T-cell redirecting therapies, CD19$^+$ Raji cells were treated with blinatumomab, an FDA-approved CD19xCD3 BiTE for the treatment of acute lymphoblastic leukemia, using paired daratumumab-naïve and daratumumab exposed PB-MNCs from 11 MM patients Similar to the observations with JNJ-957, the activity of blinatumomab was significantly enhanced by co-incubation with daratumumab-exposed PB-MNCs, when compared to daratumumab-naïve PB-MNCs (P<0.0001; FIG. 41). Blinatumomab comprises the amino acid sequence of SEQ ID NO: 53.

```
SEQ ID NO: 53
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIKGGGGSGGGGSGGGGSQVQLQQSGAELVRPGSSVKISCKA

SGYAFSSYWMNWVKQRPGQGLEWIGQIWPGDGDTNYNGKFKGKATLTADE

SSSTAYMQLSSLASEDSAVYFCARRETTTVGRYYYAMDYWGQGTTVTVSS

GGGGSDIKLQQSGAELARPGASVKMSCKTSGYTFTRYTMHWVKQRPGQGL
```

-continued
EWIGYINPSRGYTNYNQKFKDKATLTTDKSSSTAYMQLSSLTSEDSAVYY

CARYYDDHYCLDYWGQGTTLTVSSVEGGSGGSGGSGGSGGVDDIQLTQSP

AIMSASPGEKVTMTCRASSSVSYMNWYQQKSGTSPKRWIYDTSKVASGVP

YRFSGSGSGTSYSLTISSMEAEDAATYYCQQWSSNPLTFGAGTKLELKHH

HHHH

Example 4 JNJ-957 Effectively Killed Primary pPCL Cells

Figure 42:
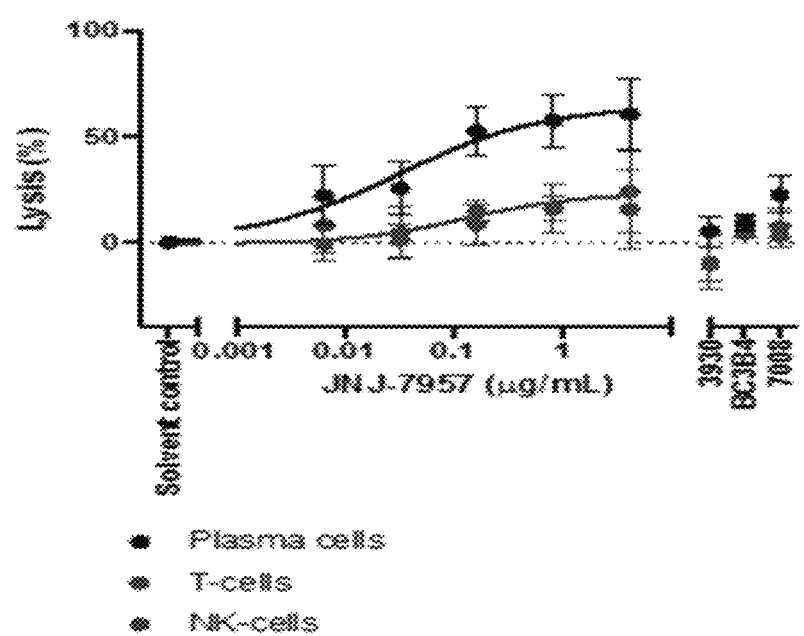
FIG. 42 shows a dose response of JNJ-957-mediated lysis of plasma, T cells and NK cells of BM-MNC cells obtained from six primary plasma cell leukemia (pPCL) patients. Percent lysis was measured at various antibody concentrations (0.0064-4.0 µg/mL) as indicated in the Figure. Top line: plasma cells; bottom line: overlapping line for T cells and NK cells. JNJ-957 is refereed to as JNJ-7957 in the Figure.

Ex vivo activity of JNJ-957 was evaluated in BM samples from 6 patients with newly diagnosed pPCL, which is characterized by an aggressive clinical behavior. JNJ-957 mediated tumor cell lysis in these pPCL samples was similar to lysis observed in NDMM and daratumumab-naïve RRMM samples, but lower than observed in daratumumab-refractory RRMM patient samples (P=0.0014) (FIG. 42). Although the median E:T ratio in pPCL samples was approximately 8-fold lower, the extent of activation of both $CD4^+$ (P=0.0040) and $CD8^+$ T-cells (P<0.0001), as well as the extent of degranulation of $CD8^+$ T-cells (P=0.0141) was superior in pPCL, when compared to NDMM. Degranulation of $CD4^+$ T-cells was similar to that observed in NDMM.

BM-MNCs were obtained from 6 pPCL patients and incubated with JNJ-957 (0.0064-4.0 µg/mL) or control antibodies 3930, BC3B4 and 7008 (4.0 µg/mL) for 48 hours, after which the surviving $CD138^+$ tumor cells, as well as T- and NK-cells, were enumerated using flow cytometry analysis. Data was expressed as mean % lysis of cells±SEM. All experiments were performed in duplicate.

Example 5 Combination of a GPRC5DxCD3 Bispecific Antibody with Daratumumab

Figure 43:
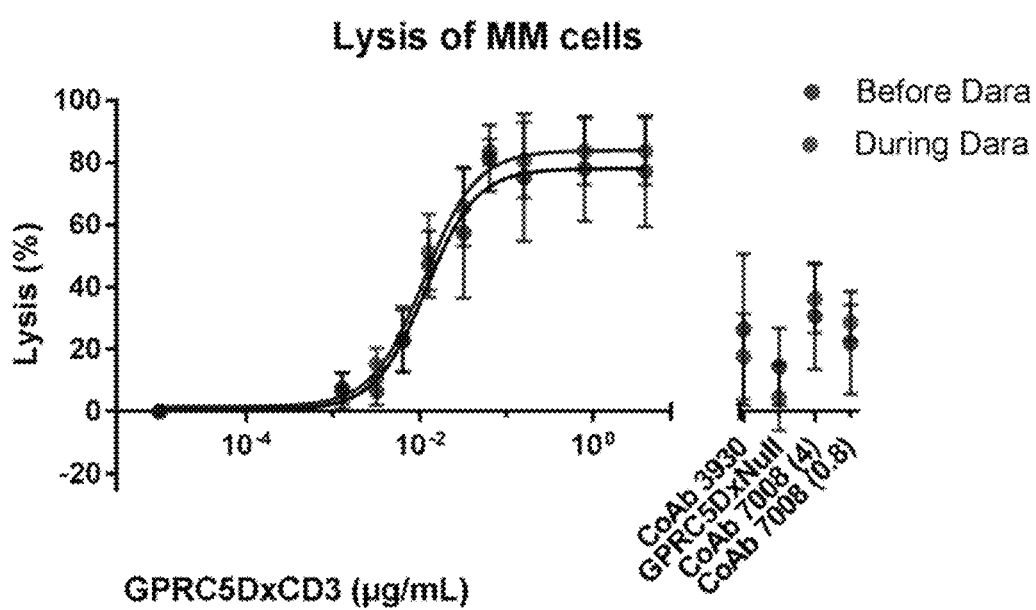
FIG. 43 shows anti-GPRC5DxCD3 antibody-mediated lysis of the MM cell line, using sequential PB samples from 11 RRMM patients as effector cells (E:T of 10:1), which were obtained directly before initiation of daratumumab treatment (bottom line) and during daratumumab treatment (top line); median duration of treatment 7 months, range 2-14 months. Blinatumomab-based cytotoxicity assay was performed after a 48-hour incubation of Raji cells with blinatumomab (0.01-10 µg/mL) in the presence of these PB-MNCs. Data represents mean±SEM, experiments were performed in duplicate.

To further assess if daratumumab treatment is also beneficial for other T-cell redirecting therapies, RPMI MM cells were treated with a GPRC5DxCD3 bispecific antibody using paired daratumumab-naïve and daratumumab exposed PB-MNCs from 11 MM patients (the samples were obtained from the same patients as described in above examples. As a control, antibodies in which either the CD3 or the GPRC5D binding VH/VL domains were replaced with null domains binding irrelevant antigens (gp120) were used (control mAb 3930 nullxnull, control mAb 7008: NullxCD3, control mAb GPRC5Dxnull). The antibodies were tested over a concentration of 0.00064-4.0 µg/ml. The GPRC5DxCD3 bispecific antibody mediated MM cell lysis in both daratumumab naïve and daratumumab refractory samples with similar potency (FIG. 43).

Figure 44:
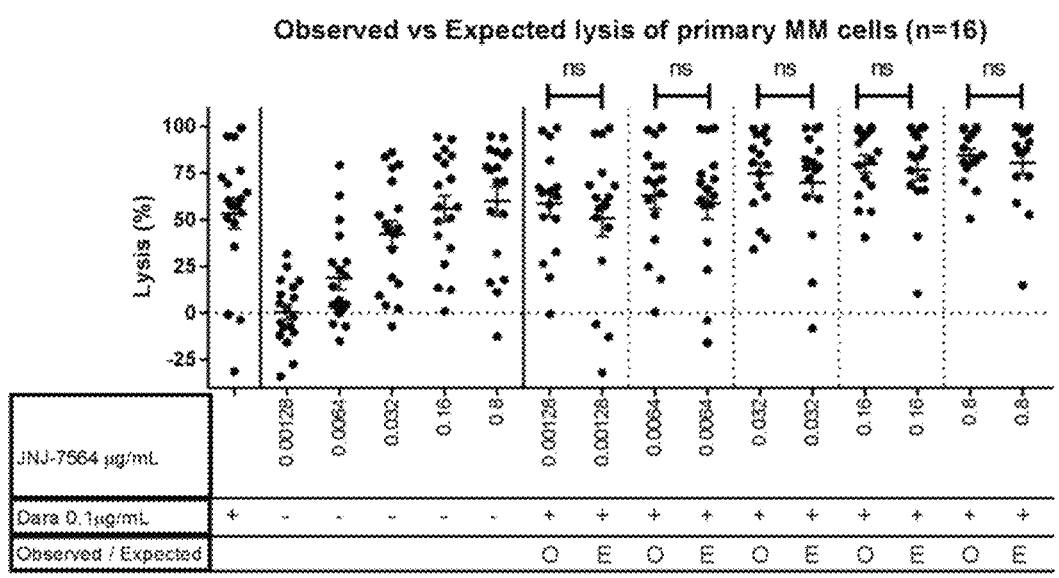
FIG. 44 shows that the addition of daratumumab was additive to the anti-GPRC5DxCD3 bispecific antibody (JNJ-7564)-mediated MM cell lysis. BM MNC of daratumumab naïve RRMM (n=17) patients were treated with the anti-GPRC5DxCD3 bispecific antibody (0.00128-0.8 µg/mL) alone or in combination with 0.1 µg/mL daratumumab for 48 hours. The observed (O lysis levels of MM cells by the anti-GPRC5DxCD3 bispecific antibody and daratumumab were compared to the expected (E) lysis levels, which were calculated with the assumption that the combinatorial effect is achieved by additive effects as indicated in methods. Black bars depict the group mean value±SEM. P values were calculated using a paired student t-test. ns: not significant. Dara: daratumumab.

Combination of the GPRC5DxCD3 bispecific antibody and daratumumab was also tested for the efficacy in killing MM cells obtained from NDMM or RRMM dara naïve patients. FIG. 44 shows the percentage lysis of BM MNC of primary MM cells mediated by the GPRC5DxCD3 bispecific antibody (0.0128-0.8 µg/mL) alone or in combination with daratumumab 0.1 µg/mL for 48 hours. The observed (O) lysis levels of MM cells by the GPRC5DxCD3 bispecific antibody and daratumumab were compared to the expected (E) lysis levels, which were calculated with the assumption that the combinatorial effect is achieved by additive effects as indicated in methods. Black bars depict the group mean value±SEM. P values were calculated using a paired student t-test. Co-incubation with daratumumab enhanced MM cell lysis by the GPRC5DxCD3 bispecific antibody in an additive fashion.

The GPRC5DxCD3 bispecific antibody comprises a GPRC5D binding arm GC5B596 and a CD3 binding arm CD3B219. The amino acid sequences of GC5B596 are shown in Table 8. The amino acid sequences of CD3B219 are show in Table 4.

The GPRC5DxCD3 bispecific antibody used in the experiments is described in WO20180037651A1 and comprises the following sequences:

a GPRC5D binding domain comprising the HCDR1, the HCDR2, the HCDR3, the LCDR1, the LCDR2 and the LCDR3 of SEQ ID NOs: 43, 44, 45, 446, 47 and 48, respectively, and a CD3 binding domain comprising the HCDR1, the HCDR2, the HCDR3, the LCDR1, the LCDR2 and the LCDR3 of SEQ ID NOs: 33, 34, 35, 36, 37 and 38, respectively;

the GPRC5D binding domain comprising the VH of SEQ ID NO: 49 and the VL of SEQ ID NO: 50 and the CD3 binding domain comprises the VH of SEQ ID NO: 39 and the VL of SEQ ID NO: 40; and a first heavy chain (HC1) of SEQ ID NO: 51, a first light chain (LC1) of SEQ ID NO: 52, a second heavy chain (HC2) of SEQ ID NO: 41 and a second light chain (LC2) of SEQ ID NO: 42.

The GPRC5DxCD3 bispecific antibody is an IgG4 isotype.

The HC1 comprises S228P, F234A and L235A substitutions.

The HC2 comprises S228P, F234A, L235A, F405L and R409K substitutions.

TABLE 8

| PS3B27 | Region | Sequence | SEQ ID NO: |
|---|---|---|---|
| GC5B596 | HCDR1 | GYTMN | 43 |
| | HCDR2 | LINPYNSDTNYAQKLQG | 44 |
| | HCDR3 | VALRVALDY | 45 |
| | LCDR1 | KASQNVATHVG | 46 |
| | LCDR2 | SASYRYS | 47 |
| | LCDR3 | QQYNRYPYT | 48 |
| | VH | QVQLVQSGAEVKKPGASVKVSCKASGYSFTGYT MNWVRQAPGQGLEWMGLINPYNSDTNYAQKL QGRVTMTTDTSTSTAYMELRSLRSDDTAVYYCA RVALRVALDYWGQGTLVTVSS | 49 |

TABLE 8-continued

| PS3B27 | Region | Sequence | SEQ ID NO: |
|---|---|---|---|
| | VL | DIQMTQSPSSLSASVGDRVTITCKASQNVATHVG WYQQKPGKAPKRLIYSASYRYSGVPSRFSGSGSG TEFTLTISNLQPEDFATYYCQQYNRYPYTFGQGT KLEIK | 50 |
| | HC | QVQLVQSGAEVKKPGASVKVSCKASGYSFTGYT MNWVRQAPGQGLEWMGLINPYNSDTNYAQKL QGRVTMTTDTSTSTAYMELRSDDTAVYYCA RVALRVALDYWGQGTLVTVSS ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKY GPPCPPCPAPEAAGGPSVFLFPPKPKDTLMISRTP EVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQEE MTKNQVSLTCLVKGFYPSDIAVEWESNGQPENN YKTTPPVLDSDGSFFLYSRLTVDKSRWQEGNVFS CSVMHEALHNHYTQKSLSLSLGK | 51 |
| | LC | DIQMTQSPSSLSASVGDRVTITCKASQNVATHVG WYQQKPGKAPKRLIYSASYRYSGVPSRFSGSGSG TEFTLTISNLQPEDFATYYCQQYNRYPYTFGQGT KLEIKKAAPSVTLFPPSSEELQANKATLVCLISDF YPGAVTVAWKGDSSPVKAGVETTTPSKQSNNKY AASSYLSLTPEQWKSHRSYSCQVTHEGSTVEKTV APTECS | 52 |

Example 6 Combinations of T-Cell Redirecting Therapies with Anti-CD38 Antibodies Effect of combining additional T-cell redirecting therapies with anti-CD38 antibodies is assessed similarly as described in Examples 1-5. The combinations are tested for their additive or synergistic effect to mediate killing of tumor cells that are targeted by the T-cell redirecting therapies (i.e., tumor cells that express the antigen that is bound by the T-cell redirecting therapy). The effect of pre-treatment of anti-CD38 antibodies on efficacy of T-cell redirecting therapies is assessed as described herein in the Examples.

The T-cell redirecting therapies that are tested in combination with anti-CD38 antibodies include PSMAxCD3, TMEFF2xCD3, CD123xCD3 and CD33xCD3 bispecific antibodies.

An exemplary PSMAxCD3 bispecific antibody is PS3B27, comprising a PSMA binding domain PSMB127 and the CD3 binding domain CD3B219. Table 9 shows the amino acid sequences of PS3B27. The amino acid sequences of CD3B219 are show in Table 4.

An exemplary PSMAxCD3 bispecific antibody that is used in the experiments comprises the following sequences:

a PSMA binding domain comprising the HCDR1, the HCDR2, the HCDR3, the LCDR1, the LCDR2 and the LCDR3 of SEQ ID NOs: 54, 55, 56, 9, 10 and 59, respectively, and a CD3 binding domain comprising the HCDR1, the HCDR2, the HCDR3, the LCDR1, the LCDR2 and the LCDR3 of SEQ ID NOs: 33, 34, 35, 36, 37 and 38, respectively;

the PSMA binding domain comprising the VH of SEQ ID NO: 60 and the VL of SEQ ID NO: 61 and the CD3 binding domain comprises the VH of SEQ ID NO: 39 and the VL of SEQ ID NO: 40; and a first heavy chain (HC1) of SEQ ID NO: 62, a first light chain (LC1) of SEQ ID NO: 63, a second heavy chain (HC2) of SEQ ID NO: 41 and a second light chain (LC2) of SEQ ID NO: 42.

The anti-PSMAxCD3 bispecific antibody is an IgG4 isotype.

The HC1 comprises S228P, F234A and L235A substitutions.

The HC2 comprises S228P, F234A, L235A, F405L and R409K substitutions.

TABLE 9

| | Region | Sequence | SEQ ID NO: |
|---|---|---|---|
| PSMB127 | HCDR1 | SDAMH | 54 |
| | HCDR2 | EISGSGGYTNYADSVKG | 55 |
| | HCDR3 | DSYDSSLYVGDYFDY | 56 |
| | LCDR1 | RASQSVSSYLA | 9 |
| | LCDR2 | DASNRAT | 10 |
| | LCDR3 | QQRSNWPLT | 59 |
| | VH | EVQLLESGGGLVQPGGSLRLSCAASGFTFKSDA MHWVRQAPGKGLEWVSEISGSGGYTNYADSVK | 60 |

TABLE 9-continued

| Region | Sequence | SEQ ID NO: |
|---|---|---|
|  | GRFTISRDNSKNTLYLQMNSLRAEDTAVYYCAR DSYDSSLYVGDYFDYWGQGTLVTVSS |  |
| VL | EIVLTQSPATLSLSPGERATLSCRASQSVSSYLAW YQQKPGQAPRLLIYDASNRATGIPARFSGSGSGT DFTLTISSLEPEDFAVYYCQQRSNWPLTFGQGTK VEIK | 61 |
| HC | EVQLLESGGGLVQPGGSLRLSCAASGFTFKSDA MHWVRQAPGKGLEWVSEISGSGGYTNYADSVK GRFTISRDNSKNTLYLQMNSLRAEDTAVYYCAR DSYDSSLYVGDYFDYWGQGTLVTVSSASTKGPS VFPLAPCSRSTSESTAALGCLVKDYFPEPVTVSW NSGALTSGVHTFPAVLQSSGLYSLSSVVTVPSSSL GTKTYTCNVDHKPSNTKVDKRVESKYGPPCPPC PAPEAAGGPSVFLFPPKPKDTLMISRTPEVTCVV VDVSQEDPEVQFNWYVDGVEVHNAKTKPREEQ FNSTYRVVSVLTVLHQDWLNGKEYKCKVSNKG LPSSIEKTISKAKGQPREPQVYTLPPSQEEMTKNQ VSLTCLVKGFYPSDIAVEWESNGQPENNYKTTPP VLDSDGSFFLYSRLTVDKSRWQEGNVFSCSVMH EALHNHYTQKSLSLSLGK | 62 |
| LC | EIVLTQSPATLSLSPGERATLSCRASQSVSSYLAW YQQKPGQAPRLLIYDASNRATGIPARFSGSGSGT DFTLTISSLEPEDFAVYYCQQRSNWPLTFGQGTK VEIKRTVAAPSVFIFPPSDEQLKSGTASVVCLLNN FYPREAKVQWKVDNALQSGNSQESVTEQDSKDS TYSLSSTLTLSKADYEKHKVYACEVTHQGLSSPV TKSFNRGEC | 63 |

An exemplary TMEFF2xCD3 bispecific antibody is TMCB150, comprising a TMEFF2 binding arm TMEB762 and the CD3 binding arm CD3B376. Table 10 shows the amino acid sequences of TMEB762. Table 11 shows the amino acid sequences of CD3B376.

An exemplary TMEFF2xCD3 bispecific antibody that is used in the experiments is TMCB150 and comprises the following sequences:

a TMEFF2 binding domain comprising the HCDR1, the HCDR2, the HCDR3, the LCDR1, the LCDR2 and the LCDR3 of SEQ ID NOs: 64, 65, 66, 67, 68 and 69, respectively, and a CD3 binding domain comprising the HCDR1, the HCDR2, the HCDR3, the LCDR1, the LCDR2 and the LCDR3 of SEQ ID NOs: 74, 75, 76, 77, 78 and 79, respectively;

the TMEFF2 binding domain comprising the VH of SEQ ID NO: 70 and the VL of SEQ ID NO: 71 and the CD3 binding domain comprises the VH of SEQ ID NO: 80 and the VL of SEQ ID NO: 81; and a first heavy chain (HC1) of SEQ ID NO: 72, a first light chain (LC1) of SEQ ID NO: 73, a second heavy chain (HC2) of SEQ ID NO: 82 and a second light chain (LC2) of SEQ ID NO: 83.

The anti-TMEFF2xCD3 bispecific antibody is an IgG4 isotype.

The HC1 comprises S228P, F234A and L235A substitutions.

The HC2 comprises S228P, F234A, L235A, F405L and R409K substitutions.

TABLE 10

| | Region | Sequence | SEQ ID NO: |
|---|---|---|---|
| TMEB762 | HCDR1 | SYSMS | 64 |
|  | HCDR2 | VISGSGGFTDYADSVKG | 65 |
|  | HCDR3 | MPLNSPHDY | 66 |
|  | LCDR1 | RASQGIRNDLG | 67 |
|  | LCDR2 | AASSLQS | 68 |
|  | LCDR3 | LQDYNYPLT | 69 |
|  | VH | EVQLLESGGGLVQPGGSLRLSCAASGFTFSSYSM SWVRQAPGKGLEWVSVISGSGGFTDYADSVKGR FTISRDNSKNTLYLQMNSLRAEDTAVYYCARMP LNSPHDYWGQGTLVTVSS | 70 |
|  | VL | DIQMTQSPSSLSASVGDRVTITCRASQGIRNDLG WYQQKPGKAPKLLIYAASSLQSGVPSRFSGSGSG TDFTLTISSLQPEDFATYYCLQDYNYPLTFGGGT KVEIK | 71 |

TABLE 10-continued

| Region | Sequence | SEQ ID NO: |
|---|---|---|
| HC | VQLLESGGGLVQPGGSLRLSCAASGFTFSSYSMS WVRQAPGKGLEWVSVISGSGGFTDYADSVKGRF TISRDNSKNTLYLQMNSLRAEDTAVYYCARMPL NSPHDYWGQGTLVTVSSASTKGPSVFPLAPCSRS TSESTAALGCLVKDYFPEPVTVSWNSGALTSGV HTFPAVLQSSGLYSLSSVVTVPSSSLGTKTYTCN VDHKPSNTKVDKRVESKYGPPCPPCPAPEAAGG PSVFLFPPKPKDTLMISRTPEVTCVVVDVSQEDPE VQFNWYVDGVEVHNAKTKPREEQFNSTYRVVS VLTVLHQDWLNGKEYKCKVSNKGLPSSIEKTISK AKGQPREPQVYTLPPSQEEMTKNQVSLTCLVKG FYPSDIAVEWESNGQPENNYKTTPPVLDSDGSFF LYSRLTVDKSRWQEGNVFSCSVMHEALHNHYT QKSLSLSLGK | 72 |
| LC | DIQMTQSPSSLSASVGDRVTITCRASQGIRNDLG WYQQKPGKAPKLLIYAASSLQSGVPSRFSGSGSG TDFTLTISSLQPEDFATYYCLQDYNYPLTFGGGT KVEIKRTVAAPSVFIFPPSDEQLKSGTASVVCLLN NFYPREAKVQWKVDNALQSGNSQESVTEQDSK DSTYSLSSTLTLSKADYEKHKVYACEVTHQGLSS PVTKSFNRGEC | 73 |

TABLE 11

| | Region | Sequence | SEQ ID NO: |
|---|---|---|---|
| CD3B396 | HCDR1 | NNNAAWS | 74 |
| | HCDR2 | RTYYRSKWLYDYAVSVKS | 75 |
| | HCDR3 | GYSSSFDY | 76 |
| | LCDR1 | TGTSSNIGTYKFVS | 77 |
| | LCDR2 | EVSKRPS | 78 |
| | LCDR3 | VSYAGSGTLL | 79 |
| | VH | QVQLQQSGPRLVRPSQTLSLTCAISGDSVFNNNA AWSWIRQSPSRGLEWLGRTYYRSKWLYDYAVS VKSRITVNPDTSRNQFTLQLNSVTPEDTALYYCA RGYSSSFDYWGQGTLVTVSS | 80 |
| | VL | QSALTQPASVSGSPGQSITISCTGTSSNIGTYKFVS WYQQHPDKAPKVLLYEVSKRPSGVSSRFSGSKS GNTASLTISGLQAEDQADYHCVSYAGSGTLLFG GGTKLTVL | 81 |
| | HC | QVQLQQSGPRLVRPSQTLSLTCAISGDSVFNNNA AWSWIRQSPSRGLEWLGRTYYRSKWLYDYAVS VKSRITVNPDTSRNQFTLQLNSVTPEDTALYYCA RGYSSSFDYWGQGTLVTVSSASTKGPSVFPLAPC SRSTSESTAALGCLVKDYFPEPVTVSWNSGALTS GVHTFPAVLQSSGLYSLSSVVTVPSSSLGTKTYT CNVDHKPSNTKVDKRVESKYGPPCPPCPAPEAA GGPSVFLFPPKPKDTLMISRTPEVTCVVVDVSQE DPEVQFNWYVDGVEVHNAKTKPREEQFNSTYR VVSVLTVLHQDWLNGKEYKCKVSNKGLPSSIEK TISKAKGQPREPQVYTLPPSQEEMTKNQVSLTCL VKGFYPSDIAVEWESNGQPENNYKTTPPVLDSD GSFLLYSKLTVDKSRWQEGNVFSCSVMHEALHN HYTQKSLSLSLGK | 82 |
| | LC | QSALTQPASVSGSPGQSITISCTGTSSNIGTYKFVS WYQQHPDKAPKVLLYEVSKRPSGVSSRFSGSKS GNTASLTISGLQAEDQADYHCVSYAGSGTLLFG GGTKLTVLGQPKAAPSVTLFPPSSEELQANKATL VCLISDFYPGAVTVAWKADSSPVKAGVETTTPSK QSNNKYAASSYLSLTPEQWKSHRSYSCQVTHEG STVEKTVAPTECS | 83 |

An exemplary CD33xCD3 bispecific antibody is C3CB189, comprising a CD33 binding arm C33B904 and the CD3 binding arm CD3B376. Table 12 shows the amino acid sequences of C33B904. The amino acid sequences of CD3B376 are shown in Table 11.

The HC1 comprises S228P, F234A and L235A substitutions.

The HC2 comprises S228P, F234A, L235A, F405L and R409K substitutions.

TABLE 12

| | Region | Sequence | SEQ ID NO: |
|---|---|---|---|
| C33B904 | HCDR1 | DYAMH | 84 |
| | HCDR2 | GIGWSGGSIVYADSVKG | 85 |
| | HCDR3 | DSPYGDFFDY | 86 |
| | LCDR1 | KSSQTVFYSSNNKNYLA | 87 |
| | LCDR2 | WASTRKS | 88 |
| | LCDR3 | QHYYSTPYT | 89 |
| | VH | EVQLVESGGGLVQPGRSLRLSCAASGFTFDDYA MHWVRQAPGKGLEWVSGIGWSGGSIVYADSVK GRFTISRDNAKNSLYLQMNSLRAEDTALYYCAK DSPYGDFFDYWGQGTLVTVSS | 90 |
| | VL | DIVMTQSPDSLAVSLGERATINCKSSQTVFYSSN NKNYLAWYQQKPGQPPKLLISWASTRKSGVPD RFSGSGSGTDFTLTVSSLQAEDVAVYYCQHYY STPYTFGQGTKLEIK | 91 |
| | HC | EVQLVESGGGLVQPGRSLRLSCAASGFTFDDYA MHWVRQAPGKGLEWVSGIGWSGGSIVYADSVK GRFTISRDNAKNSLYLQMNSLRAEDTALYYCAK DSPYGDFFDYWGQGTLVTVSSASTKGPSVFPLAP CSRSTSESTAALGCLVKDYFPEPVTVSWNSGALT SGVHTFPAVLQSSGLYSLSSVVTVPSSSLGTKTYT CNVDHKPSNTKVDKRVESKYGPPCPPCPAPEAA GGPSVFLFPPKPKDTLMISRTPEVTCVVVDVSQE DPEVQFNWYVDGVEVHNAKTKPREEQFNSTYR VVSVLTVLHQDWLNGKEYKCKVSNKGLPSSIEK TISKAKGQPREPQVYTLPPSQEEMTKNQVSLTCL VKGFYPSDIAVEWESNGQPENNYKTTPPVLDSD GSFFLYSRLTVDKSRWQEGNVFSCSVMHEALHN HYTQKSLSLSLGK | 92 |
| | LC | DIVMTQSPDSLAVSLGERATINCKSSQTVFYSSN NKNYLAWYQQKPGQPPKLLISWASTRKSGVPDR FSGSGSGTDFTLTVSSLQAEDVAVYYCQHYYSTP YTFGQGTKLEIKKAAPSVTLFPPSSEELQANKATL VCLISDFYPGAVTVAWKGDSSPVKAGVETTTPSK QSNNKYAASSYLSLTPEQWKSHRSYSCQVTHEG STVEKTVAPTECS | 93 |

An exemplary CD33xCD3 bispecific antibody that is used in the experiments is C3CB189 and comprises the following sequences:

a CD33 binding domain comprising the HCDR1, the HCDR2, the HCDR3, the LCDR1, the LCDR2 and the LCDR3 of SEQ ID NOs: 84, 85, 86, 87, 88 and 89, respectively, and a CD3 binding domain comprising the HCDR1, the HCDR2, the HCDR3, the LCDR1, the LCDR2 and the LCDR3 of SEQ ID NOs: 74, 75, 76, 77, 78 and 79, respectively;

the CD33 binding domain comprising the VH of SEQ ID NO: 90 and the VL of SEQ ID NO: 91 and the CD3 binding domain comprises the VH of SEQ ID NO: 80 and the VL of SEQ ID NO: 81; and a first heavy chain (HC1) of SEQ ID NO: 92, a first light chain (LC1) of SEQ ID NO: 93, a second heavy chain (HC2) of SEQ ID NO: 82 and a second light chain (LC2) of SEQ ID NO: 83.

The anti-CD33xCD3 bispecific antibody is an IgG4 isotype.

An exemplary CD123xCD3 bispecific antibody is 8747, comprising a CD123 binding arm I3RB218 and the CD3 binding arm CD3B219. 8747 is described in WO2016036937A1. Table 13 shows the amino acid sequences of I3RB218. The amino acid sequences of CD3B219 are shown in Table 4.

An exemplary CD123xCD3 bispecific antibody that is used in the experiments is 8747 and comprises the following sequences:

a CD123 binding domain comprising the HCDR1, the HCDR2, the HCDR3, the LCDR1, the LCDR2 and the LCDR3 of SEQ ID NOs: 94, 95, 96, 9, 10 and 59, respectively, and a CD3 binding domain comprising the HCDR1, the HCDR2, the HCDR3, the LCDR1, the LCDR2 and the LCDR3 of SEQ ID NOs: 33, 34, 35, 36, 37 and 38, respectively;

the CD123 binding domain comprising the VH of SEQ ID NO: 100 and the VL of SEQ ID NO: 61 and the CD3 binding domain comprises the VH of SEQ ID NO: 39 and the VL of SEQ ID NO: 40; and a first heavy chain (HC1) of SEQ ID NO: 102, a first light chain (LC1) of SEQ ID NO: 63, a second heavy chain (HC2) of SEQ ID NO: 41 and a second light chain (LC2) of SEQ ID NO: 42.

The anti-CD123xCD3 bispecific antibody is an IgG4 isotype.

The HC1 comprises S228P, F234A and L235A substitutions.

The HC2 comprises S228P, F234A, L235A, F405L and R409K substitutions.

TABLE 13

| | Region | Sequence | SEQ ID NO: |
|---|---|---|---|
| I3RB218 | HCDR1 | GYWMH | 94 |
| | HCDR2 | AIRSDGSSKYYADSVKG | 95 |
| | HCDR3 | DGVIEDTFDY | 96 |
| | LCDR1 | RASQSVSSYLA | 9 |
| | LCDR2 | DASNRAT | 10 |
| | LCDR3 | QQRSNWPLT | 59 |
| | VH | EVQLLESGGGLVQPGGSLRLSCAASGFTFSGYW MHWVRQAPGKGLEWVSAIRSDGSSKYYADSVK GRFTISRDNSKNTLYLQMNSLRAEDTAVYYCAK DGVIEDTFDYWGQGTLVTVSS | 100 |
| | VL | EIVLTQSPATLSLSPGERATLSCRASQSVSSYLAW YQQKPGQAPRLLIYDASNRATGIPARFSGSGSGT DFTLTISSLEPEDFAVYYCQQRSNWPLTFGQGTK VEIK | 61 |
| | HC | EVQLLESGGGLVQPGGSLRLSCAASGFTFSGYW MHWVRQAPGKGLEWVSAIRSDGSSKYYADSVK GRFTISRDNSKNTLYLQMNSLRAEDTAVYYCAK DGVIEDTFDYWGQGTLVTVSSASTKGPSVFPLAP CSRSTSESTAALGCLVKDYFPEPVTVSWNSGALT SGVHTFPAVLQSSGLYSLSSVVTVPSSSLGTKTYT CNVDHKPSNTKVDKRVESKYGPPCPPCPAPEAA GGPSVFLFPPKPKDTLMISRTPEVTCVVVDVSQE DPEVQFNWYVDGVEVHNAKTKPREEQFNSTYR VVSVLTVLHQDWLNGKEYKCKVSNKGLPSSIEK TISKAKGQPREPQVYTLPPSQEEMTKNQVSLTCL VKGFYPSDIAVEWESNGQPENNYKTTPPVLDSD GSFFLYSRLTVDKSRWQEGNVFSCSVMHEALHN HYTQKSLSLSLGK | 102 |
| | LC | EIVLTQSPATLSLSPGERATLSCRASQSVSSYLAW YQQKPGQAPRLLIYDASNRATGIPARFSGSGSGT DFTLTISSLEPEDFAVYYCQQRSNWPLTFGQGTK VEIKRTVAAPSVFIFPPSDEQLKSGTASVVCLLNN FYPREAKVQWKVDNALQSGNSQESVTEQDSKDS TYSLSSTLTLSKADYEKHKVYACEVTHQGLSSPV TKSFNRGEC | 63 |

To assess effect of pre-treatment with anti-CD38 antibodies on efficacy of tumor killing by the T cell redirecting therapeutics, tumor cells are isolated from subjects having tumors expressing the antigen the T-cell redirecting therapeutic binds, such as CD123, CD33, PSMA, TMEFF2 and the like, or established tumor cell lines are used. Tumor cell killing is assessed ex vivo by co-incubating tumor cells with PB-MNCs obtained from the anti-CD38 antibody exposed or anti-CD38 antibody naïve subjects as described in the Examples, and percentage of lysis of tumor cells is assessed in each group In a separate example, T-cell redirecting therapeutic and the anti-CD38 antibody are incubated together or individually with target and effector cells and the tumor cell killing mediated by the combination vs. individual therapeutics is assessed.

The effect of the anti-CD38 antibody on CD123xCD3 bispecific antibody-mediated tumor cell killing is assessed using CD123 positive tumor cells such as AML tumors, or cell lines such as AML cell lines KG1a, HL60 or MOLM13 as target cells.

The effect of the anti-CD38 antibody on CD33xCD3 bispecific antibody-mediated tumor cell killing is assessed using CD33 positive tumor cells such as AML tumors, or cell lines such as AML cell lines KG1a, HL60 or MOLM13 as target cells.

The effect of the anti-CD38 antibody on TMEFF2xCD3 bispecific antibody-mediated tumor cell killing is assessed using TMEFF2 positive tumor cells such as LnCP cells as target cells.

The effect of the anti-CD38 antibody on PSMAxCD3 bispecific antibody-mediated tumor cell killing is assessed using TMEFF2 positive tumor cells such as LnCP cells as target cells.

PBMCs or BM-MNCs isolated from subjects who have received the anti-CD38 antibody or who are naïve to anti-CD38 antibody treatment are used as effector cells.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A method of treating a multiple myeloma in a subject, comprising administering a therapeutically effective amount of an anti-CD38 antibody and a T cell redirecting therapeutic to the subject to treat the multiple myeloma,
wherein the anti-CD38 antibody comprises:
(a) a heavy chain complementarity determining region 1 (HCDR1) of SEQ ID NO: 6, an HCDR2 of SEQ ID NO: 7, an HCDR3 of SEQ ID NO: 8, a light chain complementarity determining region 1 (LCDR1) of SEQ ID NO: 9, an LCDR2 of SEQ ID NO: 10 and an LCDR3 of SEQ ID NO: 11, or
(b) a heavy chain variable region (VH) of SEQ ID NO: 4 and a light chain variable region (VL) of SEQ ID NO: 5, and
wherein the T cell redirecting therapeutic comprises:
(c) a CD3 binding domain comprising:
(i) a HCDR1 of SEQ ID NO: 33, an HCDR2 of SEQ ID NO: 34, an HCDR3 of SEQ ID NO: 35, an LCDR1 of SEQ ID NO: 36, an LCDR2 of SEQ ID NO: 37 and an LCDR3 of SEQ ID NO: 38; or
(ii) a VH of SEQ ID NO: 39 and a VL of SEQ ID NO: 40; and
(d) a BCMA binding domain comprising:
(i) a HCDR1 of SEQ ID NO: 23, a HCDR2 of SEQ ID NO: 24, a HCDR3 of SEQ ID NO: 25, a LCDR1 of SEQ ID NO: 26, a LCDR2 of SEQ ID NO: 27 and a LCDR3 of SEQ ID NO: 28; or
(ii) VH of SEQ ID NO: 29 and the VL of SEQ ID NO: 30.

2. The method of claim 1, wherein the anti-CD38 antibody is administered prior to administering the T cell redirecting therapeutic.

3. The method of claim 1, wherein the T cell redirecting therapeutic comprises a first heavy chain (HC1) of SEQ ID NO: 31, a first light chain (LC1) of SEQ ID NO: 32, a second heavy chain (HC2) of SEQ ID NO: 41, and a second light chain (LC2) of SEQ ID NO: 42.

4. The method of claim 1, wherein the T cell redirecting therapeutic is a multispecific antibody, a chimeric antigen receptor (CAR), or a T cell comprising the CAR.

5. The method of claim 4, wherein the multispecific antibody is an IgG1, an IgG2, an IgG3 or an IgG4 isotype.

6. The method of claim 5, wherein the multispecific antibody comprises one or more Fc substitutions that reduces binding of the multispecific antibody to a Fcγ receptor (FcγR).

7. The method of claim 6, wherein the one or more Fc substitutions is selected from the group consisting of F234A/L235A on IgG4, L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4 and S228P/F234A/L235A/G236-deleted/G237A/P238S on IgG4, wherein residue numbering is according to the EU index.

8. The method of claim 7, wherein the multispecific antibody further comprises a S228P substitution.

9. The method of claim 5, wherein the multispecific antibody comprises one or more asymmetric substitutions in a first CH3 domain or in a second CH3 domain, or in both the first CH3 domain and the second CH3 domain.

10. The method of claim 9, wherein the one or more asymmetric substitutions is selected from the group consisting of F450L/K409R, wild-type/F409L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

11. The method of claim 1, wherein the multiple myeloma is a newly diagnosed multiple myeloma.

12. The method of claim 1, wherein the multiple myeloma is a relapsed or a refractory multiple myeloma.

13. The method of claim 1, wherein the multiple myeloma is a high-risk multiple myeloma.

14. The method of claim 13, wherein the subject having the high-risk multiple myeloma has one or more chromosomal abnormalities comprising:
(a) t(4;14)(p16;q32);
(b) t(14;16)(q32;q23);
(c) del17p;
(d) 1qAmp;
(e) t(4;14)(p16;q32) and t(14;16)(q32;q23);
(f) t(4;14)(p16;q32) and del17p;
(g) t(14;16)(q32;q23) and del17p; or
(h) t(4;14)(p16;q32), t(14;16)(q32;q23) and del17p, or any combination thereof.

15. The method of claim 12, wherein the multiple myeloma is relapsed or refractory to treatment with the anti-CD38 antibody, lenalinomide, bortezomib, pomalidomide, carfilzomib, elotozumab, ixazomib, melphalan or thalidomide, or any combination thereof.

16. The method of claim 1, wherein the anti-CD38 antibody is an IgG1 isotype.

17. The method of claim 16, wherein the anti-CD38 antibody comprises a HC of SEQ ID NO: 12 and a LC of SEQ ID NO: 13.

18. The method of claim 1, further comprising administering to the subject one or more anti-cancer therapies.

19. The method of claim 18, wherein the one or more anti-cancer therapies is selected from the group consisting of an autologous stem cell transplant (ASCT), radiation, surgery, a chemotherapeutic agent, an immunomodulatory agent and a targeted cancer therapy.

20. The method of claim 19, wherein the one or more anti-cancer therapies is selected from the group consisting of lenalidomide, thalidomide, pomalidomide, bortezomib, carfilzomib, elotozumab, ixazomib, melphalan, dexamethasone, vincristine, cyclophosphamide, hydroxydaunorubicin, prednisone, rituximab, imatinib, dasatinib, nilotinib, bosutinib, ponatinib, bafetinib, saracatinib, tozasertib or danusertib, cytarabine, daunorubicin, idarubicin, mitoxantrone, hydroxyurea, decitabine, cladribine, fludarabine, topotecan, etoposide 6-thioguanine, corticosteroid, methotrexate, 6-mercaptopurine, azacitidine, arsenic trioxide and all-trans retinoic acid, or any combination thereof.

21. The method of claim 1, wherein the anti-CD38 antibody is administered at a dose of between about 8 mg/kg and about 16 mg/kg.

22. The method of claim 21, wherein the anti-CD38 antibody is administered or provided for administration in a pharmaceutical composition comprising between about 20 mg/mL to about 120 mg/mL of the anti-CD38 antibody in about 25 mM acetic acid, about 60 mM sodium chloride, about 140 mM mannitol and about 0.04% w/v polysorbate-20 (PS-20); at pH about 5.5.

23. The method of claim 3, wherein the T cell redirecting therapeutic is an IgG4 isotype and comprises phenylalanine at position 405 and arginine at position 409 in the HC1 and leucine at position 405 and lysine at position 409 in the HC2, wherein residue numbering is according to the EU Index.

24. The method of claim 23, wherein the T cell redirecting therapeutic further comprises proline at position 228, alanine at position 234 and alanine at position 235 in both the HC1 and the HC2.

25. The method of claim 1, wherein the multiple myeloma is a BCMA expressing multiple myeloma.

26. The method of claim 21, wherein the T cell redirecting therapeutic and the anti-CD38 antibody are administered by an intravenous injection.

27. The method of claim 21, wherein the T cell redirecting therapeutic is administered by an intravenous injection and the anti-CD38 antibody is administered by a subcutaneous injection.

28. The method of claim 1, wherein the subject is a human.

\* \* \* \* \*

SEQUENCE LISTING

```
<160> NUMBER OF SEQ ID NOS: 105

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                      60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 184
<212> TYPE: PRT
<213> ORGANISM: Homo sapiens
```

<400> SEQUENCE: 2

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 3
<211> LENGTH: 207
<212> TYPE: PRT
<213> ORGANISM: Homo sapiens

<400> SEQUENCE: 3

```
Met Gln Ser Gly Thr His Trp Arg Val Leu Gly Leu Cys Leu Leu Ser
1               5                   10                  15

Val Gly Val Trp Gly Gln Asp Gly Asn Glu Met Gly Gly Ile Thr
            20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
        50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175
```

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Ile
            195                 200                 205

<210> SEQ ID NO 4
<211> LENGTH: 122
<212> TYPE: PRT
<213> ORGANISM: Artificial Sequence
<220> FEATURE:
<223> OTHER INFORMATION: antibody VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: antibody VL

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: antibody HCDR1

```
<400> SEQUENCE: 6

Ser Phe Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: antibody HCDR2

<400> SEQUENCE: 7

Ala Ile Ser Gly Ser Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: antibody HCDR3

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: antibody LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: antibody LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: antibody LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
```

<223> OTHER INFORMATION: antibody heavy chain

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: antibody light chain

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 120
<212> TYPE: PRT
<213> ORGANISM: Artificial Sequence
<220> FEATURE:
<223> OTHER INFORMATION: mAb 003 VH

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Phe Ser Trp Val Arg Gln Ala Pro Gly Gln Gly Leu Glu Trp Met
            35                  40                  45

Gly Arg Val Ile Pro Phe Leu Gly Ile Ala Asn Ser Ala Gln Lys Phe
        50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
                100                 105                 110

Gly Thr Leu Val Thr Val Ser Ser
            115                 120

<210> SEQ ID NO 15
<211> LENGTH: 107
<212> TYPE: PRT
<213> ORGANISM: Artificial Sequence
<220> FEATURE:
<223> OTHER INFORMATION: mAb 003 VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: mAb 024 VH

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp

```
              100                 105                 110
Gly Arg Gly Thr Leu Val Thr Val Ser Ser
            115                 120

<210> SEQ ID NO 17
<211> LENGTH: 107
<212> TYPE: PRT
<213> ORGANISM: Artificial Sequence
<220> FEATURE:
<223> OTHER INFORMATION: mAb 024 VL

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Gly Leu Leu Ile
        35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: MOR-202 VH

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
            115                 120

<210> SEQ ID NO 19
<211> LENGTH: 109
<212> TYPE: PRT
<213> ORGANISM: Artificial Sequence
<220> FEATURE:
<223> OTHER INFORMATION: MOR-202 VL

<400> SEQUENCE: 19
```

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
            85                  90                  95

Val Phe Gly Gly Gly Thr Lys Leu Thr Val Leu Gly Gln
            100                 105

<210> SEQ ID NO 20
<211> LENGTH: 120
<212> TYPE: PRT
<213> ORGANISM: Artificial Sequence
<220> FEATURE:
<223> OTHER INFORMATION: Isatuximab VH

<400> SEQUENCE: 20

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
            85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 21
<211> LENGTH: 107
<212> TYPE: PRT
<213> ORGANISM: Artificial Sequence
<220> FEATURE:
<223> OTHER INFORMATION: Isatuximab VL

<400> SEQUENCE: 21

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
50                  55                  60

Ser Gly Ala Gly Thr Asp Phe Thr Phe Thr Ile Ser Ser Val Gln Ala
```

```
                65                  70                  75                  80
Glu Asp Leu Ala Val Tyr Tyr Cys Gln Gln His Tyr Ser Pro Pro Tyr
                    85                  90                  95

Thr Phe Gly Gly Gly Thr Lys Leu Glu Ile Lys
                100                 105

<210> SEQ ID NO 22
<211> LENGTH: 104
<212> TYPE: PRT
<213> ORGANISM: Homo sapiens

<400> SEQUENCE: 22

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
            35                  40                  45

Asp Asp Lys Asn Ile Gly Ser Asp Glu Asp His Leu Ser Leu Lys Glu
        50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
                100

<210> SEQ ID NO 23
<211> LENGTH: 7
<212> TYPE: PRT
<213> ORGANISM: Artificial Sequence
<220> FEATURE:
<223> OTHER INFORMATION: BCMB69 HCDR1

<400> SEQUENCE: 23

Ser Gly Ser Tyr Phe Trp Gly
1               5

<210> SEQ ID NO 24
<211> LENGTH: 16
<212> TYPE: PRT
<213> ORGANISM: Artificial Sequence
<220> FEATURE:
<223> OTHER INFORMATION: BCMB69 HCDR2

<400> SEQUENCE: 24

Ser Ile Tyr Tyr Ser Gly Ile Thr Tyr Tyr Asn Pro Ser Leu Lys Ser
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: BCMB69 HCDR3

<400> SEQUENCE: 25

His Asp Gly Ala Val Ala Gly Leu Phe Asp Tyr
1               5                   10

<210> SEQ ID NO 26
<211> LENGTH: 11
```

```
<212> TYPE: PRT
<213> ORGANISM: Artificial Sequence
<220> FEATURE:
<223> OTHER INFORMATION: BCMB69 LCDR1

<400> SEQUENCE: 26

Gly Gly Asn Asn Ile Gly Ser Lys Ser Val His
1               5                   10

<210> SEQ ID NO 27
<211> LENGTH: 7
<212> TYPE: PRT
<213> ORGANISM: Artificial Sequence
<220> FEATURE:
<223> OTHER INFORMATION: BCMB69 LCDR2

<400> SEQUENCE: 27

Asp Asp Ser Asp Arg Pro Ser
1               5

<210> SEQ ID NO 28
<211> LENGTH: 11
<212> TYPE: PRT
<213> ORGANISM: Artificial Sequence
<220> FEATURE:
<223> OTHER INFORMATION: BCMB69 LCDR3

<400> SEQUENCE: 28

Gln Val Trp Asp Ser Ser Ser Asp His Val Val
1               5                   10

<210> SEQ ID NO 29
<211> LENGTH: 121
<212> TYPE: PRT
<213> ORGANISM: Artificial Sequence
<220> FEATURE:
<223> OTHER INFORMATION: BCMB69 VH

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser
        115                 120

<210> SEQ ID NO 30
<211> LENGTH: 111
<212> TYPE: PRT
<213> ORGANISM: Artificial Sequence
<220> FEATURE:
<223> OTHER INFORMATION: BCMB69 VL

<400> SEQUENCE: 30
```

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu Gly Gln Pro
            100                 105                 110

<210> SEQ ID NO 31
<211> LENGTH: 448
<212> TYPE: PRT
<213> ORGANISM: Artificial Sequence
<220> FEATURE:
<223> OTHER INFORMATION: BCMB69 HC

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
           260                 265                 270

Glu Val Gln Phe Asn Trp Tyr Val Asp Gly Val Glu Val His Asn Ala
       275                 280                 285

Lys Thr Lys Pro Arg Glu Glu Gln Phe Asn Ser Thr Tyr Arg Val Val
   290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
               325                 330                 335

Ile Ser Lys Ala Lys Gly Gln Pro Arg Glu Pro Gln Val Tyr Thr Leu
           340                 345                 350

Pro Pro Ser Gln Glu Glu Met Thr Lys Asn Gln Val Ser Leu Thr Cys
       355                 360                 365

Leu Val Lys Gly Phe Tyr Pro Ser Asp Ile Ala Val Glu Trp Glu Ser
   370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
               405                 410                 415

Arg Trp Gln Glu Gly Asn Val Phe Ser Cys Ser Val Met His Glu Ala
           420                 425                 430

Leu His Asn His Tyr Thr Gln Lys Ser Leu Ser Leu Ser Leu Gly Lys
       435                 440                 445

<210> SEQ ID NO 32
<211> LENGTH: 214
<212> TYPE: PRT
<213> ORGANISM: Artificial Sequence
<220> FEATURE:
<223> OTHER INFORMATION: BCMB69 LC

<400> SEQUENCE: 32

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
           20                  25                  30

His Trp Tyr Gln Gln Pro Pro Gly Gln Ala Pro Val Val Val Val Tyr
       35                  40                  45

Asp Asp Ser Asp Arg Pro Ser Gly Ile Pro Glu Arg Phe Ser Gly Ser
   50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
               85                  90                  95

Val Val Phe Gly Gly Gly Thr Lys Leu Thr Val Leu Gly Gln Pro Lys
           100                 105                 110

Ala Ala Pro Ser Val Thr Leu Phe Pro Pro Ser Ser Glu Glu Leu Gln
       115                 120                 125

Ala Asn Lys Ala Thr Leu Val Cys Leu Ile Ser Asp Phe Tyr Pro Gly
   130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
               165                 170                 175

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 33
<211> LENGTH: 5
<212> TYPE: PRT
<213> ORGANISM: Artificial Sequence
<220> FEATURE:
<223> OTHER INFORMATION: CD3B219 HCDR1

<400> SEQUENCE: 33

Thr Tyr Ala Met Asn
1               5

<210> SEQ ID NO 34
<211> LENGTH: 19
<212> TYPE: PRT
<213> ORGANISM: Artificial Sequence
<220> FEATURE:
<223> OTHER INFORMATION: CD3B219 HCDR2

<400> SEQUENCE: 34

Arg Ile Arg Ser Lys Tyr Asn Asn Tyr Ala Thr Tyr Tyr Ala Ala Ser
1               5                   10                  15

Val Lys Gly

<210> SEQ ID NO 35
<211> LENGTH: 14
<212> TYPE: PRT
<213> ORGANISM: Artificial Sequence
<220> FEATURE:
<223> OTHER INFORMATION: CD3B219 HCDR3

<400> SEQUENCE: 35

His Gly Asn Phe Gly Asn Ser Tyr Val Ser Trp Phe Ala Tyr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: CD3B219 LCDR1

<400> SEQUENCE: 36

Arg Ser Ser Thr Gly Ala Val Thr Thr Ser Asn Tyr Ala Asn
1               5                   10

<210> SEQ ID NO 37
<211> LENGTH: 7
<212> TYPE: PRT
<213> ORGANISM: Artificial Sequence
<220> FEATURE:
<223> OTHER INFORMATION: CD3B219 LCDR2

<400> SEQUENCE: 37

Gly Thr Asn Lys Arg Ala Pro
1               5

<210> SEQ ID NO 38
```

```
<211> LENGTH: 9
<212> TYPE: PRT
<213> ORGANISM: Artificial Sequence
<220> FEATURE:
<223> OTHER INFORMATION: CD3B219 LCDR3

<400> SEQUENCE: 38

Ala Leu Trp Tyr Ser Asn Leu Trp Val
1               5

<210> SEQ ID NO 39
<211> LENGTH: 125
<212> TYPE: PRT
<213> ORGANISM: Artificial Sequence
<220> FEATURE:
<223> OTHER INFORMATION: CD3B219 VH

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 40
<211> LENGTH: 112
<212> TYPE: PRT
<213> ORGANISM: Artificial Sequence
<220> FEATURE:
<223> OTHER INFORMATION: CD3BB219 VL

<400> SEQUENCE: 40

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

<210> SEQ ID NO 41
<211> LENGTH: 452
```

<212> TYPE: PRT
<213> ORGANISM: Artificial Sequence
<220> FEATURE:
<223> OTHER INFORMATION: CD3B219 HC

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 42
<211> LENGTH: 215
<212> TYPE: PRT
<213> ORGANISM: Artificial Sequence
<220> FEATURE:
<223> OTHER INFORMATION: CD3219 LC

<400> SEQUENCE: 42

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 43
<211> LENGTH: 5
<212> TYPE: PRT
<213> ORGANISM: Artificial Sequence
<220> FEATURE:
<223> OTHER INFORMATION: GC5B596 HCDR1

<400> SEQUENCE: 43

Gly Tyr Thr Met Asn
1               5
```

<210> SEQ ID NO 44
<211> LENGTH: 17
<212> TYPE: PRT
<213> ORGANISM: Artificial Sequence
<220> FEATURE:
<223> OTHER INFORMATION: GC5B596 HCDR2

<400> SEQUENCE: 44

Leu Ile Asn Pro Tyr Asn Ser Asp Thr Asn Tyr Ala Gln Lys Leu Gln
1               5                   10                  15

Gly

<210> SEQ ID NO 45
<211> LENGTH: 9
<212> TYPE: PRT
<213> ORGANISM: Artificial Sequence
<220> FEATURE:
<223> OTHER INFORMATION: GC5B596 HCDR3

<400> SEQUENCE: 45

Val Ala Leu Arg Val Ala Leu Asp Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: GC5B596 LCDR1

<400> SEQUENCE: 46

Lys Ala Ser Gln Asn Val Ala Thr His Val Gly
1               5                   10

<210> SEQ ID NO 47
<211> LENGTH: 7
<212> TYPE: PRT
<213> ORGANISM: Artificial Sequence
<220> FEATURE:
<223> OTHER INFORMATION: GC5B596 LCDR2

<400> SEQUENCE: 47

Ser Ala Ser Tyr Arg Tyr Ser
1               5

<210> SEQ ID NO 48
<211> LENGTH: 9
<212> TYPE: PRT
<213> ORGANISM: Artificial Sequence
<220> FEATURE:
<223> OTHER INFORMATION: GC5B596 LCDR3

<400> SEQUENCE: 48

Gln Gln Tyr Asn Arg Tyr Pro Tyr Thr
1               5

<210> SEQ ID NO 49
<211> LENGTH: 118
<212> TYPE: PRT
<213> ORGANISM: Artificial Sequence
<220> FEATURE:
<223> OTHER INFORMATION: GC5B596 VH

<400> SEQUENCE: 49

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
            35                  40                  45

Gly Leu Ile Asn Pro Tyr Asn Ser Asp Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Val Ala Leu Arg Val Ala Leu Asp Tyr Trp Gly Gln Gly Thr
            100                 105                 110

Leu Val Thr Val Ser Ser
            115
```

<210> SEQ ID NO 50
<211> LENGTH: 107
<212> TYPE: PRT
<213> ORGANISM: Artificial Sequence
<220> FEATURE:
<223> OTHER INFORMATION: GC5B596 VL

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
            20                  25                  30

Val Gly Trp Tyr Gln Gln Lys Pro Gly Lys Ala Pro Lys Arg Leu Ile
            35                  40                  45

Tyr Ser Ala Ser Tyr Arg Tyr Ser Gly Val Pro Ser Arg Phe Ser Gly
            50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
            85                  90                  95

Thr Phe Gly Gln Gly Thr Lys Leu Glu Ile Lys
            100                 105
```

<210> SEQ ID NO 51
<211> LENGTH: 445
<212> TYPE: PRT
<213> ORGANISM: Artificial Sequence
<220> FEATURE:
<223> OTHER INFORMATION: GC5B596 HC

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
            35                  40                  45

Gly Leu Ile Asn Pro Tyr Asn Ser Asp Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                 85                  90                  95

Ala Arg Val Ala Leu Arg Val Ala Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Gly Lys
            435                 440                 445

<210> SEQ ID NO 52
<211> LENGTH: 210
<212> TYPE: PRT
<213> ORGANISM: Artificial Sequence
<220> FEATURE:
<223> OTHER INFORMATION: GC5B596 LC

<400> SEQUENCE: 52
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
            20                  25                  30

Val Gly Trp Tyr Gln Gln Lys Pro Gly Lys Ala Pro Lys Arg Leu Ile
        35                  40                  45

Tyr Ser Ala Ser Tyr Arg Tyr Ser Gly Val Pro Ser Arg Phe Ser Gly
50                      55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys Lys Ala Ala Pro Ser
            100                 105                 110

Val Thr Leu Phe Pro Pro Ser Ser Glu Glu Leu Gln Ala Asn Lys Ala
        115                 120                 125

Thr Leu Val Cys Leu Ile Ser Asp Phe Tyr Pro Gly Ala Val Thr Val
    130                 135                 140

Ala Trp Lys Gly Asp Ser Ser Pro Val Lys Ala Gly Val Glu Thr Thr
145                 150                 155                 160

Thr Pro Ser Lys Gln Ser Asn Asn Lys Tyr Ala Ala Ser Ser Tyr Leu
            165                 170                 175

Ser Leu Thr Pro Glu Gln Trp Lys Ser His Arg Ser Tyr Ser Cys Gln
            180                 185                 190

Val Thr His Glu Gly Ser Thr Val Glu Lys Thr Val Ala Pro Thr Glu
            195                 200                 205

Cys Ser
    210

<210> SEQ ID NO 53
<211> LENGTH: 500
<212> TYPE: PRT
<213> ORGANISM: Artificial Sequence
<220> FEATURE:
<223> OTHER INFORMATION: blinatumomab

<400> SEQUENCE: 53

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                      55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140
```

```
Lys Ile Ser Cys Lys Ala Ser Gly Tyr Ala Phe Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
            195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Asp
            245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
    275                 280                 285

Met His Trp Val Lys Gln Arg Pro Gly Gln Gly Leu Glu Trp Ile Gly
290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
            405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
            435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
            485                 490                 495

Leu Lys His His
        500

<210> SEQ ID NO 54
<211> LENGTH: 5
<212> TYPE: PRT
<213> ORGANISM: Artificial Sequence
<220> FEATURE:
<223> OTHER INFORMATION: PSMB127 HCDR1

<400> SEQUENCE: 54
```

```
Ser Asp Ala Met His
1               5
```

```
<210> SEQ ID NO 55
<211> LENGTH: 17
<212> TYPE: PRT
<213> ORGANISM: Artificial Sequence
<220> FEATURE:
<223> OTHER INFORMATION: -PSMB127 HCDR2

<400> SEQUENCE: 55
```

```
Glu Ile Ser Gly Ser Gly Gly Tyr Thr Asn Tyr Ala Asp Ser Val Lys
1               5                   10                  15

Gly
```

```
<210> SEQ ID NO 56
<211> LENGTH: 15
<212> TYPE: PRT
<213> ORGANISM: Artificial Sequence
<220> FEATURE:
<223> OTHER INFORMATION: PSMB127 HCDR3

<400> SEQUENCE: 56
```

```
Asp Ser Tyr Asp Ser Ser Leu Tyr Val Gly Asp Tyr Phe Asp Tyr
1               5                   10                  15
```

```
<210> SEQ ID NO 57
<211> LENGTH: 378
<212> TYPE: PRT
<213> ORGANISM: Homo sapiens

<400> SEQUENCE: 57
```

```
Met Val Leu Leu Trp Leu Thr Leu Leu Ile Ala Leu Pro Cys Leu
1               5                   10                  15

Leu Gln Thr Lys Glu Asp Pro Asn Pro Pro Ile Thr Asn Leu Arg Met
                20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
            115                 120                 125

Gly Ala Pro Ala Asp Val Gln Tyr Asp Leu Tyr Leu Asn Val Ala Asn
        130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
            195                 200                 205

Thr Pro Pro Asn Met Thr Ala Lys Cys Asn Lys Thr His Ser Phe Met
```

```
                210                 215                 220
His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
                260                 265                 270

Arg Ala Arg Glu Arg Val Tyr Glu Phe Leu Ser Ala Trp Ser Thr Pro
                275                 280                 285

Gln Arg Phe Glu Cys Asp Gln Glu Glu Gly Ala Asn Thr Arg Ala Trp
                290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
                340                 345                 350

Lys Leu Val Val Trp Glu Ala Gly Lys Ala Gly Leu Glu Glu Cys Leu
                355                 360                 365

Val Thr Glu Val Gln Val Val Gln Lys Thr
                370                 375

<210> SEQ ID NO 58
<211> LENGTH: 556
<212> TYPE: PRT
<213> ORGANISM: Homo sapiens

<400> SEQUENCE: 58

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
                35                  40                  45

Gln Leu Thr Trp Ser Arg Glu Ser Pro Leu Lys Pro Phe Leu Lys Leu
                50                  55                  60

Ser Leu Gly Leu Pro Gly Leu Gly Ile His Met Arg Pro Leu Ala Ile
65              70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
                115                 120                 125

Leu Gly Gly Leu Gly Cys Gly Leu Lys Asn Arg Ser Ser Glu Gly Pro
                130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
                195                 200                 205
```

-continued

```
Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 59
<211> LENGTH: 9
<212> TYPE: PRT
<213> ORGANISM: Artificial Sequence
<220> FEATURE:
<223> OTHER INFORMATION: PSMB127 LCDR3

<400> SEQUENCE: 59

Gln Gln Arg Ser Asn Trp Pro Leu Thr
1               5
```

<210> SEQ ID NO 60
<211> LENGTH: 124
<212> TYPE: PRT
<213> ORGANISM: Artificial Sequence
<220> FEATURE:
<223> OTHER INFORMATION: PSMB127 VH

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser
        115                 120

<210> SEQ ID NO 61
<211> LENGTH: 107
<212> TYPE: PRT
<213> ORGANISM: Artificial Sequence
<220> FEATURE:
<223> OTHER INFORMATION: PSMB127 VL

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 62
<211> LENGTH: 451
<212> TYPE: PRT
<213> ORGANISM: Artificial Sequence
<220> FEATURE:
<223> OTHER INFORMATION: PSMB127 HC

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp

-continued

```
                20                  25                  30
Ala Met His Trp Val Arg Gln Ala Pro Gly Lys Gly Leu Glu Trp Val
            35                  40                  45
Ser Glu Ile Ser Gly Ser Gly Gly Tyr Thr Asn Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Asp Ser Tyr Asp Ser Ser Leu Tyr Val Gly Asp Tyr Phe Asp
            100                 105                 110
Tyr Trp Gly Gln Gly Thr Leu Val Thr Val Ser Ser Ala Ser Thr Lys
            115                 120                 125
Gly Pro Ser Val Phe Pro Leu Ala Pro Cys Ser Arg Ser Thr Ser Glu
            130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Lys Thr Tyr Thr Cys Asn
            195                 200                 205
Val Asp His Lys Pro Ser Asn Thr Lys Val Asp Lys Arg Val Glu Ser
            210                 215                 220
Lys Tyr Gly Pro Pro Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser Gln
            260                 265                 270
Glu Asp Pro Glu Val Gln Phe Asn Trp Tyr Val Asp Gly Val Glu Val
            275                 280                 285
His Asn Ala Lys Thr Lys Pro Arg Glu Glu Gln Phe Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Gln Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
            420                 425                 430
His Glu Ala Leu His Asn His Tyr Thr Gln Lys Ser Leu Ser Leu Ser
            435                 440                 445
```

Leu Gly Lys
    450

<210> SEQ ID NO 63
<211> LENGTH: 214
<212> TYPE: PRT
<213> ORGANISM: Artificial Sequence
<220> FEATURE:
<223> OTHER INFORMATION: PSMB127 LC

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 5
<212> TYPE: PRT
<213> ORGANISM: Artificial Sequence
<220> FEATURE:
<223> OTHER INFORMATION: TMEB762 HCDR1

<400> SEQUENCE: 64

Ser Tyr Ser Met Ser
1               5

<210> SEQ ID NO 65
<211> LENGTH: 17
<212> TYPE: PRT
<213> ORGANISM: Artificial Sequence
<220> FEATURE:
<223> OTHER INFORMATION: TMEB762 HCDR2

<400> SEQUENCE: 65

```
Val Ile Ser Gly Ser Gly Gly Phe Thr Asp Tyr Ala Asp Ser Val Lys
1               5                   10                  15

Gly

<210> SEQ ID NO 66
<211> LENGTH: 9
<212> TYPE: PRT
<213> ORGANISM: Artificial Sequence
<220> FEATURE:
<223> OTHER INFORMATION: TMEB762 HCDR3

<400> SEQUENCE: 66

Met Pro Leu Asn Ser Pro His Asp Tyr
1               5

<210> SEQ ID NO 67
<211> LENGTH: 11
<212> TYPE: PRT
<213> ORGANISM: Artificial Sequence
<220> FEATURE:
<223> OTHER INFORMATION: TMEB762 LCDR1

<400> SEQUENCE: 67

Arg Ala Ser Gln Gly Ile Arg Asn Asp Leu Gly
1               5                   10

<210> SEQ ID NO 68
<211> LENGTH: 7
<212> TYPE: PRT
<213> ORGANISM: Artificial Sequence
<220> FEATURE:
<223> OTHER INFORMATION: TMEB762 LCDR2

<400> SEQUENCE: 68

Ala Ala Ser Ser Leu Gln Ser
1               5

<210> SEQ ID NO 69
<211> LENGTH: 9
<212> TYPE: PRT
<213> ORGANISM: Artificial Sequence
<220> FEATURE:
<223> OTHER INFORMATION: TMEB762 LCDR3

<400> SEQUENCE: 69

Leu Gln Asp Tyr Asn Tyr Pro Leu Thr
1               5

<210> SEQ ID NO 70
<211> LENGTH: 118
<212> TYPE: PRT
<213> ORGANISM: Artificial Sequence
<220> FEATURE:
<223> OTHER INFORMATION: TMEB762 VH

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Val Ile Ser Gly Ser Gly Gly Phe Thr Asp Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Pro Leu Asn Ser Pro His Asp Tyr Trp Gly Gln Gly Thr
            100                 105                 110

Leu Val Thr Val Ser Ser
        115

<210> SEQ ID NO 71
<211> LENGTH: 107
<212> TYPE: PRT
<213> ORGANISM: Artificial Sequence
<220> FEATURE:
<223> OTHER INFORMATION: TMEB762 VL

<400> SEQUENCE: 71

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
                 85                  90                  95

Thr Phe Gly Gly Gly Thr Lys Val Glu Ile Lys
            100                 105

<210> SEQ ID NO 72
<211> LENGTH: 444
<212> TYPE: PRT
<213> ORGANISM: Artificial Sequence
<220> FEATURE:
<223> OTHER INFORMATION: TMEB762 HC

<400> SEQUENCE: 72

Val Gln Leu Leu Glu Ser Gly Gly Gly Leu Val Gln Pro Gly Gly Ser
  1               5                  10                  15

Leu Arg Leu Ser Cys Ala Ala Ser Gly Phe Thr Phe Ser Ser Tyr Ser
             20                  25                  30

Met Ser Trp Val Arg Gln Ala Pro Gly Lys Gly Leu Glu Trp Val Ser
         35                  40                  45

Val Ile Ser Gly Ser Gly Gly Phe Thr Asp Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Met Pro Leu Asn Ser Pro His Asp Tyr Trp Gly Gln Gly Thr Leu
            100                 105                 110

Val Thr Val Ser Ser Ala Ser Thr Lys Gly Pro Ser Val Phe Pro Leu
         115                 120                 125

Ala Pro Cys Ser Arg Ser Thr Ser Glu Ser Thr Ala Ala Leu Gly Cys
    130                 135                 140
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Lys Thr Tyr Thr Cys Asn Val Asp His Lys Pro Ser Asn
    195                 200                 205

Thr Lys Val Asp Lys Arg Val Glu Ser Lys Tyr Gly Pro Pro Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
    435                 440

<210> SEQ ID NO 73
<211> LENGTH: 214
<212> TYPE: PRT
<213> ORGANISM: Artificial Sequence
<220> FEATURE:
<223> OTHER INFORMATION: TMEB762 LC

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Leu
             85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 7
<212> TYPE: PRT
<213> ORGANISM: Artificial Sequence
<220> FEATURE:
<223> OTHER INFORMATION: CD3B396 HCDR1

<400> SEQUENCE: 74

Asn Asn Asn Ala Ala Trp Ser
1               5

<210> SEQ ID NO 75
<211> LENGTH: 18
<212> TYPE: PRT
<213> ORGANISM: Artificial Sequence
<220> FEATURE:
<223> OTHER INFORMATION: CD3B396 HCDR2

<400> SEQUENCE: 75

Arg Thr Tyr Tyr Arg Ser Lys Trp Leu Tyr Asp Tyr Ala Val Ser Val
1               5                   10                  15

Lys Ser

<210> SEQ ID NO 76
<211> LENGTH: 8
<212> TYPE: PRT
<213> ORGANISM: Artificial Sequence
<220> FEATURE:
<223> OTHER INFORMATION: CD3B396 HCDR3

<400> SEQUENCE: 76

Gly Tyr Ser Ser Ser Phe Asp Tyr
1               5

<210> SEQ ID NO 77
<211> LENGTH: 14
<212> TYPE: PRT
<213> ORGANISM: Artificial Sequence
<220> FEATURE:
<223> OTHER INFORMATION: CD3B396 LCDR1
```

<400> SEQUENCE: 77

Thr Gly Thr Ser Ser Asn Ile Gly Thr Tyr Lys Phe Val Ser
1               5                   10

<210> SEQ ID NO 78
<211> LENGTH: 7
<212> TYPE: PRT
<213> ORGANISM: Artificial Sequence
<220> FEATURE:
<223> OTHER INFORMATION: CD3B396 LCDR2

<400> SEQUENCE: 78

Glu Val Ser Lys Arg Pro Ser
1               5

<210> SEQ ID NO 79
<211> LENGTH: 10
<212> TYPE: PRT
<213> ORGANISM: Artificial Sequence
<220> FEATURE:
<223> OTHER INFORMATION: CD3B396 LCDR3

<400> SEQUENCE: 79

Val Ser Tyr Ala Gly Ser Gly Thr Leu Leu
1               5                   10

<210> SEQ ID NO 80
<211> LENGTH: 120
<212> TYPE: PRT
<213> ORGANISM: Artificial Sequence
<220> FEATURE:
<223> OTHER INFORMATION: CD3B396 VH

<400> SEQUENCE: 80

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Ser Phe Asp Tyr Trp Gly Gln
            100                 105                 110

Gly Thr Leu Val Thr Val Ser Ser
        115                 120

<210> SEQ ID NO 81
<211> LENGTH: 110
<212> TYPE: PRT
<213> ORGANISM: Artificial Sequence
<220> FEATURE:
<223> OTHER INFORMATION: CD3B396 VL

<400> SEQUENCE: 81

Gln Ser Ala Leu Thr Gln Pro Ala Ser Val Ser Gly Ser Pro Gly Gln
1               5                   10                  15

-continued

```
Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Gly Thr Lys Leu Thr Val Leu
            100                 105                 110

<210> SEQ ID NO 82
<211> LENGTH: 447
<212> TYPE: PRT
<213> ORGANISM: Artificial Sequence
<220> FEATURE:
<223> OTHER INFORMATION: CD3B396 HC

<400> SEQUENCE: 82

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Ser Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Leu Leu Tyr Ser Lys Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 83
<211> LENGTH: 216
<212> TYPE: PRT
<213> ORGANISM: Artificial Sequence
<220> FEATURE:
<223> OTHER INFORMATION: CD3B396 LC

<400> SEQUENCE: 83

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 84
<211> LENGTH: 5
<212> TYPE: PRT
<213> ORGANISM: Artificial Sequence
<220> FEATURE:
<223> OTHER INFORMATION: C33B904 HCDR1

<400> SEQUENCE: 84

Asp Tyr Ala Met His
1               5

<210> SEQ ID NO 85
<211> LENGTH: 17
<212> TYPE: PRT
<213> ORGANISM: Artificial Sequence
<220> FEATURE:
<223> OTHER INFORMATION: C33B904 HCDR2

<400> SEQUENCE: 85

Gly Ile Gly Trp Ser Gly Gly Ser Ile Val Tyr Ala Asp Ser Val Lys
1               5                   10                  15

Gly

<210> SEQ ID NO 86
<211> LENGTH: 10
<212> TYPE: PRT
<213> ORGANISM: Artificial Sequence
<220> FEATURE:
<223> OTHER INFORMATION: C33B904 HCDR3

<400> SEQUENCE: 86

Asp Ser Pro Tyr Gly Asp Phe Phe Asp Tyr
1               5                   10

<210> SEQ ID NO 87
<211> LENGTH: 17
<212> TYPE: PRT
<213> ORGANISM: Artificial Sequence
<220> FEATURE:
<223> OTHER INFORMATION: C33B904 LCDR1

<400> SEQUENCE: 87

Lys Ser Ser Gln Thr Val Phe Tyr Ser Ser Asn Asn Lys Asn Tyr Leu
1               5                   10                  15

Ala

<210> SEQ ID NO 88
<211> LENGTH: 7
<212> TYPE: PRT
<213> ORGANISM: Artificial Sequence
<220> FEATURE:
<223> OTHER INFORMATION: C33B904 LCDR2

<400> SEQUENCE: 88

Trp Ala Ser Thr Arg Lys Ser
1               5

<210> SEQ ID NO 89
<211> LENGTH: 9
<212> TYPE: PRT

```
<213> ORGANISM: Artificial Sequence
<220> FEATURE:
<223> OTHER INFORMATION: C33B904 LCDR3

<400> SEQUENCE: 89

Gln His Tyr Tyr Ser Thr Pro Tyr Thr
1               5

<210> SEQ ID NO 90
<211> LENGTH: 119
<212> TYPE: PRT
<213> ORGANISM: Artificial Sequence
<220> FEATURE:
<223> OTHER INFORMATION: -C33B904 VH

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Pro Tyr Gly Asp Phe Phe Asp Tyr Trp Gly Gln Gly
            100                 105                 110

Thr Leu Val Thr Val Ser Ser
        115

<210> SEQ ID NO 91
<211> LENGTH: 113
<212> TYPE: PRT
<213> ORGANISM: Artificial Sequence
<220> FEATURE:
<223> OTHER INFORMATION: C33B904 VL

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Val Ser Ser Leu Gln Ala Glu Asp Val Ala Val Tyr Tyr Cys Gln His
                85                  90                  95

Tyr Tyr Ser Thr Pro Tyr Thr Phe Gly Gln Gly Thr Lys Leu Glu Ile
            100                 105                 110

Lys

<210> SEQ ID NO 92
<211> LENGTH: 446
```

<212> TYPE: PRT
<213> ORGANISM: Artificial Sequence
<220> FEATURE:
<223> OTHER INFORMATION: C33B904 HC

<400> SEQUENCE: 92

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Pro Tyr Gly Asp Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

-continued

```
Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys
    435                 440                 445

<210> SEQ ID NO 93
<211> LENGTH: 216
<212> TYPE: PRT
<213> ORGANISM: Artificial Sequence
<220> FEATURE:
<223> OTHER INFORMATION: C33B904 LC

<400> SEQUENCE: 93

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Val Ser Ser Leu Gln Ala Glu Asp Val Ala Val Tyr Tyr Cys Gln His
                85                  90                  95

Tyr Tyr Ser Thr Pro Tyr Thr Phe Gly Gln Gly Thr Lys Leu Glu Ile
            100                 105                 110

Lys Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Gly Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 94
<211> LENGTH: 5
<212> TYPE: PRT
<213> ORGANISM: Artificial Sequence
<220> FEATURE:
<223> OTHER INFORMATION: I3RB218 HCDR1

<400> SEQUENCE: 94

Gly Tyr Trp Met His
1               5

<210> SEQ ID NO 95
```

```
<211> LENGTH: 17
<212> TYPE: PRT
<213> ORGANISM: Artificial Sequence
<220> FEATURE:
<223> OTHER INFORMATION: I3RB218 HCDR2

<400> SEQUENCE: 95

Ala Ile Arg Ser Asp Gly Ser Ser Lys Tyr Tyr Ala Asp Ser Val Lys
1               5                   10                  15

Gly

<210> SEQ ID NO 96
<211> LENGTH: 10
<212> TYPE: PRT
<213> ORGANISM: Artificial Sequence
<220> FEATURE:
<223> OTHER INFORMATION: I3RB218 HCDR3

<400> SEQUENCE: 96

Asp Gly Val Ile Glu Asp Thr Phe Asp Tyr
1               5                   10

<210> SEQ ID NO 97
<211> LENGTH: 364
<212> TYPE: PRT
<213> ORGANISM: Homo sapiens

<400> SEQUENCE: 97

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
210                 215                 220

Arg Thr Ile Gln Leu Asn Val Thr Tyr Val Pro Gln Asn Pro Thr Thr
225                 230                 235                 240
```

```
Gly Ile Phe Pro Gly Asp Gly Ser Gly Lys Gln Glu Thr Arg Ala Gly
            245                 250                 255

Val Val His Gly Ala Ile Gly Gly Ala Gly Val Thr Ala Leu Leu Ala
        260                 265                 270

Leu Cys Leu Cys Leu Ile Phe Phe Ile Val Lys Thr His Arg Arg Lys
    275                 280                 285

Ala Ala Arg Thr Ala Val Gly Arg Asn Asp Thr His Pro Thr Thr Gly
290                 295                 300

Ser Ala Ser Pro Lys His Gln Lys Lys Ser Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 98
<211> LENGTH: 345
<212> TYPE: PRT
<213> ORGANISM: Homo sapiens

<400> SEQUENCE: 98

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
        115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255
```

```
Tyr Ile Val Pro Glu Leu Cys Ile Leu Tyr Arg Ser Cys Arg Gln Glu
                260                 265                 270

Cys Pro Leu Gln Gly Asn Ala Cys Pro Val Thr Ala Tyr Gln His Ser
            275                 280                 285

Phe Gln Val Glu Asn Gln Glu Leu Ser Arg Ala Arg Asp Ser Asp Gly
        290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345

<210> SEQ ID NO 99
<211> LENGTH: 750
<212> TYPE: PRT
<213> ORGANISM: Homo sapiens

<400> SEQUENCE: 99

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
```

```
                275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
        370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
    450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
            500                 505                 510
Ser Lys Leu Gly Ser Gly Asn Asp Phe Glu Val Phe Phe Gln Arg Leu
        515                 520                 525
Gly Ile Ala Ser Gly Arg Ala Arg Tyr Thr Lys Asn Trp Glu Thr Asn
    530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
            580                 585                 590
Leu Pro Phe Asp Cys Arg Asp Tyr Ala Val Val Leu Arg Lys Tyr Ala
        595                 600                 605
Asp Lys Ile Tyr Ser Ile Ser Met Lys His Pro Gln Glu Met Lys Thr
    610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
            660                 665                 670
Arg Ala Phe Ile Asp Pro Leu Gly Leu Pro Asp Arg Pro Phe Tyr Arg
        675                 680                 685
His Val Ile Tyr Ala Pro Ser Ser His Asn Lys Tyr Ala Gly Glu Ser
    690                 695                 700
```

```
Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750
```

<210> SEQ ID NO 100
<211> LENGTH: 119
<212> TYPE: PRT
<213> ORGANISM: Artificial Sequence
<220> FEATURE:
<223> OTHER INFORMATION: 3RB218 VH

<400> SEQUENCE: 100

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Ala Ile Arg Ser Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val Ile Glu Asp Thr Phe Asp Tyr Trp Gly Gln Gly
            100                 105                 110

Thr Leu Val Thr Val Ser Ser
        115
```

<210> SEQ ID NO 101
<211> LENGTH: 374
<212> TYPE: PRT
<213> ORGANISM: Homo sapiens

<400> SEQUENCE: 101

```
Met Val Leu Trp Glu Ser Pro Arg Gln Cys Ser Ser Trp Thr Leu Cys
1               5                   10                  15

Glu Gly Phe Cys Trp Leu Leu Leu Pro Val Met Leu Leu Ile Val
            20                  25                  30

Ala Arg Pro Val Lys Leu Ala Ala Phe Pro Thr Ser Leu Ser Asp Cys
        35                  40                  45

Gln Thr Pro Thr Gly Trp Asn Cys Ser Gly Tyr Asp Asp Arg Glu Asn
    50                  55                  60

Asp Leu Phe Leu Cys Asp Thr Asn Thr Cys Lys Phe Asp Gly Glu Cys
65                  70                  75                  80

Leu Arg Ile Gly Asp Thr Val Thr Cys Val Cys Gln Phe Lys Cys Asn
                85                  90                  95

Asn Asp Tyr Val Pro Val Cys Gly Ser Asn Gly Glu Ser Tyr Gln Asn
            100                 105                 110

Glu Cys Tyr Leu Arg Gln Ala Ala Cys Lys Gln Gln Ser Glu Ile Leu
        115                 120                 125

Val Val Ser Glu Gly Ser Cys Ala Thr Asp Ala Gly Ser Gly Ser Gly
    130                 135                 140
```

```
Asp Gly Val His Glu Gly Ser Gly Glu Thr Ser Gln Lys Glu Thr Ser
145                 150                 155                 160

Thr Cys Asp Ile Cys Gln Phe Gly Ala Glu Cys Asp Glu Asp Ala Glu
                165                 170                 175

Asp Val Trp Cys Val Cys Asn Ile Asp Cys Ser Gln Thr Asn Phe Asn
            180                 185                 190

Pro Leu Cys Ala Ser Asp Gly Lys Ser Tyr Asp Asn Ala Cys Gln Ile
        195                 200                 205

Lys Glu Ala Ser Cys Gln Lys Gln Glu Lys Ile Glu Val Met Ser Leu
    210                 215                 220

Gly Arg Cys Gln Asp Asn Thr Thr Thr Thr Lys Ser Glu Asp Gly
225                 230                 235                 240

His Tyr Ala Arg Thr Asp Tyr Ala Glu Asn Ala Asn Lys Leu Glu Glu
                245                 250                 255

Ser Ala Arg Glu His His Ile Pro Cys Pro Glu His Tyr Asn Gly Phe
            260                 265                 270

Cys Met His Gly Lys Cys Glu His Ser Ile Asn Met Gln Glu Pro Ser
        275                 280                 285

Cys Arg Cys Asp Ala Gly Tyr Thr Gly Gln His Cys Glu Lys Lys Asp
    290                 295                 300

Tyr Ser Val Leu Tyr Val Val Pro Gly Pro Val Arg Phe Gln Tyr Val
305                 310                 315                 320

Leu Ile Ala Ala Val Ile Gly Thr Ile Gln Ile Ala Val Ile Cys Val
                325                 330                 335

Val Val Leu Cys Ile Thr Arg Lys Cys Pro Arg Ser Asn Arg Ile His
            340                 345                 350

Arg Gln Lys Gln Asn Thr Gly His Tyr Ser Ser Asp Asn Thr Thr Arg
        355                 360                 365

Ala Ser Thr Arg Leu Ile
        370

<210> SEQ ID NO 102
<211> LENGTH: 446
<212> TYPE: PRT
<213> ORGANISM: Artificial Sequence
<220> FEATURE:
<223> OTHER INFORMATION: I3RB218 HC

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Ala Ile Arg Ser Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val Ile Glu Asp Thr Phe Asp Tyr Trp Gly Gln Gly
            100                 105                 110

Thr Leu Val Thr Val Ser Ser Ala Ser Thr Lys Gly Pro Ser Val Phe
        115                 120                 125
```

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 103
<211> LENGTH: 330
<212> TYPE: PRT
<213> ORGANISM: Homo sapiens

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 327
<212> TYPE: PRT
<213> ORGANISM: Homo sapiens

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro

```
                100             105             110
    Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
    145                 150                 155                 160

Gly Val Glu Val His Asn Ala Lys Thr Lys Pro Arg Glu Glu Gln Phe
                    165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
    225                 230                 235                 240

Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
    305                 310                 315                 320

Leu Ser Leu Ser Leu Gly Lys
                    325

<210> SEQ ID NO 105
<211> LENGTH: 509
<212> TYPE: PRT
<213> ORGANISM: Artificial Sequence
<220> FEATURE:
<223> OTHER INFORMATION: rHuPH20

<400> SEQUENCE: 105

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
```

```
            130                 135                 140
Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
                180                 185                 190

Glu Lys Ala Gly Lys Asp Phe Leu Val Glu Thr Ile Lys Leu Gly Lys
                195                 200                 205

Leu Leu Arg Pro Asn His Leu Trp Gly Tyr Tyr Leu Phe Pro Asp Cys
        210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
        290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
        450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505
```